United States Patent
Ghosh

(10) Patent No.: US 8,921,349 B2
(45) Date of Patent: Dec. 30, 2014

(54) COMPOUNDS AND METHODS FOR TREATING AIDS AND HIV INFECTIONS

(75) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 253 days.

(21) Appl. No.: 13/319,973

(22) PCT Filed: May 11, 2010

(86) PCT No.: PCT/US2010/034437
§ 371 (c)(1),
(2), (4) Date: Nov. 10, 2011

(87) PCT Pub. No.: WO2010/132494
PCT Pub. Date: Nov. 18, 2010

(65) Prior Publication Data
US 2012/0059161 A1  Mar. 8, 2012

Related U.S. Application Data

(60) Provisional application No. 61/177,086, filed on May 11, 2009.

(51) Int. Cl.
| | | |
|---|---|---|
| C07D 407/12 | (2006.01) | |
| C07D 419/12 | (2006.01) | |
| A61K 31/34 | (2006.01) | |
| C07D 519/00 | (2006.01) | |
| C07D 493/04 | (2006.01) | |
| C07D 515/04 | (2006.01) | |

(52) U.S. Cl.
CPC ............ C07D 519/00 (2013.01); C07D 493/04 (2013.01); C07D 515/04 (2013.01)
USPC .......................................... 514/183; 540/465

(58) Field of Classification Search
None
See application file for complete search history.

(56) References Cited

FOREIGN PATENT DOCUMENTS

| EP | 2429290 A1 | 3/2012 | | |
|---|---|---|---|---|
| WO | WO 97/18207 | 5/1997 | | |
| WO | WO 99/67254 | 12/1999 | | |
| WO | 03/078438 | * 3/2003 | ........... | C07D 493/04 |
| WO | WO 03049746 | 6/2003 | | |
| WO | WO-2010132494 A1 | 11/2010 | | |

OTHER PUBLICATIONS

Witvrouw. Antiviral Therapy, 2004, 9:1, 57-65.*
Extended European Search Report for EP Application No. 10775430, Dated Oct. 9, 2012, 3 pages.
Ghosh A K et al: "Design and synthesis of novel HIV-1 protease inhibitors incorporating oxyindoles as the P2'-ligands," Bioorganic & Medicinal Chemistry Letters, Pergamon, Elsevier Science, GB, vol. 16, No. 7, Apr. 1, 2006, pp. 1869-1873.
"European Application Serial No. 10775430.1, Extended European Search Report mailed Oct. 9, 2012", 5 pgs.
"European Application Serial No. 10775430.1, Office Action mailed Jul. 26, 2013", 5 pgs.
"European Application Serial No. 10775430.1, Office Action mailed Oct. 26, 2012", 1 pg.
"European Application Serial No. 10775430.1, Office Action mailed Dec. 5, 2013", 2 pgs.
"European Application Serial No. 10775430.1, Response filed Apr. 29, 2013 to Office Action mailed Oct. 26, 2013", 29 pgs.
"International Application Serial No. PCT/US2010/034437, International Preliminary Report on Patentability mailed Nov. 15, 2011", 9 pgs.
"International Application Serial No. PCT/US2010/034437, International Search Report mailed Jul. 29, 2010", 3 pgs.
"International Application Serial No. PCT/US2010/034437, Written Opinion mailed Jul. 29, 2010", 8 pgs.
International Search Report for International Application No. PCT/US2010/034437, Dated Jul. 29, 2010, 1 page.

* cited by examiner

*Primary Examiner* — Noble Jarrell
(74) *Attorney, Agent, or Firm* — Schwegman Lundberg & Woessner, P.A.

(57) ABSTRACT

Macrocycle containing carbamate compounds that inhibit HIV proteolytic enzymes and processes for preparing them are described. Compositions and methods for treating a patient infected with HIV are described.

13 Claims, 3 Drawing Sheets

COMPOUNDS AND METHODS FOR TREATING AIDS AND HIV INFECTIONS

CROSS-REFERENCE TO RELATED APPLICATIONS

This application is a national stage entry under 35 USC §371(b) of International Application No. PCT/US2010/034437, filed May 11, 2010, which claims priority under 35 USC §119(e) to U.S. Provisional Application Ser. No. 61/177,086, filed on May 11, 2009, both of which are expressly incorporated by reference herein.

GOVERNMENT RIGHTS

This invention was made with government support under grant number GM53386 awarded by the National Institutes of Health. The government has certain rights in the invention.

TECHNICAL FIELD

This invention relates to compounds that inhibit HIV proteolytic enzymes and processes for preparing the compounds. The invention also relates to methods of using the disclosed compounds for treating patients infected with HIV.

BACKGROUND AND SUMMARY

The AIDS epidemic is one of the most challenging problems in medicine in the 21st century (United Nations. 2004 Report on the global HIV/AIDS Epidemic: 4th global report. New York, U.S.A., 2004). The disclosure of the foregoing is incorporated herein in its entirety by reference. In addition, the entirety of the disclosures of each of the publications cited herein are also incorporated herein by reference. A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The introduction of protease inhibitors (PIs) into highly active antiretroviral therapy (HAART), a combination therapy based on co-administration of PIs with reverse-transcriptase inhibitors, marked the beginning of a new era in HIV/AIDS chemotherapy. HAART treatment regimens have led to a significant decline in the number of deaths due to HIV infection in the developed World (Sepkowitz, 2001). The disclosure of the foregoing is incorporated herein in its entirety by reference. In addition, the entirety of the disclosure of each of the publications cited herein is also incorporated herein by reference. Unfortunately there are a number of factors that severely limit current HAART treatment regimens. High frequency of dosing, heavy pill burden and issues of tolerability and toxicity can lead to poor adherence to treatment (Waters, 2007). The need for more potent, less toxic drug regimens is quite apparent.

Currently available combination chemotherapy typically using two reverse transcriptase inhibitors (RTIs) and boosted protease inhibitors (PIs) or an integrase inhibitor or highly active antiretroviral therapy (HAART) for human immunodeficiency virus type 1 (HIV-1) infection and AIDS has been shown to suppress the replication of HIV-1 and significantly extend the life expectancy of HIV-1-infected individuals. Indeed, several recent analyses have revealed that mortality rates for HIV infected persons have become much closer to general mortality rates since the introduction of HAART, and that first line HAART with boosted PI-based regimens resulted in less resistance within and across drug classes.

However, the ability to provide effective long-term antiretroviral therapy for HIV-1 infection has become a complex issue since those who initially achieved favorable viral suppression to undetectable levels have experienced treatment failure. In addition, it is evident that even with these anti-HIV-1 drugs, only partial immunologic reconstitution is attained in patients with advanced HIV-1 infection and it is likely that HIV-1 will eventually acquire resistance to virtually any antiviral agents. Thus, it appears that the development of potent and drug-resistant-deferring antiviral agents will continue to be required for successful long-term control of HIV-1 infection and AIDS.

It is the rapid emergence of drug resistance however, that is proving to be a most formidable problem. Mutations causing drug resistance are thought to occur spontaneously, through the recombination of mixed viral populations, and also due to drug pressure, particularly when administered at sub-standard doses (Pillay, 2006; Grabar, 2000; Wainberg, 1998; Harrigan, 2005). A growing number of patients are developing multi-drug-resistant HIV-1 variants (Hertogs, 2000; Yerly, 1999). There is ample evidence that these viral strains can be transmitted. Thus, the development of antiretroviral agents able to maintain potency against resistant HIV strains has become an urgent priority.

The proteolytic enzyme, HIV-1 protease is essential for viral assembly and maturation (Roberts, 1990; Meek, 1990; McQuade, 1990). As a consequence, design of specific inhibitors for HIV-1 protease has become the subject of immense interest. In 1996, protease inhibitors (PIs) were introduced in combination with reverse transcriptase inhibitors to become highly active antiretroviral therapy (HAART) (Flexner, 1998; Cihlar, 2000). This treatment regimen significantly increased life expectancy, improved quality of life and decreased mortality and morbidity among HIV/AIDS patients. Despite these notable advances, the emergence of drug-resistant HIV-1 variants is severely limiting the efficacy of HAART treatment regimens. Therefore, development of new broad spectrum antiretroviral drugs that produce minimal adverse effects remains an important therapeutic objective for the treatment of HIV/AIDS (Wainberg, 2000; Hertogs, 2000).

Recently, structure-based design of inhibitors maximizing interactions within the active site protease back-bone were described, as was the development of nonpeptide inhibitors (1-2) that have shown picomolar enzyme affinity and exceptional antiviral activity against both wild-type and drug-resistant HIV-1 strains (Ghosh, 1998; Koh, 2003; Ghosh, 2002; Surleraux, 2005; Yoshimura, 2002; Koh, 2003). The X-ray crystallographic studies revealed that backbone conformation of mutant protease is minimally distorted compared to wild-type HIV-1 proteases. Without being bound by theory, it is believed herein that maximizing 'back-bone binding' may be an important design strategy to combat drug-resistance (Ghosh, 2008). Inhibitor 1 (Daraunavir, TMC-114) was recently approved by the FDA for the treatment of drug resistant HIV strains (on Jun. 23, 2006, the FDA approved new HIV treatment for patients who do not respond to existing drugs). More recently, it has been approved for all HIV/AIDS patients including pediatric AIDS patients (On Oct. 21, 2008, FDA granted traditional approval to Prezista (darunavir), co-administered with ritonavir and with other antiretroviral agents, for the treatment of HIV-1 infection in treatment-experienced adult patients. In addition to the traditional approval, a new dosing regimen for treatment-naïve patients was approved).

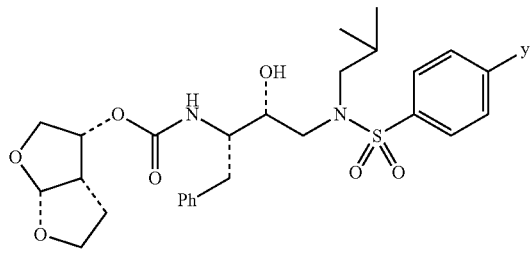

1 (Darunavir, y = NH$_2$)
($K_i$ = 16 pM; ID$_{50}$ = 1.6 nM)
1 (TMC-126, y = OMe)
($K_i$ = 14 pM; ID$_{50}$ = 1.2 nM)

Described herein are novel PIs with functionalities capable of interacting with the protein backbone as well as the introduction of flexible macrocycles involving P1'-P2'-ligands.

It has been discovered that protease inhibitors (PIs) containing functionalities that interact with the amino acid backbones of the catalytic site of HIV-1 protease along with a flexible macrocyclic group involving P1'-P2'-ligands are potent inhibitors and also show high activity in more relevant cell-based assays. In addition, it has been discovered herein the such compounds including a flexible macrocyclic group involving P1'-P2'-ligands for effective repacking of the altered PI-binding cavity of protease that emerges upon side chain mutations in PI-resistant HIV-1 variants are potent inhibitors of such otherwise resistant variants. Without being bound by theory, it is believed herein that the high activity of the compounds described herein may be due to the dual mode of action in both inhibiting the proteolytic activity of the protease, as well as in inhibiting the dimerization of the protease.

In one illustrative embodiment of the invention, a compound having the formula

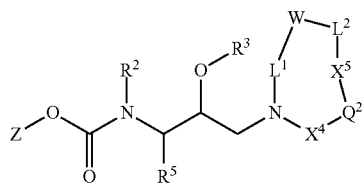

or a pharmaceutically acceptable salt, isomer, mixture of isomers, crystalline form, non crystalline form, hydrate, or solvate thereof is described, wherein $R^2$ and $R^3$ are in each instance independently selected from the group consisting of hydrogen and a prodrug forming group;

$R^5$ is alkyl, alkenyl, heteroalkyl, haloalkyl, cycloalkyl, heterocycloalkyl, aryl, arylalkyl, heteroaryl, or heteroarylalkyl, each of which is optionally substituted;

$X^4$ is carbonyl, S(O) or SO$_2$;

$X^5$ is a bond, oxygen, unsubstituted nitrogen, substituted nitrogen, sulfur, S(O) or sulfone;

$L^1$ and $L^2$ are independently selected in each instance from the group consisting of alkylene, cycloalkylene, unsaturated alkylene, heteroalkylene, cycloheteroalkylene, and unsaturated heteroalkylene, each of which is optionally substituted;

W is a bond, (H)C=C(H), oxygen, sulfur, S(O), SO$_2$, C(O), or optionally substituted nitrogen;

$Q^2$ is a divalent carbocycle, heterocycle, aryl, or heteroaryl, each of which is optionally substituted with one or more substituents; and Z is selected from the group consisting of monocyclic heterocycle, bicyclic heterocycle and tricyclic heterocycle, each of which is optionally substituted.

In another embodiment, the compound of any of the preceding embodiments wherein $L^1$ and $L^2$ are independently selected in each instance from the group consisting of alkylene, unsaturated alkylene, heteroalkylene, and unsaturated heteroalkylene, each of which is optionally substituted is described.

In another embodiment, the compound of any of the preceding embodiments wherein at least one of $L^1$ or $L^2$ is cycloalkylene or cycloheteroalkylene is described.

It is appreciated that the compounds described herein may be used alone or in combination with other compounds useful for treating such diseases, including those compounds that may operate by the same or different modes of action. Further, it is appreciated that the compounds and compositions described herein may be administered alone or with other compounds and compositions, such as other antiviral agents, immunomodulators, antibiotics, vaccines, and the like.

DETAILED DESCRIPTION

Figure 1:
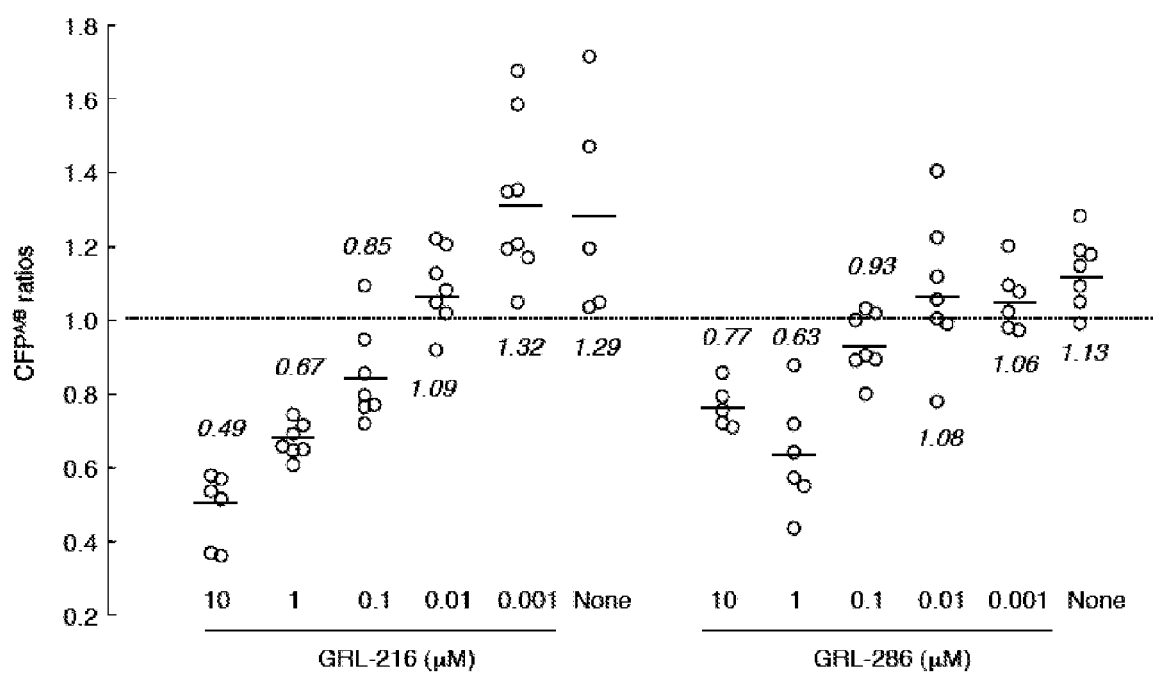
FIG. 1. GRL-216 (14c) and GRL-286 (14b) potently block the dimerization of HIV-1 protease. To examine whether GRL-216 and GRL-286 exerted inhibition of HIV-1 protease dimerization, the FRET-based HIV-1 expression system was employed (Koh, 2007). COS7 cells were transfected with pHIV-PR$_{WT\ CFP}$ and pHIV-PR$_{WT\ YFP}$ and exposed to various concentrations of either of the drugs and the CFP$_{A/B}$ 551 ratios were determined at the end of 72-hr culture. The average CFP$_{A/B}$ 552 ratios were all less than 1.0 in the presence of >0.1 μM GRL-216 and GRL-286, indicating that both compounds effectively blocked HIV-1 protease dimerization.

In one embodiment of the invention, a compound having the formula

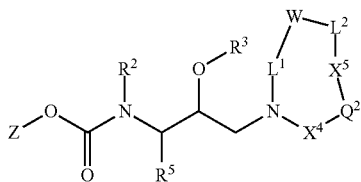

or a pharmaceutically acceptable salt, isomer, mixture of isomers, crystalline form, non crystalline form, hydrate, or solvate thereof is described wherein $R^2$ and $R^3$ are in each instance independently selected from the group consisting of hydrogen and a prodrug forming group;

$R^5$ is alkyl, alkenyl, heteroalkyl, haloalkyl, cycloalkyl, heterocycloalkyl, aryl, arylalkyl, heteroaryl, or heteroarylalkyl, each of which is optionally substituted;

$X^4$ is carbonyl, S(O) or $SO_2$;

$X^5$ is a bond, oxygen, unsubstituted nitrogen, substituted nitrogen, sulfur, S(O) or sulfone;

$L^1$ and $L^2$ are independently selected in each instance from the group consisting of alkylene, cycloalkylene, unsaturated alkylene, heteroalkylene, cycloheteroalkylene, and unsaturated heteroalkylene, each of which is optionally substituted;

W is a bond, (H)C=C(H), oxygen, sulfur, S(O), $SO_2$, C(O), or optionally substituted nitrogen;

$Q^2$ is a divalent carbocycle, heterocycle, aryl, or heteroaryl, each of which is optionally substituted with one or more substituents; and Z is selected from the group consisting of monocyclic heterocycle, bicyclic heterocycle and tricyclic heterocycle, each of which is optionally substituted.

In another embodiment, the compound of any of the preceding embodiments wherein $L^1$ and $L^2$ are independently selected in each instance from the group consisting of alkylene, unsaturated alkylene, heteroalkylene, and unsaturated heteroalkylene, each of which is optionally substituted is described.

In another embodiment, the compound of any of the preceding embodiments wherein $L^1$ is $CH_2(CH_2)_mCH_2$; and m is from 0 to about 4 is described.

In another embodiment, the compound of any of the preceding embodiments wherein $L^2$ is $CH_2(CH_2)_nCH_2$; and n is from 0 to about 4 is described.

In another embodiment, the compound of any of the preceding embodiments wherein W is a bond, (H)C=C(H), oxygen, sulfur, S(O), $S(O)_2$, or optionally substituted nitrogen is described.

In another embodiment, the compound of any of the preceding embodiments wherein $L^1$ is $CH_2(CH_2)_mCH_2$; $L^2$ is $CH_2(CH_2)_nCH_2$; W is a bond, (H)C=C(H), oxygen, sulfur, S(O), $S(O)_2$, or optionally substituted nitrogen; m is from 0 to about 4; and n is from 0 to about 4 is described.

In another embodiment, the compound of any of the preceding embodiments wherein $L^1$ is $CH_2CH_2CH_2CH_2$ is described.

In another embodiment, the compound of any of the preceding embodiments wherein $L^1$ is $CH_2$ is described.

In another embodiment, the compound of any of the preceding embodiments wherein m is 2; n is 0; and W is Z—(H)C=C(H) is described.

In another embodiment, the compound of any of the preceding embodiments wherein $X^5$ is oxygen; and W is a bond; and $L^1$ and $L^2$ are alkylene is described.

In another embodiment, the compound of any of the preceding embodiments wherein W is a bond; $L^1$ is $CH_2CH_2CH_2CH_2$; and $L^2$ is $CH_2CH_2CH_2$ is described.

In another embodiment, the compound of any of the preceding embodiments wherein $R^3$ is hydrogen is described.

In another embodiment, the compound of any of the preceding embodiments wherein at least one of $L^1$ or $L^2$ is cycloalkylene or cycloheteroalkylene is described.

In another embodiment, the compound of the preceding embodiment wherein $L^1$ is cycloheteroalkylene where the cyclic portion is a pyrrolidinone is described.

In another embodiment, the compound of any of the preceding embodiments wherein one of $L^1$ or $L^2$ is

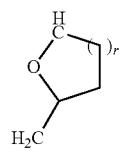

where r is 1 or 2

In another embodiment, the compound of any of the preceding embodiments wherein one of $L^1$ or $L^2$ is

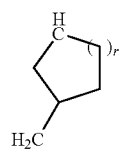

where r is 1 or 2

In another embodiment, the compound of any of the preceding embodiments wherein $L^1$ is

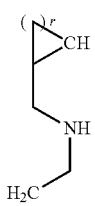

where r is 1, 2, 3, or 4 is described.

In another embodiment, the compound of any of the preceding embodiments wherein one of $L^1$ or $L^2$ is

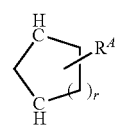

where r is 1 or 2; and $R^A$ is a carbonyl oxygen, hydroxyl, alkoxyl, amino, or heteroarylalkylamino is described.

In another embodiment, the compound of any of the preceding embodiments wherein $X^5$ is oxygen is described.

In another embodiment, the compound of any of the preceding embodiments wherein W is (H)C=C(H) is described.

In another embodiment, the compound of any of the preceding embodiments wherein $X^5$ is oxygen; and W is (H)C=C(H) is described.

In another embodiment, the compound of any of the preceding embodiments wherein $X^4$ is $S(O)_2$ is described.

In another embodiment, the compound of any of the preceding embodiments wherein $X^4$ is $SO_2$; and $X^5$ is oxygen In another embodiment, the compound of any of the preceding embodiments wherein $Y^2$ is methoxy is described.

In another embodiment, the compound of any of the preceding embodiments wherein Z is a bicycle heterocycle comprising at least one oxygen is described.

In another embodiment, the compound of any of the preceding embodiments wherein Z has the formula,

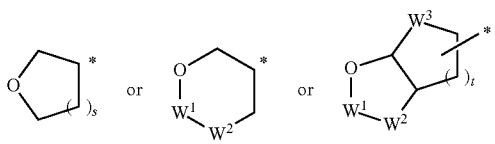

each of which is optionally substituted, wherein
* indicates the point of attachment; s is 0 to 2; t is 0 to 4;
$W^1$ is optionally substituted alkylene or optionally substituted nitrogen;
$W^2$ represents between 1 and 11 divalent radicals each independently selected from the group consisting of optionally substituted alkylene, oxygen, sulfur, optionally substituted nitrogen, and $SO_2$; and
$W^3$ is optionally substituted alkylene or oxygen is described.

In another embodiment, the compound of any of the preceding embodiments wherein Z has formula

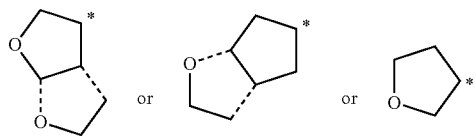

where * indicates the point of attachment is described.

In another embodiment, the compound of any of the preceding embodiments wherein $R^5$ is optionally substituted arylalkyl is described.

In another embodiment, the compound of any of the preceding embodiments wherein $R^5$ is optionally substituted benzyl is described.

In another embodiment, the compound of any of the preceding embodiments wherein $R^3$ is hydrogen is described.

In another embodiment, the compound of any of the preceding embodiments wherein $Q^2$ is optionally substituted with one or more substituents $Y^2$; wherein each substituent $Y^2$ is independently selected in each instance from the group consisting of hydroxy, halo, alkoxy, $C(O)R^8$, $C(O)NR^9R^{10}$, $C(O)OR^8$, $SR^8$, $S(O)R^7$, $S(O)_2R^7$, $NR^9R^{10}$, alkylene-$NR^9R^{10}$, or alkyl, heteroalkyl, haloalkyl, cycloalkyl, alkenyl, alkylene-$OR^8$, aryl, arylalkyl, heteroaryl and heteroarylalkyl, each of which is optionally substituted;
where $R^7$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted; $R^8$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted, or $R^8$ is hydrogen; and $R^9$ and $R^{10}$ are in each instance independently selected from hydrogen, or the group consisting of alkyl, alkenyl, heteroalkyl, haloalkyl, cycloalkyl, heterocycloalkyl, aryl, arylalkyl, heteroaryl, alkylsulfonyl, arylsulfonyl, and heteroarylalkyl, each of which is optionally substituted; or $R^9$ and $R^{10}$ and the attached nitrogen form an optionally substituted heterocycle is described.

In another embodiment, the compound of any of the preceding embodiments wherein $Q^2$ is 1,2-phenylene, optionally substituted with one or more $Y^2$ is described.

In another embodiment, the compound of any of the preceding embodiments wherein $Q^2$ is 1,2-phenylene substituted with at least one $Y^2$ is described.

In another embodiment, the compound of any of the preceding embodiments wherein $X^4$ is $SO_2$; $X^5$ is oxygen; and $Q^2$ is 4-methoxy-1,2-phenylene is described.

In another embodiment, the compound of any of the preceding embodiments wherein $Q^2$ is bicyclic is described.

In another embodiment, the compound of any of the preceding embodiments wherein $Q^2$ is a heterocycle of the formula

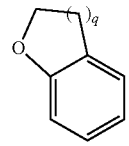

optionally substituted with one or more substituents $Y^2$, where q is 1 or 2 is described.

In another embodiment, a compound having the formula

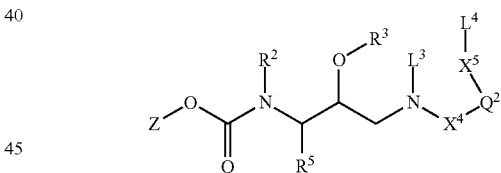

or a pharmaceutically acceptable salt, isomer, mixture of isomers, crystalline form, non crystalline form, hydrate, or solvate thereof is described wherein
$R^2$ and $R^3$ are in each instance independently selected from the group consisting of hydrogen and a prodrug forming group;
$R^5$ is alkyl, alkenyl, heteroalkyl, haloalkyl, cycloalkyl, heterocycloalkyl, aryl, arylalkyl, heteroaryl, or heteroarylalkyl, each of which is optionally substituted;
$X^4$ is carbonyl, S(O) or $SO_2$;
$X^5$ is a bond, oxygen, unsubstituted nitrogen, substituted nitrogen, sulfur, S(O) or sulfone;
$L^3$ and $L^4$ are independently selected in each instance from the group consisting of alkenyl, cycloalkenyl, heteroalkenyl, and cycloheteroalkenyl, each of which is optionally substituted, where both $L^3$ and $L^4$ terminate in a carbon-carbon double bond;
$Q^2$ is divalent carbocycle, heterocycle, aryl, or heteroaryl, each of which is optionally substituted with one or more substituents; and Z is selected from the group consisting of monocyclic heterocycle, bicyclic heterocycle and tricyclic heterocycle, each of which is optionally substituted.

In another embodiment, the compound of any of the preceding embodiments wherein $Q^2$ is substituted with a least one $Y^2$ wherein each substituent $Y^2$ is independently selected in each instance from the group consisting of hydroxy, halo, alkoxy, $C(O)R^8$, $C(O)NR^9R^{10}$, $C(O)OR^8$, $SR^8$, $S(O)R^7$, $S(O)_2R^7$, $NR^9R^{10}$, alkylene-$NR^9R^{10}$, or alkyl, heteroalkyl, haloalkyl, cycloalkyl, alkenyl, alkylene-$OR^8$, aryl, arylalkyl, heteroaryl and heteroarylalkyl, each of which is optionally substituted, where $R^7$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted;

$R^8$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted, or $R^8$ is hydrogen; and $R^9$ and $R^{10}$ are in each instance independently selected from hydrogen, or the group consisting of alkyl, alkenyl, heteroalkyl, haloalkyl, cycloalkyl, heterocycloalkyl, aryl, arylalkyl, heteroaryl, alkylsulfonyl, arylsulfonyl, and heteroarylalkyl, each of which is optionally substituted; or $R^9$ and $R^{10}$ and the attached nitrogen form an optionally substituted heterocycle;

In another embodiment, a pharmaceutical composition comprising the compound of any of the preceding embodiments in a therapeutically effective amount for treating HIV infection, and one or more of a carrier, diluent, excipient therefor, or a combination thereof is described.

In another embodiment, a method for treating a patient in need of relief from HIV/AIDS disease, the method comprising the step of administering to the patient a therapeutically effective amount of the composition of any one of the preceding embodiments, or a composition comprising the compound of any one of the preceding embodiments is described.

In another embodiment, the method or composition of any of the preceding embodiments wherein the HIV/AIDS disease includes at least one resistant HIV protease is described.

In another embodiment, the method or composition of any of the preceding embodiments wherein the HIV/AIDS disease is resistant to at least one of saquinavir, ritonavir, nelfinavir, lopinavir or atazanavir is described.

In another embodiment, the method or composition of any of the preceding embodiments wherein the HIV/AIDS disease includes at least one multi-PI-resistant clinical HIV-1 variant is described.

In another embodiment, the compound having the formula

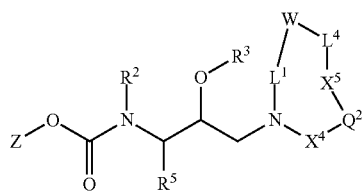

or a pharmaceutically acceptable salt, isomer, mixture of isomers, crystalline form, non crystalline form, hydrate, or solvate thereof is described; wherein $R^2$ and $R^3$ are in each instance independently selected from the group consisting of hydrogen and a prodrug forming group;

$R^5$ is alkyl, alkenyl, heteroalkyl, haloalkyl, cycloalkyl, heterocycloalkyl, aryl, arylalkyl, heteroaryl, or heteroarylalkyl, each of which is optionally substituted;

$X^4$ is carbonyl, S(O) or $SO_2$;

$X^5$ is a bond, oxygen, unsubstituted nitrogen, substituted nitrogen, sulfur, S(O) or sulfone;

$L^1$ and $L^2$ are independently selected in each instance from the group consisting of alkylene, unsaturated alkylene, heteroalkylene, and unsaturated heteroalkylene, each of which is optionally substituted;

W is a bond, (H)C=C(H), oxygen, sulfur, S(O), $SO_2$, C(O), or optionally substituted nitrogen;

$Q^2$ is divalent carbocycle, heterocycle, aryl, or heteroaryl, each of which is optionally substituted with one or more substituents $Y^2$; wherein each substituent $Y^2$ is independently selected in each instance from the group consisting of hydroxy, halo, alkoxy, $C(O)R^8$, $C(O)NR^9R^{10}$, $C(O)OR^8$, $SR^8$, $S(O)R^7$, $S(O)_2R^7$, $NR^9R^{10}$, alkylene-$NR^9R^{10}$, or alkyl, heteroalkyl, haloalkyl, cycloalkyl, alkenyl, alkylene-$OR^8$, aryl, arylalkyl, heteroaryl and heteroarylalkyl, each of which is optionally substituted;

where $R^7$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted; $R^8$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted, or $R^8$ is hydrogen; and $R^9$ and $R^{10}$ are in each instance independently selected from hydrogen, or the group consisting of alkyl, alkenyl, heteroalkyl, haloalkyl, cycloalkyl, heterocycloalkyl, aryl, arylalkyl, heteroaryl, alkylsulfonyl, arylsulfonyl, and heteroarylalkyl, each of which is optionally substituted; or $R^9$ and $R^{10}$ and the attached nitrogen form an optionally substituted heterocycle; and Z is selected from the group consisting of monocyclic heterocycle, bicyclic heterocycle and tricyclic heterocycle, each of which is optionally substituted.

In another embodiment, the compound of the preceding embodiment wherein $L^1$ is $CH_2(CH_2)_mCH_2$; $L^2$ is $CH_2(CH_2)_nCH_2$; W is a bond, (H)C=C(H), oxygen, sulfur, S(O), $S(O)_2$, or optionally substituted nitrogen; m is from 0 to about 4; and n is from 0 to about 4 is described. In another embodiment, the compound of the preceding embodiment wherein $L^1$ is $CH_2CH_2CH_2CH_2$ or $CH_2$ is described.

In another embodiment, the compound of any one of the preceding embodiments wherein $X^5$ is oxygen; and W is (H)C=C(H) is described. In another embodiment, any of the preceding compounds wherein W is Z—(H)C=C(H) is described.

In another embodiment, the compound of any of the preceding embodiments wherein m is 2; n is 0; and W is Z—(H)C=C(H) is described.

In another embodiment, the compound of any of the preceding embodiments wherein $X^5$ is oxygen; and W is a bond; and $L^1$ and $L^2$ are alkylene is described. In another embodiment, the compound of any of the preceding embodiments wherein W is a bond; $L^1$ is $CH_2CH_2CH_2CH_2$; and $L^2$ is $CH_2CH_2CH_2$ is described.

In another embodiment, the compound of formula

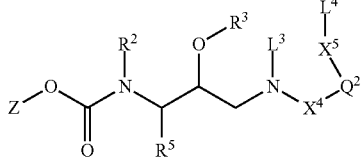

or a pharmaceutically acceptable salt, isomer, mixture of isomers, crystalline form, non crystalline form, hydrate, or solvate thereof is described; wherein $R^2$ and $R^3$ are in each instance independently selected from the group consisting of hydrogen and a prodrug forming group;

$R^5$ is alkyl, alkenyl, heteroalkyl, haloalkyl, cycloalkyl, heterocycloalkyl, aryl, arylalkyl, heteroaryl, or heteroarylalkyl, each of which is optionally substituted;

$X^4$ is carbonyl, S(O) or $SO_2$;

$X^5$ is a bond, oxygen, unsubstituted nitrogen, substituted nitrogen, sulfur, S(O) or sulfone;

$L^3$ and $L^4$ are independently selected in each instance from the group consisting of unsaturated alkenyl, and heteroalkenyl, each of which is optionally substituted;

$Q^2$ is divalent carbocycle, heterocycle, aryl, or heteroaryl, each of which is optionally substituted with one or more substituents $Y^2$;

wherein each substituent $Y^2$ is independently selected in each instance from the group consisting of hydroxy, halo, alkoxy, $C(O)R^8$, $C(O)NR^9R^{10}$, $C(O)OR^8$, $SR^8$, $S(O)R^7$, $S(O)_2R^7$, $NR^9R^{10}$, alkylene-$NR^9R^{10}$, or alkyl, heteroalkyl, haloalkyl, cycloalkyl, alkenyl, alkylene-$OR^8$, aryl, arylalkyl, heteroaryl and heteroarylalkyl, each of which is optionally substituted, where $R^7$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted;

$R^8$ is in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted, or $R^8$ is hydrogen; and $R^9$ and $R^{10}$ are in each instance independently selected from hydrogen, or the group consisting of alkyl, alkenyl, heteroalkyl, haloalkyl, cycloalkyl, heterocycloalkyl, aryl, arylalkyl, heteroaryl, alkylsulfonyl, arylsulfonyl, and heteroarylalkyl, each of which is optionally substituted; or $R^9$ and $R^{10}$ and the attached nitrogen form an optionally substituted heterocycle;

Z is selected from the group consisting of monocyclic heterocycle, bicyclic heterocycle and tricyclic heterocycle, each of which is optionally substituted. In another embodiment, the compound of any of the preceding embodiments wherein Z is a bicycle heterocycle comprising at least one oxygen is described.

In another embodiment, the compound of any of the preceding embodiments wherein Z has the formula,

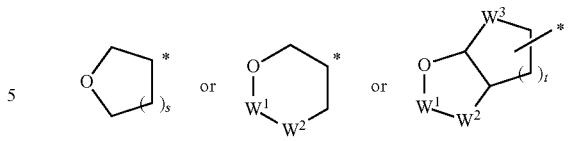

each of which is optionally substituted is described, wherein

* indicates the point of attachment; s is 0 to 2; t is 0 to 4;

$W^1$ is optionally substituted alkylene or optionally substituted nitrogen;

$W^2$ represents between 1 and 11 divalent radicals each independently selected from the group consisting of optionally substituted alkylene, oxygen, sulfur, optionally substituted nitrogen, and $SO_2$; and $W^3$ is optionally substituted alkylene or oxygen.

In another embodiment, the compound of any of the preceding embodiments wherein Z has formula

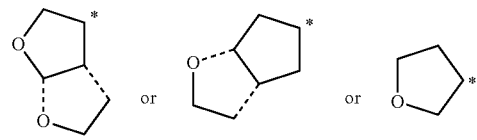

where * indicates the point of attachment is described. In another embodiment, the compound of any of the preceding embodiments wherein Z has the formula

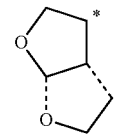

where * indicates the point of attachment, is described. In another embodiment, the compound of the preceding embodiment wherein m is 2; n is 0; and W is Z—(H)C═C(H) is described.

The compound of any one of the preceding embodiments wherein $R^5$ is optionally substituted arylalkyl.

In another embodiment, the compound of any of the preceding embodiments wherein $Q^2$ is 1,2-phenylene, optionally substituted with one or more $Y^2$, where $Y^2$ is as defined above is described. In another embodiment, the compound of any of the preceding embodiments wherein $X^4$ is $SO_2$; $X^5$ is oxygen; $Q^2$ is 1,2-phenylene; and $Y^2$ is 4-methoxy is described. In another embodiment, the compound of any of the preceding embodiments wherein $R^5$ is benzyl is described.

In another embodiment, also described herein are pharmaceutical compositions containing one or more of the compounds described herein. In one aspect, the compositions include a therapeutically effective amount of the one or more compounds for treating a patient with HIV/AIDS. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with HIV/AIDS are also described herein. In one aspect, the methods include the step of administering one or more of the compounds and/or compositions described herein to a patient with HIV/AIDS. In another aspect, the methods include administering a therapeutically effective amount of the one or more compounds and/or compositions described herein for treating patients with HIV/AIDS. In another embodiment, uses of the compounds and compositions in the manufacture of a medicament for treating patients with HIV/AIDS are also described herein. In one aspect, the medicaments include a therapeutically effective amount of the one or more compounds and/or compositions for treating a patient with HIV/AIDS.

It is appreciated herein that the compounds described herein may be used alone or in combination with other compounds useful for treating HIV/AIDS, including those compounds that may be therapeutically effective by the same or different modes of action. In addition, it is appreciated herein that the compounds described herein may be used in combination with other compounds that are administered to treat other symptoms of HIV/AIDS, such as compounds administered to treat bacterial, fungal, and protozoic infections, and the like. In another embodiment, a pharmaceutical composition comprising the compound of any one of the preceding claims in a therapeutically effective amount for treating HIV/AIDS disease, and one or more of a carrier, diluent, excipient therefor, or a combination thereof is described.

In another embodiment, a method of treating a patient in need of relief from HIV infection, the method comprising the step of administering to the patient a therapeutically effective amount of the composition of any one of the preceding embodiments, or a composition comprising the compound of any one of the preceding embodiments is described.

The synthesis of sulfonyl chlorides 7a-d is shown in Scheme 1. A Mitsunobu-type reaction between 3-methoxyphenol and alcohols 4a-d in the presence of triphenylphosphine and diisopropyl azodicarboxylate (DIAD) afforded ethers 5a-d. (Mitsunobu, 1981). Electrophilic aromatic substitution of ethers 5a-d with acetic anhydride and concentrated sulfuric acid in methanol furnished a mixture of sulfonic acid regioisomers 6a-d and 6e-h in a 1:1 ratio that were separated by flash chromatography. Structural confirmation of the isomers was determined by extensive 2D NMR experiments (NOESY and HMBC). Conversion to the sulfonyl chlorides 7a-d was achieved by reaction of the sulfonic acids 6a-d with thionyl chloride in the presence of pyridine. It is appreciated that other compounds of the invention can be prepared using modifications well-known to the person having ordinary skill in the art of organic synthesis of schemes described herein.

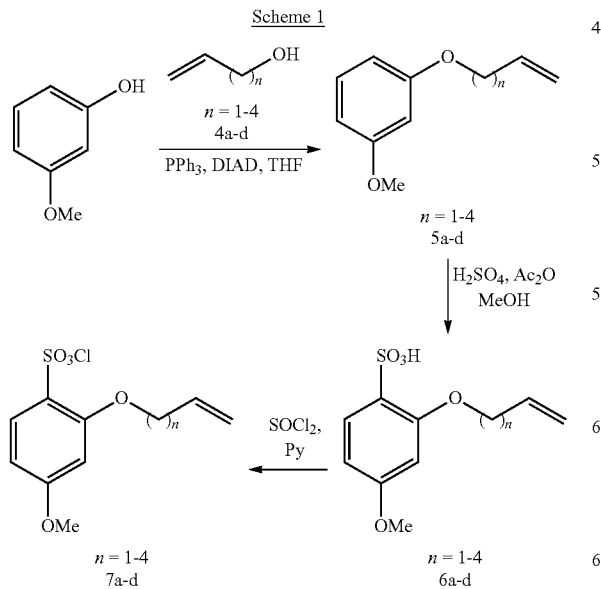

In one embodiment, compounds 13a-h are synthesized as outlined in Scheme 2. Nucleophilic attack of amines 9a and 9b on commercially available epoxide 8 in the presence of isopropanol gave hydroxy amines 10a and 10b. The conversion of amines 10a and 10b to the sulfonamides 11a-h was realized by coupling with sulfonyl chlorides 5a-d in the presence of pyridine. Removal of the Boc protecting group from sulfonamides 11a-h using 30% trifluoroacetic acid in $CH_2Cl_2$ furnished the corresponding amines, which were then coupled with activated bis-THF (12) to give acyclic inhibitors 13a-h (Ghosh, 2006).

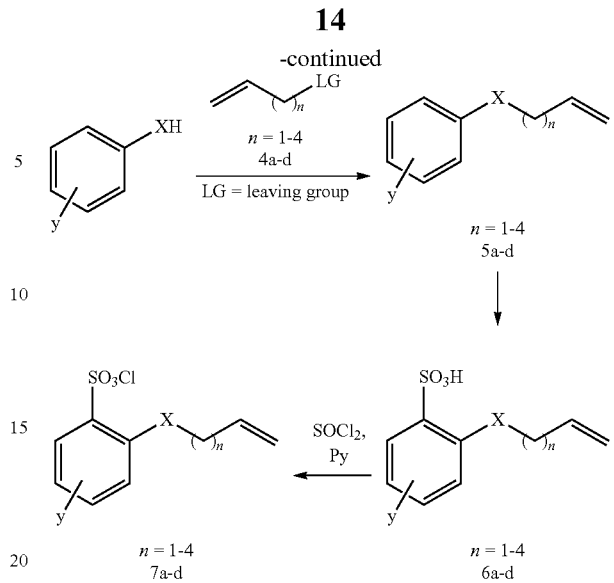

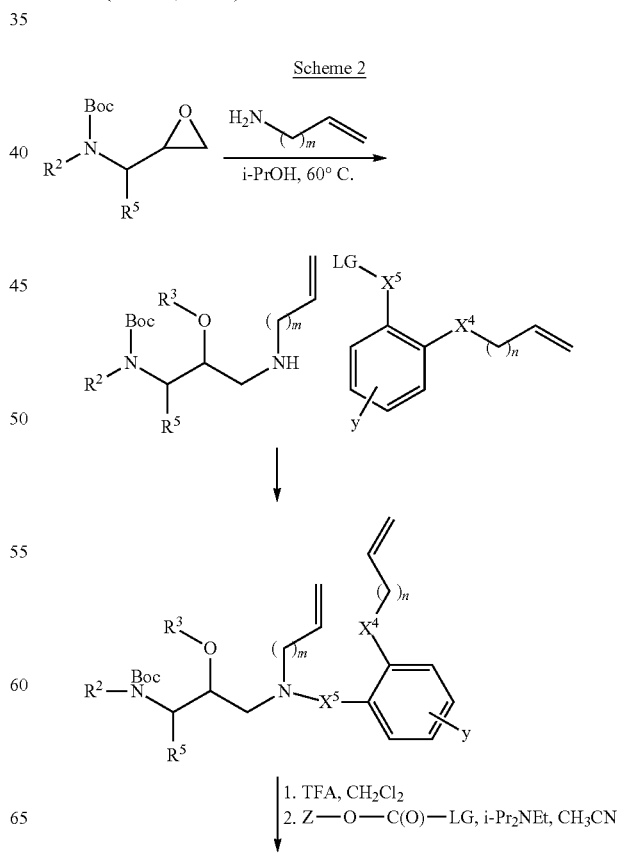

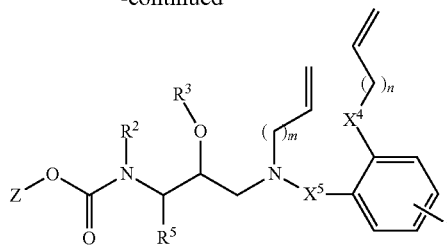

In another embodiment, the acyclic compounds 13a-h thus obtained were exposed to ring closing metathesis using Grubbs' 1st or 2nd generation catalyst (Scheme 3) to give the unsaturated macrocyclic inhibitors 14a-h (Schwab, 1995; Scholl, 1999). Larger ring sizes (15-13) gave a mixture of E/Z isomers, while in the case of smaller rings (12-9) the Z isomer was obtained almost exclusively. The E and Z isomers were isolated using reversed-phase HPLC and the stereochemistry established by 2-D NMR (COSY and NOESY) experiments allowing their individual biological characterization. In a further embodiment, the unsaturated compounds were subsequently reduced using hydrogen and 10% Pd—C as a catalyst yielding inhibitors 15a-g.

(Scheme 4). The conversion of amines 17a-c to the sulfonamides 18a-c was realized by coupling with sulfonyl chlorides 7d in the presence of pyridine. Removal of the Boc protecting group from sulfonamides 18a-c using 30% trifluoroacetic acid in $CH_2Cl_2$ furnished the corresponding amines, which were then coupled with activated bis-THF (12) to give acyclic inhibitors 19a-c (Ghosh, 2006). A ring closing metathesis reaction using Grubbs' 2nd generation catalyst (Scheme 5) provided unsaturated macrocyclic inhibitors 20a-c and 21a-c, which were separated into their E/Z isomers by reversed-phase HPLC and identified by 2-D NMR (COSY and NOESY) (Schwab, 1999). The unsaturated compounds 20a-c and 21a-c were subsequently reduced using hydrogen and 10% Pd—C as a catalyst yielding inhibitors 22a-c.

Scheme 3

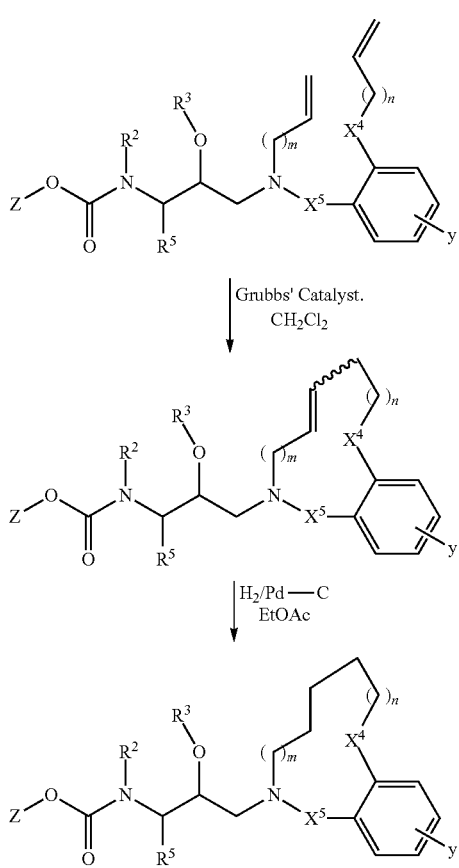

A series of methylated inhibitors were prepared in a similar fashion. Nucleophilic attack of amines 16a-c on commercially available epoxide 8 gave hydroxy amines 17a-c Scheme 4

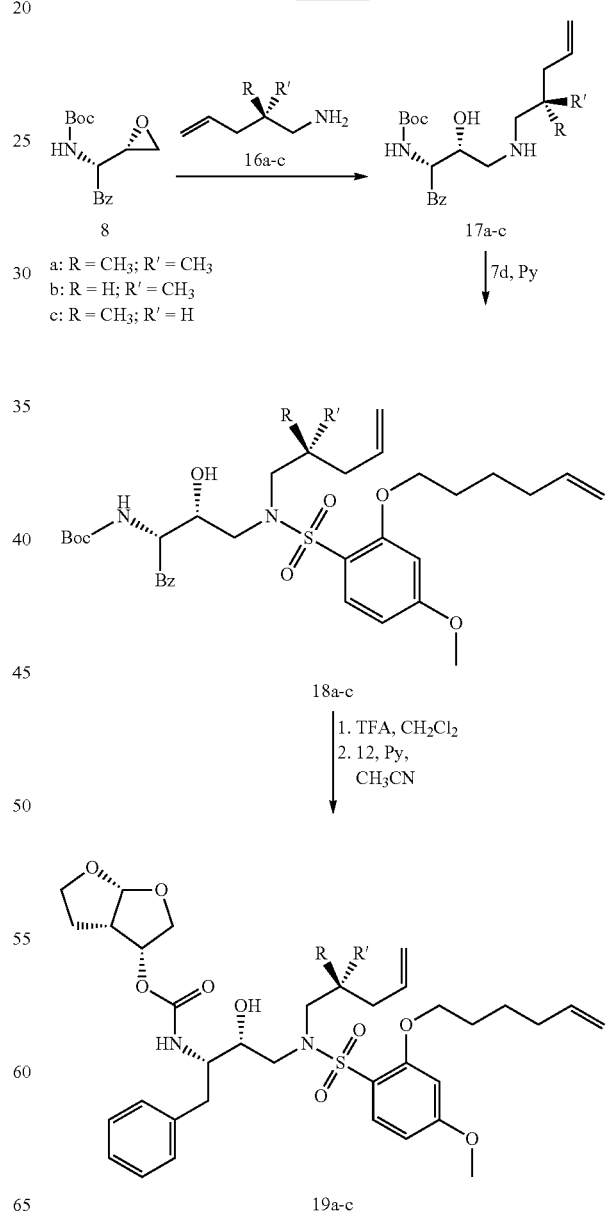

Scheme 5

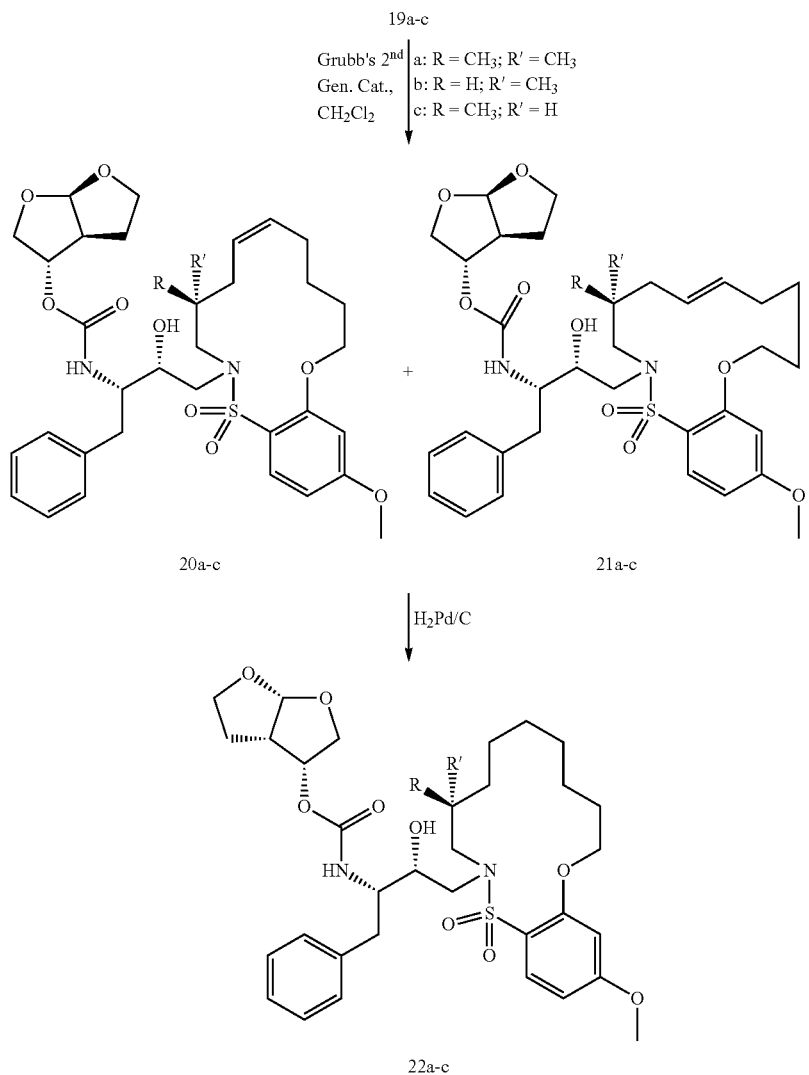

Inhibitors with longer carbon chains resulted in lower enzyme inhibitory activity. Extension of the β hydroxyl amine chain by three methylene groups resulted in a 10 fold loss in activity (13a $K_i$=16 nM versus 13e $K_i$=1.7 nM). Similarly, extension of the ether carbon chain by three methylene groups resulted in a 17 fold loss in activity (13h $K_i$=0.10 nM versus 13e $K_i$=1.7 nM).

For example, the 14 membered macrocyclic inhibitors 14b and 15b have $K_i$ values less than 0.7 nM and $IC_{50}$ values less than 49 nM whereas their corresponding acyclic inhibitor 13b had a $K_i$ of 11 nM and $IC_{50}$ value of >1000 nM (greater than 15-fold and 20-fold change, respectively). Without being bound by theory, Another trend observed is a preference of the S2' subsite for macrocyclic rings of size 10 and 13. Indeed, the most potent compound of the series, inhibitor 14c incorporating a 13 membered ring, showed a $K_i$ of 45 pm and $IC_{50}$ of 2 nm. Increasing the ring size to 14 or 15 as well as decreasing the ring to 12 or 11 resulted in reduced enzymatic inhibitory and antiviral activity. Similarly, inhibitors incorporating a 10-membered ring (14g and 15f) were also very potent (14g $K_i$=51 pm; 15f $K_i$=86 pm and $IC_{50}$=5.5 nm).

The improvement in the $K_i$ and $IC_{50}$ values for the unsaturated cyclic inhibitors 14a-h compared to their saturated analogs 15a-g is described. For the 13-membered ring series, the presence of a double bond results in a 10-fold increase in both $K_i$ and $IC_{50}$ (14c $K_i$=45 pM and $IC_{50}$=2 nM compared to 15c $K_i$=470 pM and $IC_{50}$=22 nM). Similar differences in potency are observed for the 11, 14, and 15-membered macrocycles although for the smaller rings 9, 10, and 12 the effect is less pronounced. Without being bound by theory, it is believed that this may result from a restricted conformation in the molecule that results from the presence of the double bond and leads to a better fit in the hydrophobic pocket of the S2 sub-site. The importance of the stereochemistry of the double bond in the olefinic compounds is described. As shown in Table 3, only minor variations in activity (less than 5 fold) were observed between the E and Z isomers of the 13, 14, and 15-membered. For the 13-membered ring system the Z isomer was favored over the E configuration.

In another embodiment, possible substitutions that can be made across the macrocylic ring system that further enhance biological activity are described. Without being bound by theory, it is believed that a single methyl substitution to the macrocylic amine atom could fill a hydrophobic pocket filled by a methyl group of darunavir's isopropyl moiety. The design and synthesis of a series of mono and dimethylated 14-membered macrocylic ring systems and evaluation of the impact of this substitution on the biological activity is described. Geminal dimethyls at this location (19a through 22a) decreased (10-fold) enzyme inhibition and reduced antiviral activity. Addition of a single methyl group to the ring reduced biological activity as compared to 14b and 15b, although results varied depending upon the stereochemistry of the ring systems. 20c and 21b were the most potent compounds from this series with $K_i$=0.31 and 2.8 nM and $IC_{50}$=9.0 and 6.3 nM, respectively.

In another embodiment, compounds of formulae

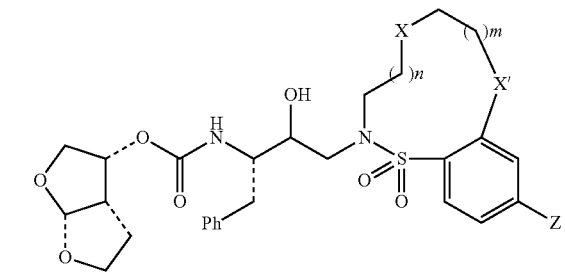

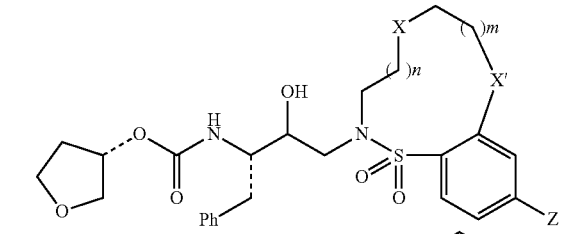

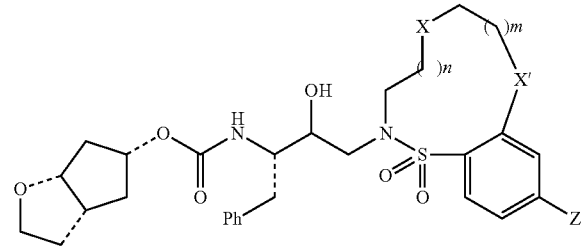

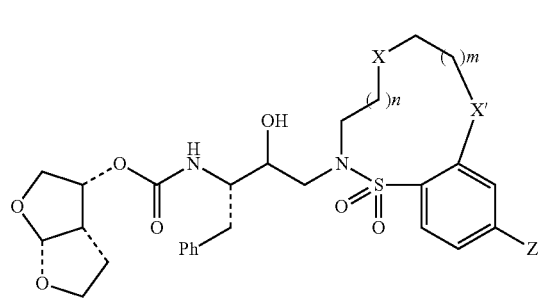

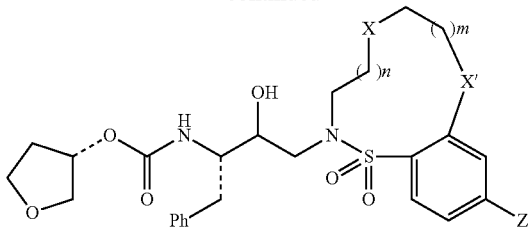

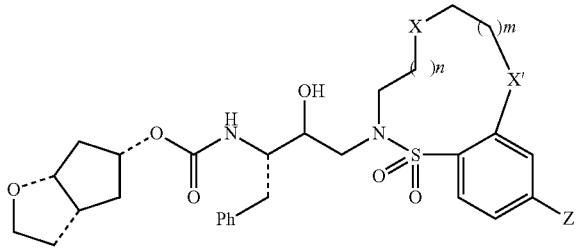

m is 0-4; n is 0-4;
X=O, S, SO$_2$, NR, CHR, CR$_2$;
X'=O, S, SO$_2$, NR, CHR, CR$_2$;
Z=SO$_2$R, NR$_2$, CHROR, CR$_3$; where
where R is independently H, alkyl, heteroalkyl, alkylheterocycle m is 0-4; n is 0-4;
X=O, S, SO$_2$, NR, CHR, CR$_2$;
X'=O, S, SO$_2$, NR, CHR, CR$_2$;
Z=SO$_2$R, NR$_2$, CHROR, CR$_3$, OR; where
where R is independently H, alkyl, heteroalkyl, alkylheterocycle are described.

In another embodiment, compounds of formulae

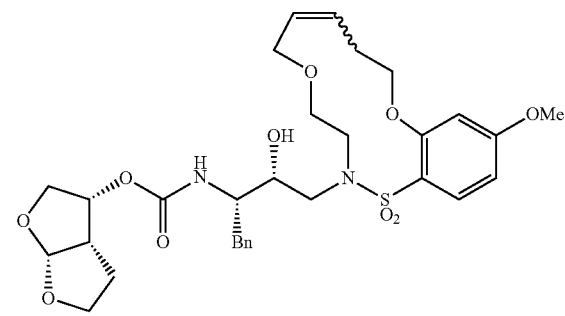

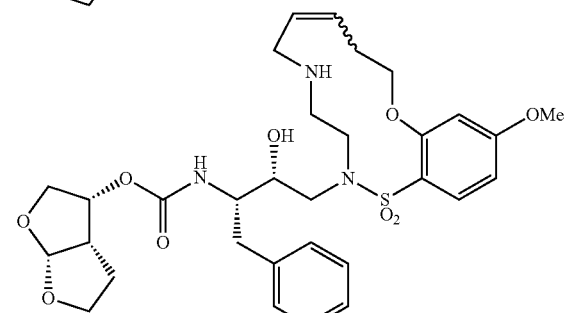

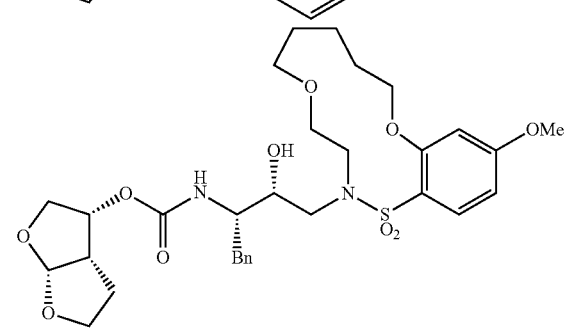

-continued
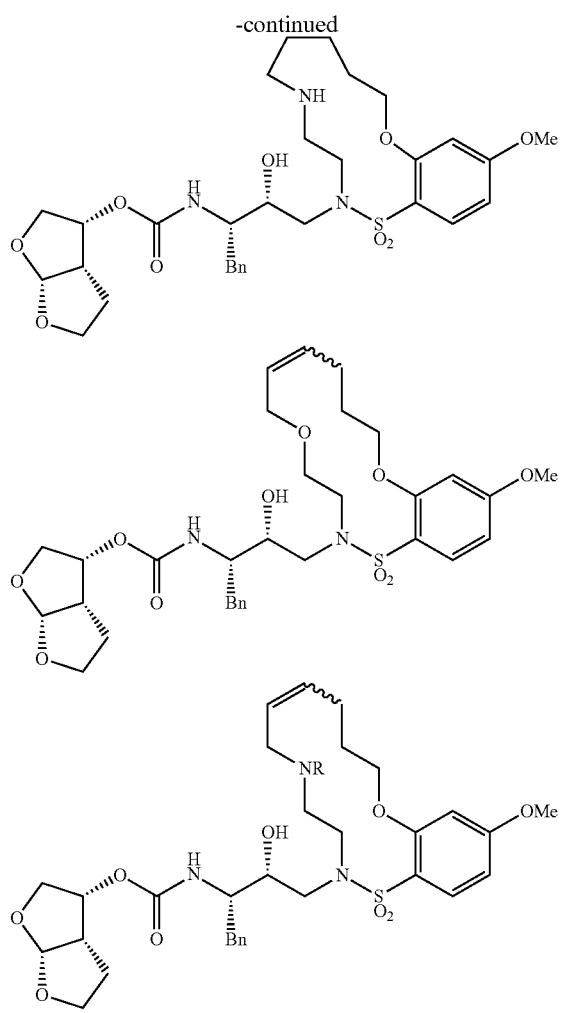
R = H, CH₃, SO₂CH₃, and the like.
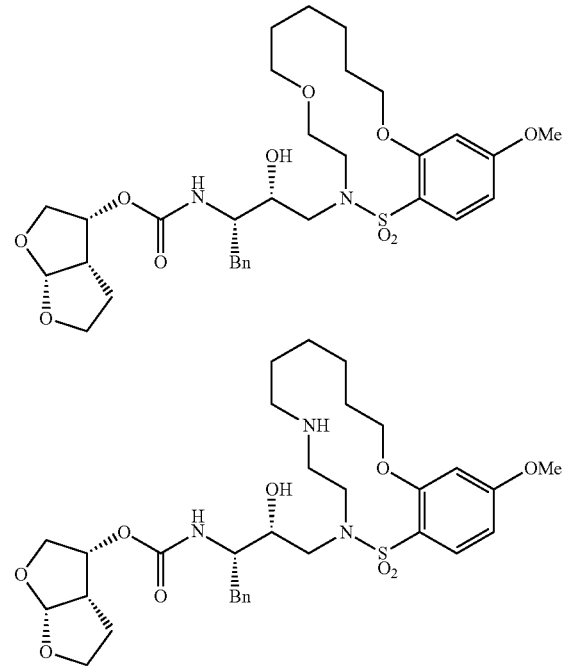
In another embodiment, compounds of formulae
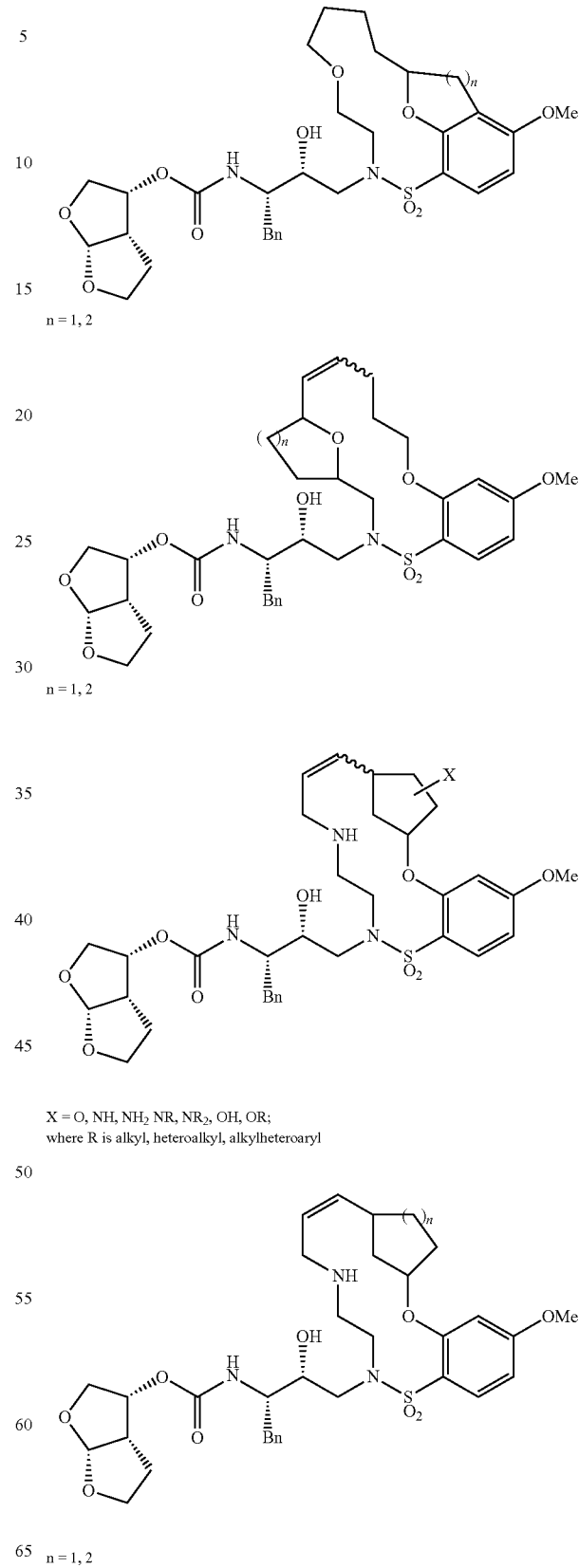
n = 1, 2
n = 1, 2
X = O, NH, NH₂ NR, NR₂, OH, OR;
where R is alkyl, heteroalkyl, alkylheteroaryl
n = 1, 2
are described.

-continued

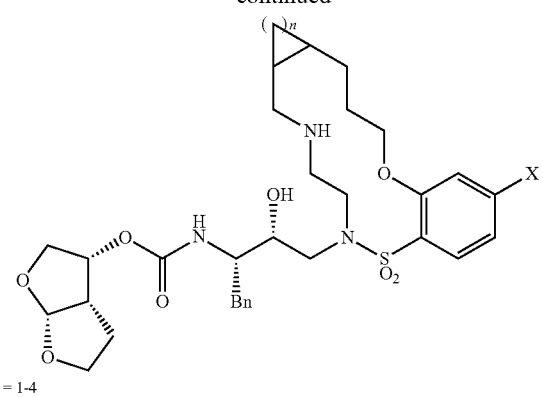

n = 1-4

X = NH$_2$, CH$_2$OR, OCH$_3$, and the like;
where R is H, alkyl, heteroalkyl, alkylheteroaryl are described.

While certain embodiments of the present invention have been described and/or exemplified above, it is contemplated that considerable variation and modification thereof are possible. Accordingly, the present invention is not limited to the particular embodiments described and/or exemplified herein.

The compounds described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The compounds described herein may be capable of existing as geometric isomers. Accordingly, it is to be understood that the present invention includes pure geometric isomers or mixtures of geometric isomers.

It is appreciated that the compounds described herein may exist in unsolvated forms as well as solvated forms, including hydrated forms. In general, the solvated forms are equivalent to unsolvated forms and are encompassed within the scope of the present invention. The compounds of the present invention may exist in multiple crystalline or amorphous forms. In general, all physical forms are equivalent for the uses contemplated by the present invention and are intended to be within the scope of the present invention.

It is also appreciated that in the foregoing embodiments, certain aspects of the compounds are presented in the alternative, such as selections for any one or more of Z, Q$^2$, X$^4$, X$^5$, L$^1$, L$^2$, L$^3$, L$^4$, W, R$^2$, R$^3$, R$^4$, R$^5$, R$^6$, R$^7$, R$^8$, R$^9$, R$^{10}$, Y$^2$, n, m, s, and t. It is therefore to be understood that various alternate embodiments of the invention include individual members of those lists, as well as the various subsets of those lists. Each of those combinations is to be understood to be described herein by way of the lists.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including C$_1$-C$_{24}$, C$_1$-C$_{12}$, C$_1$-C$_8$, C$_1$-C$_6$, and C$_1$-C$_4$. It is to be further understood that alkenyl and/or alkynyl may each be advantageously of limited length, including C$_2$-C$_{24}$, C$_2$-C$_{12}$, C$_2$-C$_8$, C$_2$-C$_6$, and C$_2$-C$_4$. It is appreciated herein that shorter alkyl, alkenyl, and/or alkynyl groups may add less lipophilicity to the compound and accordingly will have different pharmacokinetic behavior.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including C$_3$-C$_{24}$, C$_3$-C$_{12}$, C$_3$-C$_8$, C$_3$-C$_6$, and C$_5$-C$_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, alkylene includes bivalent hydrocarbon groups wherein the hydrocarbon group may be a straight-chained or a branched-chain hydrocarbon group. Non-limiting illustrative examples include methylene, 1,2-ethylene, 1-methyl-1,2-ethylene, 1,4-butylene, 2,3-dimethyl-1,4-butylene, 2-methyl-2-ethyl-1,5-pentylene, and the like.

As used herein, the term "cycloalkylene" includes a bivalent chain of carbon atoms, which is optionally branched, where at least a portion of the chain in cyclic. It is to be understood that alkylcycloalkylalkyl is a subset of cycloalkylene. It is to be understood that cycloalkylene may be polycyclic.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "heteroalkylene" includes an alkylene group wherein one or more carbon atoms are replaced with a heteroatom selected from oxygen, sulfur or optionally substituted nitrogen.

As used herein, the term "cycloheteroalkylene" includes a bivalent chain of atoms that includes both carbon and at least one heteroatom, such as heteroalkylene, and is optionally branched, where at least a portion of the chain is cyclic. Illustrative heteroatoms include nitrogen, oxygen, and sulfur. It is to be understood that heteroatoms may be included in the cyclic portion, the non-cyclic portion, or in both the cyclic and non-cyclic portions of the cycloheteroalkylene.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acyclethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted. The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk, 2000. It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustrative routes of oral administration include tablets, capsules, elixirs, syrups, and the like.

In another embodiment, the compounds described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

General Experimental Methods. Chemicals and reagents were purchased from commercial suppliers and used without further purification. Anhydrous solvents were obtained as follows: pyridine and dichloromethane were distilled from calcium hydride; tetrahydrofuran and diethyl ether were distilled from sodium wire with benzophenone as an indicator. All other solvents were reagent grade. All moisture sensitive reactions were carried out in oven dried glassware under argon. $^1$H NMR and $^{13}$C NMR spectra were recorded on a Bruker Avance ARX-400, Bruker DRX-500, or Bruker Avance-III-800 spectrometer. Chemical shifts are given in ppm and are referenced against the diluting solvent. For chloroform-d: $^{13}$C triplet=77.00 CDCl$_3$ and $^1$H singlet=7.26 ppm. For methanol-d$_4$: $^{13}$C septuplet=49.05 and $^1$H quintuplet=3.31 ppm. Characteristic splitting patterns due to spin spin coupling are expressed as follows: br=broad, s=singlet, d=doublet, t=triplet, q=quartet, m=multiplet, sept=septuplet. All coupling constants are measured in hertz. FTIR spectra were recorded on a Mattson Genesis II FT-IR spectrometer or a Perkin Elmer spectrometer #L1185247 using a NaCl plate or KBr pellot. Optical rotations were recorded on a Perkin Elmer 341 or Rudolph Research Autopol III polarimeter. Low resolution mass spectra were recorded on a FinniganMAT LCQ or Hewlett-Packard Engine mass spectrometer. High resolution mass spectra were recorded on a FinniganMAT XL95 mass spectrometer calibrated against PPG. Column chromatography was performed with Whatman 240-400 mesh silica gel under low pressure of 3-5 psi. TLC was carried out with E. Merck silica gel 60-F-254 plates. Visualization was carried out with short-wave UV or staining with phosphomolybdic acid (PMA), iodine, or ninhydrin. HPLC data was collected using a system composed of an Agilent 1100 series degasser, quaternary pump, thermostatable column compartment, variable wavelength detector, and Agilent 1200 series autosampler and fraction collector controlled by Chemstation software. All chromatographic reagents used were HPLC grade. The reported inhibitors were found to be >95% pure by reversed-phase gradient HPLC (see supporting information for specific method conditions).

Example 1

1-(Hex-5-enyloxy)-3-methoxybenzene (5a): To a stirred solution of 3-methoxy phenol (1.24 g, 10 mmol), 5-hexen-1-ol, 4a (1.4 mL, 12 mmol) and Ph$_3$P (3.14 g, 12 mmol) in THF (20 mL) at 0° C. was added diisopropylazodicarboxylate (2.3 mL, 12 mmol) dropwise. After stirring the solution for 30 min at 0° C. the reaction mixture was warmed to 23° C. and stirred for 3 h. The reaction mixture was concentrated in vacuo and the residue was subjected to column chromatography (98:2 hexanes:EtOAc) to yield 1.98 g of 5a (96% yield) as a colorless oil. $^1$H NMR (400 MHz, CDCl$_3$): δ 1.58-1.66 (m, 2H), 1.80-1.88 (m, 2H), 2.15-2.20 (m, 2H), 3.82 (s, 3H), 3.98 (t, J=6.4 Hz, 2H), 5.02-5.12 (m, 2H), 5.83-5.92 (m, 1H), 6.52-6.56 (m, 3H), 7.19-7.24 (m, 1H); $^{13}$C NMR (100 MHz, CDCl$_3$): δ 25.3, 28.7, 33.4, 55.1, 67.6, 100.9, 106.0, 106.6, 114.7, 129.8, 138.5, 160.3, 160.8; FT-IR (film, NaCl) $v_{max}$=3075, 2939, 1599, 1493, 1287, 1200, 1152, 1046 cm$^{-1}$; CI LRMS m/z (ion): 207.25 (M+H)$^+$.

Example 2

1-Methoxy-3-(pent-4-enyloxy)benzene (5b): Title compound was obtained from 4-penten-1-ol 4b, as described for 5a in 95% yield after flash-chromatography (98:2 hexanes: EtOAc) as a colorless oil. $^1$H NMR (400 MHz, CDCl$_3$): δ 1.88-1.94 (m, 2H), 2.25-2.30 (m, 2H), 3.81 (s, 3H), 3.98 (t, J=6.4 Hz, 2H), 5.03-5.13 (m, 2H), 5.85-5.95 (m, 1H), 6.51-6.56 (m, 3H), 7.20 (t, J=8.1 Hz, 1H); $^{13}$C NMR (100 MHz, CDCl$_3$): δ 28.3, 30.0, 55.1, 67.0, 100.9, 106.0, 106.6, 115.1, 129.7, 137.7, 160.2, 160.7; FT-IR (film, NaCl) $v_{max}$=3076, 2940, 1599, 1492, 1287, 1200, 1152, 1048 cm$^{-1}$; CI LRMS m/z (ion): 193.25 (M+H)$^+$.

Example 3

1-(But-3-enyloxy)-3-methoxybenzene (5c): Title compound was obtained from 3-buten-1-ol 4c, as described for 5a in 96% yield after flash-chromatography (98:2 hexanes:EtOAc) as a colorless oil. $^1$H NMR (400 MHz, CDCl$_3$): δ 2.54-2.60 (m, 2H), 3.81 (s, 3H), 4.02 (t, J=6.7 Hz, 2H), 5.13-5.23 (m, 2H), 5.89-5.97 (m, 1H), 6.51-6.56 (m, 3H), 7.20 (t, J=8.1 Hz, 1H); $^{13}$C NMR (100 MHz, CDCl$_3$): δ 33.6, 55.1, 67.1, 100.9, 106.2, 106.6, 116.9, 129.8, 134.4, 160.1, 160.8; FT-IR (film, NaCl) $v_{max}$=3136, 2378, 1644, 1509 cm$^{-1}$; CI LRMS m/z (ion): 179.20 (M+H)$^+$.

Example 4

1-(Allyloxy)-3-methoxybenzene (5d): Title compound was obtained from allyl alcohol 4d, as described for 5a in 96% yield after flash-chromatography (98:2 hexanes:EtOAc) as a colorless oil. $^1$H NMR (400 MHz, CDCl$_3$): δ 3.81 (s, 3H), 4.02 (d, J=6.7 Hz, 2H), 5.13-5.23 (m, 2H), 5.89-5.97 (m, 1H), 6.51-6.56 (m, 3H), 7.20 (t, J=8.1 Hz, 1H); $^{13}$C NMR (100 MHz, CDCl$_3$): δ 55.1, 67.1, 100.9, 106.2, 106.6, 116.9, 129.8, 134.4, 160.1, 160.8.

Example 5

2-(Hex-5-enyloxy)-4-methoxybenzenesulfonic acid (6a): To 6a (2 g, 9.7 mmol) was added acetic anhydride (1.4 mL, 14.5 mmol) and the resulting mixture was stirred at 0° C. To this was then added concd H$_2$SO$_4$ (1.1 gm) followed by methanol (20 mL). The resulting solution was warmed to 23° C. and stirred for 12 h. After this time the reaction mixture was concentrated in vacuo and the resulting red oil was subjected to column chromatography (88:12 CH$_2$Cl$_2$:MeOH) to give 6a (1.06 g, 38%) as a red waxy solid. $^1$H NMR (400 MHz, D$_2$O): δ 1.44 (quintet, J=7.4 Hz, 2H), 1.66-1.73 (m, 2H), 1.99 (q, J=7.1 Hz, 2H), 3.70 (s, 3H), 3.98 (t, J=6.5 Hz, 2H), 4.85-4.97 (m, 2H), 5.74-5.92 (m, 1H), 6.52-6.56 (m, 3H), 7.19-7.24 (m, 1H); $^{13}$C NMR (100 MHz, D$_2$O): δ 25.3, 28.7, 33.4, 55.1, 67.6, 100.9, 106.0, 106.6, 114.7, 129.8, 138.5, 160.3, 160.8; ESI m/z (ion): 285.09 (M−H)$^-$.

Example 6

4-Methoxy-2-(pent-4-enyloxy)benzenesulfonic acid (6b): Title compound was obtained from ether 5b as described for 6a in 36% yield after flash-chromatography (88:12 CH$_2$Cl$_2$:MeOH) as a white solid. $^1$H NMR (400 MHz, D$_2$O): δ 1.75-1.82 (m, 2H), 2.10-2.16 (m, 2H), 3.69 (s, 3H), 3.98 (t, J=6.4 Hz, 2H), 4.88-5.00 (m, 2H), 5.77-5.87 (m, 1H), 6.45 (dd, J=8.6, 2.2 Hz, 1H), 6.51 (d, J=2.1 Hz, 1H), 7.58 (d, J=8.8 Hz, 1H); $^{13}$C NMR (100 MHz, D$_2$O): δ 28.0, 29.9, 56.1, 68.7, 100.5, 104.9, 115.5, 123.7, 130.2, 139.4, 157.8, 163.5; ESI m/z (ion): 271.07 (M−H)$^-$.

Example 7

2-(But-3-enyloxy)-4-methoxybenzenesulfonic acid (6c): Title compound was obtained from ether 5c as described for 6a in 30% yield after flash-chromatography (88:12 CH$_2$Cl$_2$:MeOH) as a white solid. $^1$H NMR (400 MHz, D$_2$O): δ 2.38-2.43 (m, 2H), 3.62 (s, 3H), 3.98 (t, J=6.8 Hz, 2H), 4.93-5.05

(m, 2H), 5.77-5.87 (m, 1H), 6.37 (dd, J=8.6, 2.2 Hz, 1H), 6.43 (d, J=2.4 Hz, 1H), 7.58 (d, J=8.8 Hz, 1H); $^{13}$C NMR (100 MHz, D$_2$O): δ 33.3, 56.1, 68.8, 100.6, 117.5, 123.7, 130.2, 135.4, 157.5, 163.4; ESI m/z (ion): 257.10 (M−H)$^-$.

Example 8

2-(Allyloxy)-4-methoxybenzenesulfonic acid (6d): Title compound was obtained from ether 5d as described for 6a in 35% yield after flash-chromatography (88:12 CH$_2$Cl$_2$: MeOH) as a white solid. $^1$H NMR (400 MHz, D$_2$O): δ 2.38-2.43 (m, 2H), 3.62 (s, 3H), 3.98 (t, J=6.8 Hz, 2H), 4.93-5.05 (m, 2H), 5.77-5.87 (m, 1H), 6.37 (dd, J=8.6, 2.2 Hz, 1H), 6.43 (d, J=2.4 Hz, 1H), 7.58 (d, J=8.8 Hz, 1H); $^{13}$C NMR (100 MHz, D$_2$O): δ 33.3, 56.1, 68.8, 100.6, 117.5, 123.7, 130.2, 135.4, 157.5, 163.4; ESI m/z (ion): 243.13 (M−H)$^-$.

Example 9

2-(Hex-5-enyloxy)-4-methoxybenzene-1-sulfonyl chloride (7a): To a stirring solution of sulfonic acid 6a (266 mg, 0.9 mmol) in pyridine (2 mL) was added thionyl chloride (0.2 mL, 2.8 mmol) dropwise. The resulting solution was allowed to stir for 4 h and then the reaction mixture concentrated in vacuo. The resulting residue was purified using column chromatography (5:1 hexanes:EtOAc) to give 7a (140 mg, 50%) as a colorless oil. $^1$H NMR (400 MHz, CDCl$_3$): δ 1.63-1.70 (m, 2H), 1.87-1.93 (m, 2H), 2.10-2.16 (m, 2H), 3.88 (s, 3H), 4.14 (t, J=6.2 Hz, 2H), 4.95-5.05 (m, 2H), 5.76-5.86 (m, 1H), 6.51-6.54 (m, 3H), 7.84 (d, J=9.6 Hz, 1H); $^{13}$C NMR (100 MHz, CDCl$_3$): δ 24.9, 28.1, 33.1, 55.9, 69.2, 99.9, 104.6, 114.7, 124.3, 131.7, 138.3, 158.7, 166.8.

Example 10

4-Methoxy-2-(pent-4-enyloxy)benzene-1-sulfonyl chloride (7b): Title compound was obtained from ether 6b as described for 7a in 48% yield after flash-chromatography (6:1 hexanes:EtOAc) as a colorless oil. $^1$H NMR (400 MHz, CDCl$_3$): δ 1.96-1.2.03 (m, 2H), 2.31-2.37 (m, 2H), 3.88 (s, 3H), 4.15 (t, J=6.2 Hz, 2H), 4.99-5.09 (m, 2H), 5.79-5.90 (m, 1H), 6.51-6.54 (m, 3H), 7.84 (d, J=9.2 Hz, 1H); $^{13}$C NMR (100 MHz, CDCl$_3$): δ 27.8, 29.7, 55.9, 68.4. 99.9, 104.6, 115.6, 124.3, 131.7, 137.3, 158.6, 166.8.

Example 11

2-(But-3-enyloxy)-4-methoxybenzene-1-sulfonyl chloride (7c): Title compound was obtained from ether 6c as described for 7a in 52% yield after flash-chromatography (6:1 hexanes:EtOAc) as a colorless oil. $^1$H NMR (400 MHz, CDCl$_3$): δ 1.96-1.2.03 (m, 2H), 2.31-2.37 (m, 2H), 3.88 (s, 3H), 4.15 (t, J=6.2 Hz, 2H), 4.99-5.09 (m, 2H), 5.79-5.90 (m, 1H), 6.51-6.54 (m, 2H), 7.84 (d, J=9.2 Hz, 1H); $^{13}$C NMR (100 MHz, CDCl$_3$): δ 27.8, 29.7, 55.9, 68.4. 99.9, 104.6, 115.6, 124.3, 131.7, 137.3, 158.6, 166.8.

Example 12

2-(Allyloxy)-4-methoxybenzene-1-sulfonyl chloride (7d): Title compound was obtained from ether 6d as described for 7a in 58% yield after flash-chromatography (6:1 hexanes: EtOAc) as a colorless oil. $^1$H NMR (400 MHz, CDCl$_3$): δ 3.88 (s, 3H), 4.72 (d, J=4.4 Hz, 2H), 5.33 (d, J=10.6 Hz, 1H), 5.57 (d, J=17.3 Hz, 1H), 5.99-6.07 (m, 1H), 6.52-6.55 (m, 2H), 7.83 (d, J=8.7 Hz, 1H); $^{13}$C NMR (100 MHz, CDCl$_3$): δ 55.9, 69.7, 100.5, 105.0, 118.1, 124.4, 131.0, 131.7, 158.0, 166.7.

Example 13 tert-Butyl (2S,3R)-4-(hex-5-enylamino)-3-hydroxy-1-phenylbutan-2-ylcarbamate (10a): A solution of hex-5-en-1-amine 9a (297 mg, 3 mmol) and epoxide 8 (263 mg, 1 mmol) was heated to 60° C. in isopropanol (4 mL) for 4 h. The solvent was then evaporated under reduced pressure and the resulting residue was purified by silica chromatography (5:95 MeOH:CHCl$_3$) to give 10a (350 mg, 97%) as a white solid. $^1$H NMR (400 MHz, CDCl$_3$): δ 1.34 (s, 9H), 1.39-1.50 (m, 4H), 2.05 (q, J=7 Hz, 2H), 2.55-2.68 (m, 6H), 2.81-2.86 (m, 1H), 2.96 (dd, J=4.5, 14 Hz, 1H), 3.44-3.49 (m, 1H), 3.79 (br s, 1H), 4.72 (d, J=8.7 Hz, 1H), 4.92-5.02 (m, 2H), 5.74-5.84 (m, 1H), 7.17-7.28 (m, 5H); $^{13}$C NMR (100 MHz, CDCl$_3$): δ 26.4, 28.2, 29.4, 33.4, 36.5, 49.6, 51.3, 54.1, 70.7, 114.5, 126.2, 128.3, 129.4, 137.8, 138.6, 155.9; CI LRMS m/z (ion): 363.55 (M+H)$^+$.

Example 14 tert-Butyl (2S,3R)-4-(allylamino)-3-hydroxy-1-phenylbutan-2-ylcarbamate (10b): Title compound was obtained from allylamine 9b and epoxide 8 as described for 10a in 99% yield after flash-chromatography (5:95 MeOH:CHCl$_3$) as a white solid. $^1$H NMR (400 MHz, CDCl$_3$): δ 1.35 (s, 9H), 2.60-2.86 (m, 5H), 2.96 (dd, J=4.5, 14.1 Hz, 1H), 3.16-3.29 (m, 2H), 3.50-3.53 (m, 1H), 3.81 (br s, 1H), 4.73 (d, J=9.1 Hz, 1H), 5.10 (d, J=10.3 Hz, 1H), 5.17 (d, J=17 Hz, 1H), 5.81-5.91 (m, 1H), 7.13-7.32 (m, 5H); $^{13}$C NMR (100 MHz, CDCl$_3$): δ 28.2, 36.5, 50.7, 52.1, 54.1, 70.9, 79.3, 116.2, 126.2, 128.3, 129.4, 137.8, 155.9; CI LRMS m/z (ion) 321.50 (M+H)$^+$.

Example 15 tert-Butyl-(2S,3R)-4-(N-(hex-5-enyl)-2-(hex-5-enyloxy)-4-ethoxyphenylsulfonamido)-3-hydroxy-1-phenylbutan-2-ylcarbamate (11a): To a stirring solution of 10a (50 mg, 0.14 mmol) in pyridine (2 mL) was added 7a (64 mg, 0.20 mmol) and the resulting solution was allowed to stir for 2 h at 23° C. The reaction mixture was concentrated under reduced pressure and the resulting residue was purified by flash column chromatography (3:1 hexanes:EtOAc) to yield 74 mg (84% yield) of 11a as a colorless oil. [α]$_D^{20}$ −1.4 (c 1.00, CHCl$_3$); $^1$H NMR (400 MHz, CDCl$_3$): δ 1.25-1.34 (m, 12H), 1.47-1.50 (m, 2H), 1.57-1.60 (m, 2H), 1.82-1.90 (m, 2H), 1.97 (q, J=7.1 Hz, 2H), 2.11 (q, J=7.0 Hz, 2H), 2.92-2.95 (m, 2H), 3.10-3.17 (m, 1H), 3.30 (br s, 3H), 3.76 (br s, 2H), 3.84 (s, 3H), 3.90-3.92 (m, 1H) 4.03 (t, J=6.7 Hz, 2H), 4.65 (d, J=7.1 Hz, 1H), 4.89-5.04 (m, 4H), 5.66-5.82 (m, 2H), 6.46 (d, J=2 Hz), 6.49 (dd, J=8.8, 2.3 Hz, 1H), 7.17-7.29 (m, 5H), 7.83 (d, J=7.8 Hz, 1H); $^{13}$C NMR (100 MHz, CDCl$_3$): δ 24.9, 25.7, 27.9, 28.2, 28.3, 33.1, 33.2, 35.1, 49.9, 52.3, 54.5, 55.6, 69.1, 72.2, 79.4, 100.2, 104.1, 114.7, 115.0, 119.4, 126.2, 128.3, 129.5, 133.5, 137.8, 138.1, 138.2, 156.0, 157.6, 164.7; FT-IR (film, NaCl) ν$_{max}$=3395, 2935, 1705, 1597, 1325 cm$^{-1}$; ESI (+) LRMS m/z (ion): 653.13 (M+Na)$^+$.

Example 16 tert-Butyl-(2S,3R)-4-(N-(hex-5-enyl)-4-methoxy-2-(pent-4-enyloxy)phenylsulfonamido)-3-hydroxy-1-phenylbutan-2-ylcarbamate (11b): Title compound was obtained from 10a and 7b, as described for 11a in 79% yield after flash-chromatography (3:1 hexanes:EtOAc) as a colorless oil.

[α]$_D^{20}$ −1.6 (c 1.20, CHCl$_3$); $^1$H NMR (400 MHz, CDCl$_3$): δ 1.25-1.37 (m, 12H), 1.43-1.51 (m, 2H), 1.88-1.98 (m, 4H), 2.27 (q, J=7.1 Hz, 2H), 2.86-2.97 (m, 2H), 3.10-3.17 (m, 1H), 3.25-3.31 (m, 3H), 3.76 (br s, 2H), 3.84 (s, 3H), 4.04 (t, J=6.6 Hz, 2H), 4.66 (d, J=7.1 Hz, 1H), 4.88-5.10 (m, 4H), 5.65-5.72 (m, 1H), 5.78-5.85 (m, 1H), 6.46 (d, J=2 Hz), 6.49 (dd, J=8.8, 2.0 Hz, 1H), 7.17-7.29 (m, 5H), 7.83 (d, J=8.7 Hz, 1H); $^{13}$C NMR (100 MHz, CDCl$_3$): δ 25.7, 27.9, 28.2, 33.1, 35.2, 49.8, 52.2, 54.6, 55.6, 68.4, 72.2, 79.4, 100.2, 104.1, 114.7, 115.7, 119.4, 126.2, 128.3, 129.5, 133.5, 137.0, 137.8, 138.2, 156.0, 157.6, 164.7; FT-IR (film, NaCl) ν$_{max}$=3398, 2931, 1706, 1596, 1325 cm$^{-1}$; ESI (+) LRMS m/z (ion): 639.06 (M+Na)$^+$.

Example 17 tert-Butyl-(2S,3R)-4-(2-(but-3-enyloxy)-N-(hex-5-enyl)-4-methoxyphenylsulfonamido)-3-hydroxy-1-phenylbutan-2-ylcarbamate (11c): Title compound was obtained from 10a and 7c, as described for 11a in 50% yield after flash-chromatography (3:1 hexanes:EtOAc) as a colorless oil. [α]$_D^{20}$ +0.6 (c 2.00, CHCl$_3$); $^1$H NMR (500 MHz, CDCl$_3$): δ 1.28-1.38 (m, 12H), 1.48-1.52 (m, 2H), 2.00 (q, J=6.7 Hz, 2H), 2.65 (q, J=6.7 Hz, 2H), 2.96 (br s, 2H), 3.14-3.18 (m, 1H), 3.30-3.39 (m, 3H), 3.79 (br s, 2H), 3.88 (s, 3H), 4.13 (t, J=7.1 Hz, 2H), 4.68 (d, J=5.1 Hz, 1H), 4.92-4.98 (m, 2H), 5.17-5.24 (m, 2H), 5.68-5.76 (m, 1H), 5.91-5.99 (m, 1H), 6.51 (d, J=2 Hz, 1H), 6.54 (dd, J=8.8, 2.0 Hz, 1H), 7.21-7.32 (m, 5H), 7.88 (d, J=8.8 Hz, 1H); $^{13}$C NMR (125 MHz, CDCl$_3$): δ 25.9, 28.4, 33.4, 35.4, 50.1, 52.5, 54.8, 55.9, 68.7, 72.5, 79.7, 100.6, 104.5, 114.9, 118.0, 119.8, 126.5, 128.6, 129.8, 133.7, 133.9 138.1, 138.5, 156.3, 157.7, 165.0; FT-IR (film, NaCl) ν$_{max}$=3394, 2931, 1704, 1596, 1325 cm$^{-1}$; ESI (+) m/z (ion): 625.05 (M+Na)$^+$.

Example 18 tert-Butyl(2S,3R)-4-(2-(allyloxy)-N-(hex-5-enyl)-4-methoxyphenylsulfonamido)-3-hydroxy-1-phenylbutan-2-ylcarbamate (11d): Title compound was obtained from 10a and 7d, as described for 11a in 64% yield after flash-chromatography (3:1 hexanes:EtOAc) as a colorless oil. [α]$_D^{20}$ +1.1 (c 2.80, CHCl$_3$); $^1$H NMR (400 MHz, CDCl$_3$): δ 1.25-1.34 (m, 12H), 1.39-1.46 (m, 2H), 1.96 (q, J=7.0 Hz, 2H), 2.89-2.96 (m, 2H), 3.08-3.15 (m, 1H), 3.24-3.30 (m, 3H), 3.77 (br s, 2H), 3.84 (s, 3H), 4.60 (d, J=5.4 Hz, 2H), 4.66 (d, J=7.2 Hz, 1H), 4.88-4.94 (m, 2H), 5.33 (d, J=10.4, 2H), 5.43 (d, J=17.4 Hz, 1H), 5.63-5.73 (m, 1H), 6.00-6.10 (m, 1H), 6.47 (d, J=1.8 Hz, 1H), 6.54 (dd, J=8.9, 1.9 Hz, 1H), 7.18-7.29 (m, 5H), 7.85 (d, J=8.8 Hz, 1H); $^{13}$C NMR (100 MHz, CDCl$_3$): δ 25.7, 28.2, 33.1, 35.2, 49.9, 52.5, 54.5, 55.6, 69.9, 72.2, 79.4, 100.6, 104.4, 114.7, 119.4, 119.7 126.2, 128.3, 129.5, 131.9, 133.5, 137.9, 138.2, 155.9, 157.0, 164.6; FT-IR (film, NaCl) ν$_{max}$=3400, 2929, 1704, 1596, 1324 cm$^{-1}$; ESI (+) m/z (ion): 611.03 (M+Na)$^+$.

Example 19 tert-Butyl-(2S,3R)-4-(N-allyl-2-(hex-5-enyloxy)-4-methoxyphenylsulfonamido)-3-hydroxy-1-phenylbutan-2-ylcarbamate (11e): Title compound was obtained from 10b and 7a, as described for 11a in 77% yield after flash-chromatography (3:1 hexanes:EtOAc) as a colorless oil. [α]$_D^{20}$ −6.6 (c 1.96, CHCl$_3$); $^1$H NMR (500 MHz, CDCl$_3$): δ 1.36 (s, 9H), 1.60-1.66 (m, 2H), 1.87-1.97 (m, 2H), 2.13-2.17 (m, 2H), 2.91-2.98 (m, 2H), 3.27-3.39 (m, 2H), 3.79 (br s, 2H), 3.87 (s, 3H), 3.91-3.99 (m, 2H), 4.08 (t, J=6.7 Hz, 2H), 4.65 (d, J=7.1 Hz, 1H), 4.98 (d, J=10.1 Hz, 1H), 5.04 (d, J=17.1 Hz, 1H), 5.13-5.19 (m, 2H), 5.63-5.73 (m, 1H), 5.78-5.86 (m, 1H), 6.50-6.53 (m, 2H), 7.21-7.31 (m, 5H), 7.88 (d, J=8.7 Hz, 1H); $^{13}$C NMR (100 MHz, CDCl$_3$): δ 25.0, 28.3, 33.3, 35.3, 51.2, 52.2, 54.6, 55.7, 69.2, 71.8, 79.5, 100.3, 104.2, 115.1, 119.0, 119.6, 126.3, 128.4, 129.6, 133.6, 137.9, 138.2, 156.1, 157.7, 164.8; FT-IR (film, NaCl) ν$_{max}$=3392, 2932, 1702, 1595, 1324 cm$^{-1}$; ESI (+) m/z (ion): 611.04 (M+Na)$^+$.

Example 20 tert-Butyl-(2S,3R)-4-(N-allyl-4-methoxy-2-(pent-4-enyloxy)phenylsulfonamido)-3-hydroxy-1-phenylbutan-2-ylcarbamate (11f): Title compound was obtained from 10b and 7b, as described for 11a in 86% yield after flash-chromatography (3:1 hexanes:EtOAc) as a colorless oil. [α]$_D^{20}$ −5.6 (c 1.10, CHCl$_3$); $^1$H NMR (400 MHz, CDCl$_3$): δ 1.32 (s, 9H), 1.94 (quintet, J=7 Hz, 2H), 2.65 (q, J=7 Hz, 2H), 2.86-2.96 (m, 2H), 3.27 (dd, J=7.4, 14.8 Hz, 1H), 3.34-3.38 (m, 1H), 3.76 (br s, 2H), 3.82 (s, 3H), 3.87-3.92 (m, 2H), 4.04 (t, J=6.5 Hz, 2H), 4.65 (d, J=8.2 Hz, 1H), 4.98-5.15 (m, 4H), 5.57-5.63 (m, 1H), 5.75-5.86 (m, 1H), 6.46-6.49 (m, 2H), 7.12-7.27 (m, 5H), 7.83 (d, J=8.5 Hz, 1H); $^{13}$C NMR (100 MHz, CDCl$_3$): δ 27.8, 28.1, 35.3, 51.0, 51.9, 54.5, 55.6, 68.4, 71.8, 79.3, 100.2, 104.2, 115.7, 119.0, 119.5, 126.2, 128.2, 129.5, 133.4, 137.2, 137.9, 155.9, 157.6, 164.7; FT-IR (film, NaCl) ν$_{max}$=3390, 2976, 1710, 1597, 1325 cm$^{-1}$; ESI (+) m/z (ion): 597.13 (M+Na)$^+$.

Example 21 tert-Butyl-(2S,3R)-4-(N-allyl-2-(but-3-enyloxy)-4-methoxyphenylsulfonamido)-3-hydroxy-1-phenylbutan-2-ylcarbamate (11g): Title compound was obtained from 10b and 7c, as described for 11a in 78% yield after flash-chromatography (3:1 hexanes:EtOAc) as a colorless oil. $^1$H NMR (500 MHz, CDCl$_3$): δ 1.34 (s, 9H), 2.62 (q, J=7 Hz, 2H), 2.88-2.96 (m, 2H), 3.27 (dd, J=7.8, 15.1 Hz, 1H), 3.34-3.38 (m, 1H), 3.76 (br s, 2H), 3.85 (s, 3H), 3.87-3.99 (m, 2H), 4.10 (t, J=6.5 Hz, 2H), 4.65 (br s, 1H), 5.10-5.22 (m, 4H), 5.57-5.63 (m, 1H), 5.87-5.95 (m, 1H), 6.49 (d, J=2.2 Hz, 1H), 6.51 (dd, J=2.3, 8.7 Hz 1H) 7.18-7.37 (m, 5H), 7.85 (d, J=8.7 Hz, 1H); $^{13}$C NMR (100 MHz, CDCl$_3$): 27.8, 28.1, 35.3, 51.0, 51.9, 54.5, 55.6, 68.4, 71.8, 79.3, 100.2, 104.2, 115.7, 119.0, 119.5, 126.2, 128.2, 129.5, 133.4, 137.2, 137.9, 155.9, 157.6, 164.7; FT-IR (film, NaCl) ν$_{max}$=3390, 2976, 1710, 1597, 1325 cm$^{-1}$; ESI (+) m/z (ion): 582.95 (M+Na)$^+$.

Example 22 tert-Butyl-(2S,3R)-4-(N-allyl-2-(allyloxy)-4-methoxyphenylsulfonamido)-3-hydroxy-1-phenylbutan-2-ylcarbamate (11h): Title compound was obtained from 10b and 7d, as described for 11a in 80% yield after flash-chromatography (3:1 hexanes:EtOAc) as a colorless oil. $^1$H NMR (400 MHz, CDCl$_3$): δ 1.33 (s, 9H), 2.83-2.96 (m, 2H), 3.25-3.36 (m, 2H), 3.77 (br s, 2H), 3.83 (s, 3H), 3.87-3.94 (m, 2H), 4.56-4.67 (m, 3H), 5.07-5.14 (m, 2H), 5.33 (d, J=10.5 Hz, 1H), 5.44 (d, J=17.2 Hz, 1H), 5.57-5.64 (m, 1H), 6.00-6.10 (m, 1H), 6.47 (d, J=1.9 Hz, 1H), 6.51 (dd, J=1.9, 8.9 Hz, 1H) 7.16-7.28 (m, 5H), 7.85 (d, J=8.7 Hz, 1H); $^{13}$C NMR (100 MHz, CDCl$_3$): δ 28.2, 35.3, 51.3, 52.1, 54.5, 55.6, 69.9, 71.8, 79.3, 100.6, 104.5, 119.0, 119.4, 119.8, 126.2, 128.2, 129.5, 131.8, 133.4, 137.9, 155.9, 157.0, 164.7; FT-IR (film, NaCl) ν$_{max}$=3390, 2976, 1710, 1597, 1325 cm$^{-1}$; ESI (+) m/z (ion): 569.06 (M+Na)$^+$.

Example 23

Compound 13a: To a stirring solution of 11a (63 mg, 0.1 mmol) in CH$_2$Cl$_2$ (2 mL) was added a solution of 30% trifluoroacetic acid in CH$_2$Cl$_2$ and the resulting mixture was stirred for 30 min. The solvent was evaporated under reduced pressure and the residue was dissolved in CH$_3$CN (2 mL). The solution was added to 12 (31 mg, 0.11 mmol), followed by i-Pr$_2$NEt. After stirring for 24 h the reaction mixture was concentrated in vacuo and the resulting residue was subjected to flash-chromatography (1:1 hexanes:EtOAc) to give 36 mg (53% yield) of 13a as a colorless oil. [α]$_D^{20}$ −13.1 (c 1.50, CHCl$_3$); $^1$H NMR (500 MHz, CDCl$_3$): δ 1.28-1.31 (m, 2H), 1.47-1.51 (m, 2H), 1.58-1.61 (m, 3H), 1.84-1.88 (m, 2H), 1.96-1.99 (m, 2H), 2.01-2.13 (m, 2H), 2.79-2.84 (m, 1H), 2.98-3.02 (m, 1H), 3.09-3.15 (m, 1H), 3.24-3.40 (m, 3H), 3.61 (br s, 1H), 3.64-3.72 (m, 2H), 3.83-3.92 (m, 4H), 3.93-3.96 (m, 1H), 4.05 (t, J=6.7 Hz, 2H), 4.90-5.03 (m, 4H), 5.64 (d, J=5 Hz, 1H), 5.66-5.82 (m, 2H), 6.46 (s, 1H), 6.51 (d, J=8.8 Hz, 1H), 7.17-7.26 (m, 5H), 7.83 (d, J=8.8 Hz, 1H); $^{13}$C NMR (125 MHz, CDCl$_3$): δ 27.9, 28.2, 28.1, 29.4, 31.7, 32.9, 33.1, 35.1, 45.1, 49.8, 52.1, 54.8, 55.5, 68.9, 69.3, 70.5, 72.0 73.1, 100.1, 103.9, 109.0, 114.6, 114.9, 118.9, 126.3, 128.2, 128.7, 129.1, 133.4, 137.4, 137.8, 138.0, 155.2, 157.4, 164.6; FT-IR (film, NaCl) ν$_{max}$=3343, 2928, 1721, 1595, 1325 cm$^{-1}$; ESI (+) HRMS (m/z): [M+Na]$^+$ calcd for C$_{36}$H$_{50}$N$_2$O$_9$S, 709.3135. found, 709.3136.

Example 24

Compound 13b: Title compound was obtained from 11b and 12 as described for 13a in 55% yield after flash-chromatography (1:1 hexanes:EtOAc) as a colorless oil. $^1$H NMR (500 MHz, CDCl$_3$): δ 1.27-1.32 (m, 2H), 1.41-1.53 (m, 3H), 1.57-1.62 (m, 1H), 1.92-1.99 (m, 4H), 2.80 (dd, J=10, 14 Hz, 1H), 2.86-2.91 (m, 1H), 3.01 (dd, J=4, 14 Hz, 1H), 3.10-3.15 (m, 1H), 3.27-3.33 (m, 2H), 3.38 (dd, J=8.6, 15.2 Hz, 1H), 3.61 (br s, 1H), 3.64-3.70 (m, 2H), 3.81-3.84 (m, 5H), 3.88-3.95 (m, 2H), 4.05 (t, J=6.6 Hz, 2H), 4.89-5.09 (m, 4H), 5.63 (d, J=5.2 Hz, 1H), 5.65-5.73 (m, 1H), 5.77-5.85 (m, 1H), 6.46 (d, J=2 Hz, 1H), 6.51 (dd, J=2.1, 8.8 Hz, 1H), 7.17-7.26 (m, 5H), 7.83 (d, J=8.8 Hz, 1H); $^{13}$C NMR (100 MHz, CDCl$_3$): δ 25.7, 27.9, 29.7, 33.1, 35.4, 45.1, 49.8, 52.1, 55.1, 55.7, 68.5, 69.5, 70.7, 72.2 73.2, 100.3, 104.2, 109.2, 114.8, 115.7, 119.2, 126.4, 128.4, 129.3, 133.6, 137.1, 137.6, 138.2, 155.4, 157.5, 164.8; ESI (+) HRMS (m/z): [M+H]$^+$ calcd for C$_{35}$H$_{48}$N$_2$O$_9$S, 673.3159. found, 673.3153.

Example 25

Compound 13c: Title compound was obtained from 11c and 12 as described for 13a in 81% yield after flash-chromatography (1:1 hexanes:EtOAc) as a colorless oil. $^1$H NMR (500 MHz, CDCl$_3$): δ 1.31-1.35 (m, 2H), 1.50-1.54 (m, 3H), 1.62-1.67 (m, 1H), 2.00 (q, J=7 Hz, 2H), 2.65 (q, J=6.7 Hz, 2H), 2.82-2.87 (m, 1H), 2.91-2.94 (m, 1H), 3.06 (dd, J=4.1, 14.2 Hz, 1H), 3.13-3.19 (m, 1H), 3.30-3.43 (m, 3H), 3.62 (br s, 1H), 3.68-3.74 (m, 2H), 3.85-3.88 (m, 4H), 3.92-3.99 (m, 2H), 4.13 (t, J=6.9 Hz, 2H), 4.93-5.05 (m, 2H), 5.17-5.24 (m, 2H), 5.66 (d, J=5.1 Hz, 1H), 5.69-5.77 (m, 1H), 5.90-5.99 (m, 1H), 6.52 (s, 1H), 6.55 (dd, J=2.05, 8.8 Hz, 1H), 7.22-7.30 (m, 5H), 7.87 (d, J=8.8 Hz, 1H); $^{13}$C NMR (125 MHz, CDCl$_3$): δ 25.8, 28.1, 29.8, 33.3, 35.6, 45.4, 50.0, 52.4, 55.2, 55.8, 68.7, 69.7, 70.8, 72.4, 73.4, 100.6, 104.5, 109.4, 114.9, 119.5, 126.6, 128.6, 129.5, 133.5, 137.8, 138.3, 155.9, 157.6, 164.9; FT-IR (film, NaCl) ν$_{max}$=3339, 2929, 1719, 1596, 1324 cm$^{-1}$; ESI (+) HRMS (m/z): [M+Na]$^+$ calcd for C$_{34}$H$_{46}$N$_2$O$_9$S, 681.2822. found, 681.2812.

Example 26

Compound 13d: Title compound was obtained from 11d and 12 as described for 13a in 55% yield after flash-chromatography (1:1 hexanes:EtOAc) as a colorless oil. $^1$H NMR (500 MHz, CDCl$_3$): δ 1.24-1.30 (m, 2H), 1.43-1.51 (m, 3H), 1.57-1.63 (m, 1H), 1.96 (q, J=7 Hz, 2H), 2.80 (dd, J=10, 14 Hz, 1H), 2.86-2.91 (m, 1H), 3.01 (dd, J=4.5, 14.5 Hz, 1H), 3.08-3.14 (m, 1H), 3.25-3.30 (m, 2H), 3.40 (dd, J=8.5, 15 Hz, 1H) 3.58 (br s, 1H), 3.65-3.72 (m, 2H), 3.80-3.82 (m, 2H), 3.87 (s, 3H), 3.88-3.96 (m, 2H), 4.60 (d, J=5.5 Hz, 2H), 4.90-4.95 (m, 2H), 4.98-5.06 (m, 2H), 5.33 (d, J=10 Hz, 1H), 5.45 (d, J=18 Hz, 1H), 5.64 (d, J=5.5 Hz, 1H), 5.65-5.72 (m, 1H), 6.02-6.10 (m, 1H), 6.47 (d, J=2 Hz, 1H), 6.53 (dd, J=2.5, 9 Hz, 1H), 7.17-7.27 (m, 5H), 7.85 (d, J=9 Hz, 1H); $^{13}$C NMR (125 MHz, CDCl$_3$): δ 25.7, 27.8, 33.0, 35.3, 45.2, 49.9, 52.4, 55.6, 69.5, 69.9, 70.6, 72.2, 73.3, 100.6, 104.5, 109.2, 114.7, 119.4, 126.4, 128.4, 129.3, 131.9, 133.5, 137.6, 138.1, 155.4, 157.0, 164.7; FT-IR (film, NaCl) ν$_{max}$=3339, 1718, 1594, 1324 cm$^{-1}$; ESI (+) HRMS (m/z): [M+Na]$^+$ calcd for C$_{33}$H$_{44}$N$_2$O$_9$S, 667.2665. found, 667.2661.

Example 27

Compound 13e: Title compound was obtained from 11e and 12 as described for 13a in 68% yield after flash-chromatography (1:1 hexanes:EtOAc) as a colorless oil. $^1$H NMR (400 MHz, CDCl$_3$): δ 1.52-1.61 (m, 3H), 1.81-1.93 (m, 2H), 2.09 (q, J=7 Hz, 2H), 2.76 (dd, J=10, 13.7 Hz, 1H), 2.83-2.88 (m, 1H), 3.01 (dd, J=3.6, 14.2 Hz, 1H), 3.28-3.32 (m, 2H), 3.61-3.69 (m, 2H), 3.78-3.85 (m, 5H), 3.87-3.93 (m, 3H), 4.04 (t, J=6.5 Hz, 2H), 4.92-5.01 (m, 2H), 5.09-5.16 (m, 2H), 5.60-5.71 (m, 2H), 5.72-5.81 (m, 1H), 6.47-6.51 (m, 2H), 7.14-7.26 (m, 5H), 7.82 (d, J=8.6 Hz, 1H); $^{13}$C NMR (100 MHz, CDCl$_3$): δ 24.9, 25.7, 33.2, 35.4, 45.3, 51.0, 52.1, 54.9, 55.7, 69.1, 69.5, 70.7, 71.8, 73.1, 100.3, 104.2, 109.2, 115.0, 119.0, 119.2, 126.3, 128.3, 129.3, 133.4, 133.6, 137.5, 138.0, 155.4, 157.6, 164.8; FT-IR (film, NaCl) ν$_{max}$=3368, 1720, 1596, 1325 cm$^{-1}$; ESI (+) HRMS (m/z): [M+Na]$^+$ calcd for C$_{33}$H$_{44}$N$_2$O$_9$S, 667.2665. found, 667.2668.

Example 28

Compound 13f: Title compound was obtained from 11f and 12 as described for 13a in 64% yield after flash-chromatography (1:1 hexanes:EtOAc) as a colorless oil. $^1$H NMR (400 MHz, CDCl$_3$): δ 1.37-1.43 (m, 1H), 1.54-1.62 (m, 2H), 1.91-1.97 (m, 2H), 2.27 (q, J=7 Hz, 2H), 2.76 (dd, J=10.1, 13.9 Hz, 1H), 2.84-2.89 (m, 1H), 3.02 (dd, J=4, 14.1 Hz, 1H), 3.30-3.37 (m, 2H), 3.54 (br s, 1H), 3.62-3.69 (m, 2H), 3.79-3.87 (m, 5H), 3.88-3.95 (m, 4H), 4.06 (t, J=6.7 Hz, 2H), 4.96-5.00 (m, 2H), 5.04-5.16 (m, 4H), 5.59-5.67 (m, 2H), 5.76-5.85 (m, 1H), 6.47 (d, J=1.9 Hz, 1H), 6.50 (dd, J=2.1, 8.9 Hz, 1H), 7.16-7.26 (m, 5H), 7.82 (d, J=8.8 Hz, 1H); $^{13}$C NMR (100 MHz, CDCl$_3$): δ 25.7, 27.9, 29.7, 35.5, 45.3, 51.0, 52.1, 54.9, 55.7, 68.5, 69.5, 70.7, 71.8, 73.2, 100.3, 104.2, 109.2, 115.7, 119.1, 119.3, 126.4, 128.3, 129.3, 133.5, 137.1, 137.7, 155.4, 157.6, 164.8; FT-IR (film, NaCl) ν$_{max}$=3350, 1720, 1596, 1325 cm$^{-1}$; ESI (+) HRMS (m/z): [M+Na]$^+$ calcd for C$_{32}$H$_{42}$N$_2$O$_9$S, 653.2509. found, 653.2509.

Example 29

Compound 13g: Title compound was obtained from 11g and 12 as described for 13a in 68% yield after flash-chromatography (1:1 hexanes:EtOAc) as a colorless oil. $^1$H NMR (400 MHz, CDCl$_3$): δ 1.39-1.45 (m, 1H), 1.56-1.63 (m, 1H), 2.61 (q, J=6.6 Hz, 2H), 2.75-2.80 (m, 1H), 2.86-2.91 (m, 1H), 3.02 (dd, J=4.1, 14.1 Hz, 1H), 3.32 (d, J=5.8 Hz, 2H), 3.53 (br s, 1H), 3.64-3.70 (m, 2H), 3.81-3.95 (m, 8H), 4.10 (t, J=6.7 Hz, 2H), 4.97-5.01 (m, 2H), 5.12-5.20 (m, 4H), 5.62-5.66 (m, 2H), 5.86-5.94 (m, 1H), 6.49 (s, 1H), 6.51 (d, J=9.1 Hz, 1H), 7.18-7.26 (m, 5H), 7.85 (d, J=8.8 Hz, 1H); $^{13}$C NMR (100 MHz, CDCl$_3$): 25.8, 33.2, 35.6, 45.4, 51.2, 52.3, 55.0, 55.8, 68.7, 69.6, 70.8, 71.9, 73.3, 100.5, 104.5, 109.3, 117.9, 119.2, 119.4, 126.5, 128.5, 129.4, 133.5, 133.7, 137.8, 155.4, 157.5, 164.9; FT-IR (film, NaCl) $\nu_{max}$=3350, 1722, 1596, 1325 cm$^{-1}$; ESI (+) HRMS (m/z): [M+H]$^+$ calcd for C$_{31}$H$_{40}$N$_2$O$_9$S, 617.2533. found, 617.2540.

Example 30

Compound 13h: Title compound was obtained from 11h and 12 as described for 13a in 52% yield after flash-chromatography (1:1 hexanes:EtOAc) as a colorless oil. $^1$H NMR (400 MHz, CDCl$_3$): δ 1.37-1.43 (m, 1H), 1.54-1.65 (m, 1H), 2.73-2.80 (m, 1H), 2.85-2.90 (m, 1H), 3.02 (dd, J=2.9, 13.7 Hz, 1H), 3.28-3.39 (m, 2H), 3.51 (br s, 1H), 3.63-3.70 (m, 2H), 3.77-3.95 (m, 10H), 4.62 (d, J=5.2 Hz, 2H), 4.96-5.06 (m, 2H), 5.10-5.16 (m, 2H), 5.33 (d, J=10.4 Hz, 1H), 5.45 (d, J=17.2 Hz, 1H), 5.62-5.66 (m, 2H), 6.01-6.10 (m, 1H), 6.49 (s, 1H), 6.52 (d, J=8.9 Hz, 1H), 7.18-7.33 (m, 5H), 7.85 (d, J=8.8 Hz, 1H); $^{13}$C NMR (100 MHz, CDCl$_3$): δ 25.7, 33.4, 45.3, 51.4, 52.2, 54.9, 55.7, 69.6, 70.0, 70.7, 71.8, 73.1, 100.7, 104.5, 109.2, 119.1, 119.4, 119.5, 126.4, 128.4, 129.3, 133.5, 137.7, 155.3, 157.0, 164.8; FT-IR (film, NaCl) $\nu_{max}$=3351, 1717, 1596, 1324 cm$^{-1}$; ESI (+) HRMS (m/z): [M+H]$^+$ calcd for C$_{30}$H$_{38}$N$_2$O$_9$S, 603.2376. found, 603.2375.

Example 31

Inhibitor 14a: To stirring solution of 13a (32 mg, 0.047 mmol) in CH$_2$Cl$_2$ (15 mL) was added Grubbs 1$^{st}$ gen. cat. (4 mg, 0.0046 mmol). After stirring at 23° C. for 16 h, the solvent was evaporated under reduced pressure and the residue was subjected to flash column chromatography to yield 14a (27 mg, 88% yield) as a white solid and E/Z mixture (3:1, determined by HPLC). The isomers were isolated by reversed-phase HPLC using the following conditions: YMC Pack ODS-A column (250×100 mm, 5 micron); Flow rate=2.75 mL/min; Isocratic 60:40 CH$_3$CN:H$_2$O; T=35° C.; λ=215 nm; E isomer R$_t$=16.47 min; Z isomer R$_t$=14.45 min.

Example 32

14aE: $^1$H NMR (800 MHz, CDCl$_3$): δ 1.39-1.44 (m, 2H), 1.48-1.53 (m, 1H), 1.57-1.64 (m, 4H), 1.68-1.74 (m, 3H), 1.77-1.82 (m, 1H), 1.83-0.188 (m, 1H), 1.94-1.98 (m, 1H), 2.10-2.14 (m, 3H), 2.71 (dd, J=9.6, 14.1 Hz, 1H), 2.86-2.89 (m, 1H), 2.90 (dd, J=4.3, 14.1 Hz, 1H), 2.91-2.99 (m, 2H), 3.31-3.33 (m, 1H), 3.61-3.64 (m, 1H), 3.65-3.70 (m, 2H), 3.73 (br s, 1H), 3.76-3.78 (m, 1H), 3.79-3.85 (m, 5H), 3.93 (dd, J=6.2, 9.4 Hz, 1H), 3.96-3.98 (m, 1H), 4.02-4.05 (m, 1H), 4.87 (d, J=9.1 Hz, 1H), 4.97-5.00 (m, 1H), 5.44-5.48 (m, 1H), 5.54-5.56 (m, 1H), 5.63 (d, J=5.1 Hz, 1H), 6.44 (d, J=2 Hz, 1H), 6.49 (dd, J=2.2, 8.8 Hz, 1H), 7.13-7.24 (m, 5H), 7.84 (d, J=8.8 Hz, 1H); $^{13}$C NMR (125 MHz, CDCl$_3$): δ 25.1, 25.3, 25.7, 26.8, 29.6, 29.8, 30.4, 32.5, 35.5, 45.2, 50.6, 51.6, 54.7, 55.6, 68.8, 69.5, 70.7, 71.6, 73.3, 99.9, 103.9, 109.2, 118.1, 126.4, 128.4, 129.3, 130.5, 132.1, 134.0, 137.4, 155.2, 157.9, 164.9; ESI (+) HRMS (m/z): [M+Na]$^+$ calcd for C$_{34}$H$_{46}$N$_2$O$_9$S, 681.2822. found, 681.2815.

Example 33

14aZ: $^1$H NMR (800 MHz, CDCl$_3$): δ 1.28-1.33 (m, 2H), 1.38-1.47 (m, 2H), 1.52-1.64 (m, 6H), 1.84-1.90 (m, 2H), 2.04-2.08 (m, 2H), 2.16-2.22 (m, 2H), 2.74 (dd, J=9.5, 14.1 Hz, 1H), 2.88-2.90 (m, 1H), 3.00 (dd, J=4.5, 14.1 Hz, 1H), 3.05-3.14 (m, 2H), 3.15 (dd, J=9.4, 15.1 Hz, 1H), 3.44-3.48 (m, 1H), 3.61 (br s, 1H), 3.66-3.71 (m, 2H), 3.76-3.89 (m, 6H), 3.95 (dd, J=6.2, 9.6 Hz, 1H), 4.10-4.15 (m, 1H), 4.87 (d, J=9.1 Hz, 1H), 5.00-5.03 (m, 1H), 5.35-5.39 (m, 1H), 5.49-5.52 (m, 1H), 5.63 (d, J=5.2 Hz, 1H), 6.50 (s, 1H), 6.49 (dd, J=2.3, 8.8 Hz, 1H), 7.17-7.26 (m, 5H), 7.84 (d, J=8.8 Hz, 1H); $^{13}$C NMR (125 MHz, CDCl$_3$): δ 25.0, 25.7, 26.0, 26.6, 27.8, 29.6, 35.5, 45.2, 48.5, 52.0, 54.7, 55.6, 68.8, 69.5, 70.6, 71.9, 73.3, 100.7, 104.2, 109.2, 117.8, 126.4, 128.4, 129.8, 130.0, 134.1, 137.5, 155.2, 158.0, 165.0; ESI (+) HRMS (m/z): [M+Na]$^+$ calcd for C$_{34}$H$_{46}$N$_2$O$_9$S, 681.2822. found, 681.2819.

Example 34

Inhibitor 14b: The title compound was obtained from a ring closing metathesis reaction of 13b using Grubbs 1$^{st}$ gen. cat. as described for 14a. The crude material was purified by silica chromatography (60:40 EtOAc:Hexane) to give the desired product (50% yield) as a mix of E/Z isomers (27:73 by HPLC). The isomers were isolated by chiral HPLC using the following conditions: Chiralpak IA column (250×4.6 mm, 5 micron); Flow rate=0.75 mL/min; Isocratic 60:40 IPA:Hexane; T=25° C.; λ=215 nm; E isomer R$_t$=7.56 min; Z isomer R$_t$=8.89 min.

Example 35

14b-E: $^1$H NMR (800 MHz, CDCl$_3$): δ 1.60-1.20 (m, 4H), 2.30-1.90 (m, 7H), 3.10-2.80 (m, 5H), 3.32 (m, 1H), 4.00-3.50 (m, 12H), 4.15 (m, 2H), 4.98 (m, 2H), 5.45 (m, 1H), 5.63 (m, 2H), 6.51 (m, 2H), 7.25-7.15 (m, 5H), 7.76 (d, J=19.2 Hz, 1H); $^{13}$C NMR (125 MHz, CDCl$_3$): δ 23.1, 24.8, 25.0, 25.7, 26.2, 26.6, 29.0, 35.5, 45.2, 48.2, 52.0, 54.8, 55.6, 67.1, 69.5, 70.7, 71.6, 73.3, 100.1, 104.0, 109.2, 114.6, 118.4, 126.4, 128.4, 128.9, 129.3, 133.6, 133.8, 137.4, 155.3, 157.7, 164.9; ESI (+) HRMS (m/z): [M+Na]$^+$ calcd for C$_{33}$H$_{44}$N$_2$O$_9$S, 667.2665. found, 667.2660.

Example 36

14b-Z: $^1$H NMR (800 MHz, CDCl$_3$): δ 1.60-1.0 (m, 7H); 1.72 (m, 2H), 1.90 (m, 3H), 2.21 (m, 2H), 2.43 (m, 1H), 2.55 (m, 1H), 2.67 (m, 1H), 2.76 (m, 1H), 2.84 (m, 1H), 3.01 (m, 1H), 3.26 (m, 1H), 3.41 (m, 3H), 3.60 (m, 4H), 3.69 (m, 1H), 3.86 (m, 2H), 4.43 (d, J=15.2 Hz, 1H), 4.83 (m, 1H), 5.24 (m, 1H), 5.33 (m, 1H), 5.51 (d, J=8.8 Hz, 1H), 6.45 (m, 2H), 7.17 (m, 3H), 7.24 (m, 2H), 7.87 (d, J=13.6 Hz, 1H); $^{13}$C NMR (125 MHz, CDCl$_3$): δ 24.7, 25.7, 27.3, 28.6, 30.9, 32.1, 35.5, 45.2, 49.3, 51.8, 54.8, 55.6, 69.5, 70.7, 71.0, 71.9, 73.3, 101.2, 104.3, 109.2, 119.3, 126.4, 128.4, 128.9, 129.3, 130.8, 130.9, 133.4, 137.5, 155.3, 158.2, 164.5; ESI (+) HRMS (m/z): [M+Na]$^+$ calcd for C$_{33}$H$_{44}$N$_2$O$_9$S, 667.2665. found, 667.2667.

Example 37

Inhibitor 14c: Title compound was obtained from 13c and Grubbs 1$^{st}$ gen. cat. as described for 14a in 89% yield after flash-chromatography (2:3 hexanes:EtOAc) as a white solid and E/Z mixture (3:1, determined by HPLC). The isomers were isolated using reversed-phase HPLC under the following conditions: YMC Pack ODS-A column (250×100 mm, 5 micron); Flow rate=2.75 mL/min; Isocratic 60:40 CH$_3$CN:H$_2$O; T=35° C.; λ=215 nm; E isomer R$_t$=13.43 min; Z isomer R$_t$=11.76 min.

Example 38

14cE: $^1$H NMR (800 MHz, CDCl$_3$): δ 1.45-1.54 (m, 3H), 1.56-1.64 (m, 2H), 1.68-1.72 (m, 1H), 2.11-2.20 (m, 2H), 2.52-2.62 (m, 2H), 2.79 (dd, J=9.6, 14 Hz, 1H), 2.87-2.90 (m, 1H), 2.96-3.00 (m, 2H), 3.04 (dd, J=4.2, 14.2 Hz, 1H), 3.40-3.44 (m, 1H), 3.53-3.56 (m, 1H), 3.66-3.70 (m, 2H), 3.82-3.89 (m, 6H), 3.94 (dd, J=6.3, 9.5 Hz, 1H), 4.07-4.14 (m, 2H), 4.96 (d, J=9.4 Hz, 1H), 4.98-5.01 (m, 1H), 5.53-5.56 (m, 1H), 5.64-5.68 (m, 2H), 6.52-6.53 (m, 2H), 7.18-7.27 (m, 5H), 7.76 (d, J=9.4 Hz, 1H); $^{13}$C NMR (125 MHz, CDCl$_3$): δ 24.4, 25.7, 28.3, 32.3, 32.4, 35.6, 45.2, 51.9, 54.9, 55.6, 69.5, 69.9, 70.7, 71.9, 73.2, 101.9, 104.9, 109.2, 119.3, 126.4, 128.0, 128.4, 129.3, 133.4, 133.9, 137.6, 155.3, 158.0, 164.5; ESI (+) HRMS (m/z): [M+H]$^+$ calcd for C$_{32}$H$_{42}$N$_2$O$_9$S, 631.2689. found, 631.2698.

Example 39

14cZ: $^1$H NMR (500 MHz, CDCl$_3$): δ 1.48-1.52 (m, 3H), 1.57-1.72 (m, 4H), 2.10-2.14 (m, 1H), 2.28-2.32 (m, 1H), 2.47-2.51 (m, 1H), 2.78 (dd, J=9, 14 Hz, 1H), 2.87-2.91 (m, 1H), 2.98-3.08 (m, 3H), 3.45-3.3.60 (m, 1H), 3.65-3.71 (m, 1H), 3.80-3.90 (m, 6H), 3.95 (dd, J=6, 9.5 Hz, 1H), 4.07-4.10 (m, 1H), 4.18-4.21 (m, 1H), 4.95 (d, J=9.5 Hz, 1H), 4.98-5.02 (m, 1H), 5.44-5.49 (m, 2H), 5.63 (d, J=5.5 Hz, 1H), 6.51 (dd, J=2.5, 9.8 Hz, 1H), 6.53 (d, J=2 Hz, 1H), 7.18-7.27 (m, 5H), 7.81 (d, J=9 Hz, 1H); $^{13}$C NMR (125 MHz, CDCl$_3$): δ 24.7, 24.8, 25.7, 27.7, 35.5, 45.2, 46.9, 50.2, 54.9, 55.6, 69.5, 69.9, 70.6, 70.7, 73.2, 101.9, 104.8, 109.1, 120.5, 126.4, 127.6, 128.4, 129.3, 132.5, 133.2, 137.6, 155.3, 158.1, 164.6; ESI (+) HRMS (m/z): [M+H]$^+$ calcd for C$_{32}$H$_{42}$N$_2$O$_9$S, 631.2689. found, 631.2706.

Example 40

Inhibitor 14d: Title compound was obtained from 13d and Grubbs 1$^{st}$ gen. cat. as described for 14a in 71% yield after flash-chromatography (2:3 hexanes:EtOAc) as a white solid. $^1$H NMR (500 MHz, CDCl$_3$): δ 1.40-1.47 (m, 1H), 1.58-1.62 (m, 2H), 1.92-1.95 (m, 1H), 2.11-2.15 (m, 1H), 2.28-2.39 (m, 2H), 2.73-2.78 (m, 1H), 2.80-3.05 (m, 6H), 3.64-3.70 (m, 3H), 3.80-3.89 (m, 6H), 3.93-3.96 (m, 2H), 4.12-4.15 (m, 1H), 4.62 (br s, 1H), 4.97-4.99 (m, 1H), 5.11 (d, J=9.2 Hz, 1H), 5.52-5.54 (m, 2H), 5.61 (d, J=5.1 Hz, 1H), 6.46-6.49 (m, 2H), 7.18-7.26 (m, 5H), 7.80 (d, J=9.4 Hz, 1H); $^{13}$C NMR (125 MHz, CDCl$_3$): δ 22.7, 25.1, 25.7, 29.6, 35.5, 41.2, 45.3, 47.8, 50.2, 54.8, 55.6, 65.9, 69.5, 70.1, 70.7, 73.2, 101.0, 104.3, 109.2, 118.7, 123.3, 126.4, 128.4, 129.3, 133.4, 133.6, 137.5, 155.4, 157.8, 164.7; ESI (+) HRMS (m/z): [M+H]$^+$ calcd for C$_{31}$H$_{40}$N$_2$O$_9$S, 617.2533. found, 617.2534.

Example 41

Inhibitor 14e: Title compound was obtained from 13e and Grubbs 2$^{nd}$ gen. cat. as described for 14a in 52% yield after flash-chromatography (2:3 hexanes:EtOAc) as a white solid. $^1$H NMR (500 MHz, CDCl$_3$): δ 1.46-1.51 (m, 1H), 1.60-1.76 (m, 4H), 1.88-1.92 (m, 1H), 2.23-2.37 (m, 2H), 2.79 (dd, J=9, 14 Hz, 1H), 2.88-3.01 (m, 2H), 3.10-3.13 (m, 1H), 3.66-3.72 (m, 2H), 3.72-3.89 (m, 5H), 3.92-3.99 (m, 2H), 4.07-4.15 (m, 2H), 4.94 (d, J=8.5 Hz, 1H), 5.00-5.04 (m, 1H), 5.52-5.54 (m, 2H), 5.64 (d, J=5.1 Hz, 1H), 6.43 (d, J=2 Hz, 1H), 6.49-6.51 (m, 1H), 7.16-7.28 (m, 5H), 7.81 (d, J=9 Hz, 1H); $^{13}$C NMR (125 MHz, CDCl$_3$): δ 25.7, 26.3, 26.5, 29.6, 35.5, 43.9, 45.2, 50.7, 54.7, 55.6, 69.5, 69.7, 70.7, 73.3, 100.0, 103.9, 109.2, 117.7, 122.9, 128.4, 129.3, 133.7, 135.1, 137.4, 155.3, 157.7, 164.9; ESI (+) HRMS (m/z): [M+Na]$^+$ calcd for C$_{31}$H$_{40}$N$_2$O$_9$S, 639.2352. found, 639.2345.

Example 42

Inhibitor 14f: Title compound was obtained from 13f and Grubbs 2$^{nd}$ gen. cat. as described for 14a in 81% yield after flash-chromatography (2:3 hexanes:EtOAc) as a white solid. $^1$H NMR (500 MHz, CDCl$_3$): δ 1.40-1.47 (m, 1H), 1.58-1.62 (m, 2H), 1.92-1.95 (m, 1H), 2.11-2.15 (m, 1H), 2.28-2.39 (m, 2H), 2.73-2.78 (m, 1H), 2.80-3.05 (m, 6H), 3.64-3.70 (m, 3H), 3.80-3.89 (m, 6H), 3.93-3.96 (m, 2H), 4.12-4.15 (m, 1H), 4.62 (br s, 1H), 4.97-4.99 (m, 1H), 5.11 (d, J=9.2 Hz, 1H), 5.52-5.54 (m, 2H), 5.61 (d, J=5.1 Hz, 1H), 6.46-6.49 (m, 2H), 7.18-7.26 (m, 5H), 7.80 (d, J=9.4 Hz, 1H); $^{13}$C NMR (125 MHz, CDCl$_3$): δ 22.7, 25.1, 25.7, 29.6, 35.5, 41.2, 45.3, 47.8, 50.2, 54.8, 55.6, 65.9, 69.5, 70.1, 70.7, 73.2, 101.0, 104.3, 109.2, 118.7, 123.3, 126.4, 128.4, 129.3, 133.4, 133.6, 137.5, 155.4, 157.8, 164.7; ESI (+) HRMS (m/z): [M+H]$^+$ calcd for C$_{30}$H$_{38}$N$_2$O$_9$S, 603.2376. found, 603.2369.

Example 43

Inhibitor 14g: Title compound was obtained from 13g and Grubbs 2$^{nd}$ gen. cat. as described for 14a in 81% yield after flash-chromatography (2:3 hexanes:EtOAc) as a white solid. $^1$H NMR (500 MHz, CDCl$_3$): δ 1.47-1.55 (m, 1H), 1.64-1.70 (m, 2H), 2.51-2.54 (m, 1H), 2.73-2.78 (m, 1H), 2.84-3.94 (m, 2H), 3.04-3.11 (m, 2H), 3.19 (d, J=13.6 Hz, 1H), 3.70-3.75 (m, 2H), 3.86 (s, 3H), 3.94-3.99 (m, 4H), 4.07-4.08 (m, 1H), 4.18 (br s, 1H), 4.58 (s, 1H), 5.02-5.06 (m, 1H), 5.12 (s, 1H), 5.61 (d, J=5 Hz, 1H), 5.76-5.82 (m, 1H), 5.88-5.93 (m, 1H), 6.35 (d, J=1.1 Hz, 1H), 6.51 (dd, J=1.5, 8.7 Hz, 1H), 7.20-7.31 (m, 5H), 7.79 (d, J=8.8 Hz, 1H); $^{13}$C NMR (125 MHz, CDCl$_3$): δ 25.8, 26.7, 35.4, 43.6, 45.3, 47.1, 55.1, 55.7, 67.4, 69.6, 70.8, 73.3, 99.4, 104.1, 109.2, 120.5, 126.5, 126.9, 128.5, 129.4, 131.2, 132.0, 137.6, 155.6, 157.4, 164.7; ESI (+) HRMS (m/z): [M+Na]$^+$ calcd for C$_{29}$H$_{36}$N$_2$O$_9$S, 611.2039. found, 611.2040.

Example 44

Inhibitor 14h: Title compound was obtained from 13h and Grubbs 2$^{nd}$ gen. cat. as described for 14a in 79% yield after flash-chromatography (2:3 hexanes:EtOAc) as a white solid. $^1$H NMR (400 MHz, CDCl$_3$): δ 1.45-1.51 (m, 1H), 1.60-1.68 (m, 2H), 2.80-2.90 (m, 2H), 3.00-3.12 (m, 3H), 3.53 (br s, 1H), 3.66-3.71 (m, 2H), 3.83 (s, 4H), 3.92-3.95 (m, 3H), 4.88-5.01 (m, 3H), 5.13 (d, J=8.3 Hz, 1H), 6.59-6.64 (m, 2H), 7.19-7.26 (m, 5H), 7.74 (d, J=8.7 Hz, 1H); $^{13}$C NMR (125 MHz, CDCl$_3$): δ 25.7, 29.6, 35.3, 43.9, 45.2, 47.8, 55.1, 55.7, 69.5, 69.7, 70.7, 71.1, 73.3, 104.5, 107.2, 109.2, 123.4, 126.1, 126.4, 128.4, 129.3, 131.3, 131.5, 137.6, 155.6, 157.7, 164.5; ESI (+) HRMS (m/z): [M+Na]$^+$ calcd for C$_{28}$H$_{34}$N$_2$O$_9$S, 597.1883. found, 597.1887.

Example 45

Inhibitor 15a: To a stirring solution of 14a (10 mg, 0.015 mmol) in EtOAc (2 mL) was added 10% Pd on carbon and the reaction was stirred under H$_2$ atmosphere for 12 h. After this time the reaction was filtered through a pad of celite and solvent was evaporated under reduced pressure. The residue was then purified by flash-chromatography to give 15a (9.2 mg, 93% yield) as a white solid. $^1$H NMR (500 MHz, CDCl$_3$): δ 1.40-1.47 (m, 3H), 1.49-1.52 (m, 2H), 1.71-1.83 (m, 4H), 2.75 (dd, J=9.5, 13.7 Hz, 1H), 2.86-2.91 (m, 1H), 3.01-3.10

(m, 3H), 3.64-3.71 (m, 2H), 3.85 (s, 1H), 3.94 (dd, J=6.4, 9.5 Hz, 1H), 4.01-4.04 (m, 1H), 4.10-4.16 (m, 1H), 4.94 (d, J=9.2 Hz, 1H), 5.01-5.15 (m, 1H), 5.67 (d, J=5.1 Hz, 1H), 6.52-6.54 (m, 2H), 7.19-7.29 (m, 5H), 7.85 (d, J=9 Hz, 1H); $^{13}$C NMR (125 MHz, CDCl$_3$): δ 22.4, 22.9, 23.0, 23.8, 24.2, 25.5, 26.3, 26.4, 28.2, 29.1, 29.4, 29.9, 35.3, 45.1, 51.3, 52.8, 54.6, 55.4, 69.2, 69.3, 69.5, 70.5, 71.9, 73.1, 100.2, 103.9, 109.0, 118.7, 126.3, 128.2, 129.1, 133.5, 137.3, 155.1, 157.9, 164.6; ESI (+) HRMS (m/z): [M+Na]$^+$ calcd for C$_{34}$H$_{48}$N$_2$O$_9$S, 683.2978. found, 683.2984.

Example 46

Inhibitor 15b: Title compound was obtained from 14b as described for 15a in 90% yield after flash-chromatography (2:3 hexanes:EtOAc) as a white solid. $^1$H NMR (500 MHz, CDCl$_3$): δ 1.30-1.47 (m, 8H), 1.57-1.70 (m, 5H), 1.72-1.79 (m, 1H), 1.82-1.87 (m, 2), 2.77 (dd, J=10, 14 Hz, 1H), 2.86-2.91 (m, 1H), 3.00 (dd, J=4.5, 14 Hz, 1H), 3.05 (d, J=2.5, 15 Hz, 1H), 3.14-3.23 (m, 2H), 3.56-3.62 (m, 2H), 3.65-3.72 (m, 2H), 3.81-3.90 (m, 6H), 3.94 (dd, J=6.5, 10 Hz, 1H), 4.05-4.15 (m, 2H), 4.96 (d, J=9.5 Hz, 1H), 4.99-5.02 (m, 1H), 5.64 (d, J=5.5 Hz, 1H), 6.49-6.52 (m, 2H), 7.17-7.27 (m, 5H), 7.82 (d, J=9.5 Hz, 1H); $^{13}$C NMR (125 MHz, CDCl$_3$): δ 23.2, 24.2, 24.9, 25.2, 25.7, 26.1, 27.6, 28.9, 35.4, 45.2, 49.2, 52.7, 54.8, 55.6, 68.9, 69.5, 70.7, 71.7, 73.2, 100.5, 104.2, 109.2, 118.5, 126.4, 128.4, 129.3, 133.8, 137.5, 155.3, 158.1, 164.8; ESI (+) HRMS (m/z): [M+Na]$^+$ calcd for C$_{33}$H$_{46}$N$_2$O$_9$S, 669.2822. found, 669.2828.

Example 47

Inhibitor 15c: Title compound was obtained from 14c as described for 15a in 90% yield after flash-chromatography (2:3 hexanes:EtOAc) as a white solid. $^1$H NMR (500 MHz, CDCl$_3$): δ 1.35-1.39 (m, 3H), 1.40-1.54 (m, 5H), 1.60-1.66 (m, 7H), 1.85-1.98 (m, 2), 2.78 (dd, J=9.1, 14 Hz, 1H), 2.88-2.91 (m, 1H), 2.97-3.03 (m, 1H), 3.06-3.14 (m, 1H), 3.39-3.43 (m, 1H), 3.50-3.56 (m, 1H), 3.66-3.72 (m, 3H), 3.82-3.85 (m, 6H), 3.95 (dd, J=6.3, 9.6 Hz, 1H), 4.07-4.10 (m, 2H), 4.95-5.03 (m, 2H), 5.64 (d, J=5 Hz, 1H), 6.50-6.53 (m, 2H), 7.17-7.27 (m, 5H), 7.82 (d, J=9 Hz, 1H); $^{13}$C NMR (125 MHz, CDCl$_3$): δ 22.6, 23.5, 23.9, 24.6, 25.3, 25.7, 26.1, 29.3, 29.6, 31.8, 35.5, 44.8, 45.2, 46.5, 51.0, 54.8, 55.6, 69.5, 70.1, 70.7, 70.8, 73.2, 100.9, 104.3, 109.2, 118.5, 126.4, 128.4, 129.4, 133.9, 137.5, 155.3, 158.2, 164.8; ESI (+) HRMS (m/z): [M+Na]$^+$ calcd for C$_{32}$H$_{44}$N$_2$O$_9$S, 655.2668. found, 655.2667.

Example 48

Inhibitor 15d: Title compound was obtained from 14d or 14e as described for 15a in 94% yield after flash-chromatography (2:3 hexanes:EtOAc) as a white solid. $^1$H NMR (500 MHz, CDCl$_3$): δ 1.33-1.54 (m, 6H), 1.57-1.74 (m, 3H), 1.86-1.94 (m, 2H), 2.77 (dd, J=9.5, 14 Hz, 1H), 2.86-2.90 (m, 1H), 2.96-3.08 (m, 3H), 3.24-3.29 (m, 1H), 3.64-3.72 (m, 2H), 3.74-3.86 (m, 7H), 3.94-4.00 (m, 2H), 4.15-4.22 (m, 2H), 4.92 (d, J=9.2 Hz, 1H), 4.97-5.02 (m, 1H), 5.62 (d, J=5.2 Hz, 1H), 6.48 (d, J=2.1 Hz, 1H), 6.52 (dd, J=2, 8.9 Hz, 1H), 7.17-7.27 (m, 5H), 7.87 (d, J=8.6 Hz, 1H); $^{13}$C NMR (125 MHz, CDCl$_3$): δ 23.2, 25.0, 25.6, 26.1, 26.3, 29.6, 35.4, 42.9, 45.2, 48.5, 54.7, 55.6, 69.3, 69.5, 70.7, 73.3, 99.9, 103.8, 109.1, 117.1, 126.4, 128.4, 129.3, 134.6, 137.4, 155.1, 157.7, 165.2; ESI (+) HRMS (m/z): [M+Na]$^+$ calcd for C$_{31}$H$_{42}$N$_2$O$_9$S, 641.2509. found, 641.2512.

Example 49

Inhibitor 15e: Title compound was obtained from 14f as described for 15a in 93% yield after flash-chromatography (2:3 hexanes:EtOAc) as a white solid. $^1$H NMR (500 MHz, CDCl$_3$): δ 1.33-1.48 (m, 4H), 1.56-1.66 (m, 3H), 1.67-1.71 (m, 2H), 1.83-1.86 (m, 1H), 2.04-2.12 (m, 2H), 2.74 (dd, J=9.7, 14 Hz, 1H), 2.83-2.99 (m, 4H), 3.18 (br s, 1H), 3.64-3.71 (m, 2H), 3.76-3.85 (m, 6H), 3.89-3.99 (m, 3H), 4.08 (br s, 1H), 4.19-4.23 (m, 1H), 4.96-5.00 (m, 2H), 5.63 (d, J=5 Hz, 1H), 6.45 (d, J=2 Hz, 1H), 6.50 (dd, J=2.5, 9 Hz, 1H), 7.15-7.26 (m, 5H), 7.88 (d, J=9 Hz, 1H); $^{13}$C NMR (125 MHz, CDCl$_3$): δ 22.2, 24.4, 24.6, 25.7, 25.8, 35.4, 45.2, 46.8, 51.8, 54.7, 55.7, 69.2, 69.6, 70.5, 70.8, 73.3, 99.8, 103.9, 109.2, 117.5, 126.5, 128.4, 129.3, 137.4, 155.2, 157.8, 165.3; ESI (+) HRMS (m/z): [M+Na]$^+$ calcd for C$_{30}$H$_{40}$N$_2$O$_9$S, 605.2533. found, 605.2526.

Example 50

Inhibitor 15f: Title compound was obtained from 14g as described for 15a in 90% yield after flash-chromatography (2:3 hexanes:EtOAc) as a white solid. $^1$H NMR (500 MHz, CDCl$_3$): δ 1.46-1.50 (m, 3H), 1.59-1.67 (m, 4H), 1.96-2.04 (m, 2H), 2.81-2.91 (m, 2H), 3.03 (dd, J=3, 14 Hz, 1H), 3.07-3.12 (m, 2H), 3.83-3.91 (m, 6H), 3.93-4.02 (m, 3H), 4.25 (br s, 1H), 4.98-5.02 (m, 2H), 5.63 (d, J=5 Hz, 1H), 6.40 (d, J=2 Hz, 1H), 6.49 (dd, J=2, 9 Hz, 1H), 7.18-7.28 (m, 5H), 7.76 (d, J=9 Hz, 1H); $^{13}$C NMR (125 MHz, CDCl$_3$): δ 22.4, 24.4, 25.3, 25.7, 35.4, 43.1, 45.2, 47.3, 54.9, 55.6, 69.5, 70.1, 70.6, 73.2, 100.5, 104.2, 109.2, 121.4, 126.4, 128.4, 129.3, 131.5, 137.5, 155.4, 157.7, 165.6; ESI (+) HRMS (m/z): [M+H]$^+$ calcd for C$_{29}$H$_{38}$N$_2$O$_9$S, 591.2376. found, 591.2381.

Example 51

Inhibitor 15g: Title compound was obtained from 14h as described for 15a in 92% yield after flash-chromatography (2:3 hexanes:EtOAc) as a white solid. $^1$H NMR (500 MHz, CDCl$_3$): δ 1.39-1.51 (m, 3H), 1.60-1.68 (m, 4H), 1.72-1.81 (m, 2H), 2.82-2.92 (m, 2H), 3.00-3.06 (m, 3H), 3.66-3.71 (m, 3H), 3.80-3.87 (m, 6H), 3.95 (dd, J=6, 9.5 Hz, 1H), 4.33-4.42 (m, 2H), 4.98-5.02 (m, 2H), 5.63 (d, J=5 Hz, 1H), 6.62-6.64 (m, 2H), 7.18-7.28 (m, 5H), 7.77 (d, J=10.5 Hz, 1H); $^{13}$C NMR (125 MHz, CDCl$_3$): δ 24.4, 25.0, 25.7, 35.3, 45.2, 46.5, 55.6, 69.5, 70.6, 73.2, 73.9, 105.6, 107.3, 109.1, 126.4, 128.4, 129.3, 130.9, 137.3, 155.5, 157.4, 164.4; ESI (+) HRMS (m/z): [M+H]$^+$ calcd for C$_{28}$H$_{36}$N$_2$O$_9$S, 577.2220. found, 577.2222.

Example 52 tert-Butyl (2S,3R)-4-(2,2-dimethylpent-4-enylamino)-3-hydroxy-1-phenylbutan-2-ylcarbamate (17a): Under argon, combined amine 16a (1.58 g, 4.33 mmol) and epoxide 8 (304 mg, 1.15 mmol) and heated to 60° C. for 4 h. Let stir overnight at rt. Purified by silica chromatography (3:97 MeOH:CH$_2$Cl$_2$) to give 370 mg (98.3% yield) of product as a clear oil that solidified upon refrigeration. TLC 5:95 MeOH:CH$_2$Cl$_2$, R$_f$=0.2, visualized with ninhydrin; mp 35-37° C. [α]$_D^{20}$ +0.9 (c 0.14, CHCl$_3$); $^1$H NMR (CDCl$_3$, 400 MHz): δ 7.26 (m, 5H), 5.81 (m, 1H), 5.03 (m, 2H), 4.79 (d, J=9.2 Hz, 1H), 3.82 (m, 1H), 3.45 (m, 1H), 2.98 (dd, J=4.8, 9.2 Hz, 1H), 2.87 (dd, J=8, 14.8 Hz, 1H), 2.69 (d, J=4.8 Hz, 2H), 2.35 (s, 2H), 2.01 (d, J=7.6 Hz, 2H), 1.36 (s, 9H), 0.90 (s, 6H); $^{13}$C NMR (CDCl$_3$, 100 MHz): δ 155.8, 137.9, 135.2, 129.4, 128.3, 126.2, 116.9, 79.1, 70.3, 60.1, 54.3, 52.1, 44.5, 36.8, 34.3, 29.6, 25.4, 25.4; FTIR (NaCl) $v_{max}$=3349, 3064, 3027, 2958, 2928, 1693, 1638, 1604, 1498, 1455, 1391, 1366, 1250, 1171, 1126, 1042, 1017, 913, 742, 700 cm$^{-1}$; ESI (+) MS m/z (relative intensity): 376.06 (100%).

Example 53 tert-Butyl (2S,3R)-4-(N-(2,2-dimethylpent-4-enyl)-2-(hex-5-enyloxy)-4-methoxyphenylsulfonamido)-3-hydroxy-1-phenylbutan-2-ylcarbamate (18a): Combined amine 17a (188.3 mg, 0.5 mmol) and sulfonyl chloride 7 (182.9 mg, 0.6 mmol) into a reaction flask and cooled to 0° C. Under argon, added pyridine (8 mL, freshly distilled over KOH) and allowed the reaction to come to rt while stirring. The reaction turned orange and was allowed to stir overnight. The reaction was condensed under reduced pressure, washed with sat. Cu$_2$SO$_4$ (10 mL), and the product extracted into dichloromethane (3×20 mL). The organic layer was washed with H$_2$O (10 mL), brine (2×5 mL), dried over sodium sulfate and purified by silica chromatography (20:80 EtOAc:Hexane) to give 179.9 mg (55.8% yield) of product as a clear oil. TLC 30:70 EtOAc:Hexane, R$_f$=0.46, UV and iodine to visualize; $[\alpha]_D^{20}$ +18.3 (c 0.12, CHCl$_3$); $^1$H NMR (CDCl$_3$, 400 MHz): δ 7.78 (d, J=8.4 Hz, 1H), 7.2 (m, 5H), 6.47 (m, 2H), 5.79 (m, 2H), 5.00 (m, 4H), 4.40 (d, J=8.8 Hz, 1H), 4.00 (m, 2H), 3.83 (s, 3H), 3.80 (m, 1H), 3.66 (m, 1H), 3.20 (m, 4H), 2.86 (dd, J=4.8, 14.4 Hz, 1H), 2.77 (dd, J=8, 13.2 Hz, 1H), 2.12 (q, J=6.8 Hz, 2H), 1.99 (d, J=7.2 Hz, 2H), 1.86 (p, J=8 Hz, 2H), 1.59 (m, 2H), 1.31 (s, 9H), 1.25 (m, 1H), 0.92 (s, 3H), 0.90 (s, 3H); $^{13}$C NMR (CDCl$_3$, 100 MHz): δ 164.8, 157.5, 155.5, 138.0, 137.6, 134.7, 134.0, 129.4, 128.3, 126.2, 118.5, 117.5, 115.1, 104.2, 100.1, 79.3, 72.0, 69.1, 62.4, 55.6, 55.5, 54.2, 45.2, 35.8, 33.2, 28.4, 28.2, 28.0, 25.6, 25.5, 25.0; FTIR (NaCl) $v_{max}$=3412, 2924, 2852, 1701, 1596, 1496, 1456, 1391, 1367, 1326, 1254, 1206, 1158, 1074, 1030, 914 cm$^{-1}$; ESI (+) LRMS m/z (relative intensity): 667.12 (100%); ESI (+) HRMS (m/z): [M+Na]$^+$ calcd for C$_{35}$H$_{52}$N$_2$O$_7$S 667.3393. found, 667.3399.

Example 54

(3R,3aS,6aR)-Hexahydrofuro[2,3-b]furan-3-yl (2S,3R)-4-(N-(2,2-dimethylpent-4-enyl)-2-(hex-5-enyloxy)-4-methoxyphenylsulfonamido)-3-hydroxy-1-phenylbutan-2-ylcarbamate (19a): Dissolved 18a (180 mg, 0.28 mmol) into CH$_2$Cl$_2$ (5 mL) and cooled to 0° C. Trifluoroacetic acid (1.5 mL) was added dropwise while stirring. The reaction was allowed to warm to rt and stir overnight. Solvents were removed under reduced pressure. The residue was made basic with a mixture of sat. NaHCO$_3$ (1 mL) and 1N NaOH (1 mL) and extracted with ether (5×5 mL). Solvents were removed under reduced pressure to afford the crude amine product. This amine (0.28 mmol) was dissolved into MeCN (20 mL) and mixed with carbonate 12 (92 mg, 0.31 mmol) under argon. DIPEA (1 mL) and pyridine (1 mL) were was added dropwise and the reaction was allowed to stir overnight at rt. After stirring for 2 days, the solvents were removed under reduced pressure and the crude material purified by silica chromatography (50:50 EtOAc:Hexane) to give 143.5 mg (73.1% yield over two steps) of product as a white tacky solid. TLC 50:50 EtOAc:Hexane, R$_f$=0.27, UV and iodine visualization; m.p.=49-52° C.; $[\alpha]_D^{20}$ +3.9 (c 1.03, CHCl$_3$); $^1$H NMR (CDCl$_3$, 400 MHz) δ 7.79 (d, J=8.4 Hz, 1H), 7.18 (m, 5H), 6.48 (m, 2H), 5.77 (m, 2H), 5.60 (d, J=5.2 Hz, 1H), 5.02 (m, 4H), 4.87 (d, J=9.6 Hz, 1H), 4.03 (m, 2H), 3.91 (m, 3H), 3.83 (s, 3H), 3.78 (m, 2H), 3.63 (m, 2H), 3.29 (m, 2H), 3.08 (m, 2H), 2.94 (dd, J=4, 14.4 Hz, 1H), 2.84 (m, 1H), 2.69 (dd, J=9.6, 14 Hz), 2.11 (m, 2H), 2.02 (m, 3H), 1.86 (m, 2H), 1.58 (m, 3H), 1.35 (m, 1H), 0.91 (s, 3H), 0.90 (s, 3H); $^{13}$C NMR (CDCl$_3$, 100 MHz) δ 164.9, 157.6, 155.0, 137.9, 137.5, 134.5, 134.0, 129.2, 128.3, 126.3, 118.0, 117.6, 115.0, 109.2, 104.3, 100.1, 73.1, 72.3, 70.6, 69.5, 69.2, 62.6, 55.6, 55.6, 54.8, 45.2, 45.1, 35.7, 35.5, 33.2, 28.3, 25.7, 25.5, 25.4, 24.9; FTIR (NaCl) $v_{max}$=701.6, 767.6, 919.1, 1021.0, 1074.3, 1140.9, 1206.5, 1256.3, 1323.6, 1595.4, 1722.9, 2922.7, 2963.6, 3076.2, 3487.2 cm$^{-1}$; ESI (+) MS m/z (relative intensity): 1422.15 (5%), 700.82 (100%), 588.84 (26%), 545.10 (44%); ESI (+) HRMS (m/z): [M+H]$^+$ calcd for C$_{37}$H$_{52}$N$_2$O$_9$S 701.3472. found, 701.3473.

Example 55

Inhibitors 20a and 21a: 19a (100 mg, 0.143 mmol) was dissolved into CH$_2$Cl$_2$ (90 mL). Grubbs' 2$^{nd}$ gen. cat. (11.8 mg, 0.014 mmol) was added and the reaction was allowed to stir overnight at rt. Solvent was removed under reduced pressure and the material purified by silica chromatography (50:50→75:25 EtOAc:Hexane) to give 92.1 mg (95.7% yield) of product as a mixture of stereoisomers (31:69 Z:E by HPLC) as a white solid. The individual stereoisomers were isolated by reversed-phase HPLC YMC-Pack ODSA (250×10 mm, 5 micron); flow rate=1.5 mL/min; isocratic 80:20 MeOH:H$_2$O; T=25° C.; λ=210 nm, R$_t$Z=17 min, R$_t$E=18 min). 21a: $[\alpha]_D^{20}$ −0.8 (c 2.36, CHCl$_3$); $^1$H NMR (CDCl$_3$, 800 MHz) δ 7.79 (d, J=8.8 Hz, 1H), 7.24 (t, J=8 Hz, 2H), 7.18 (t, J=7.2 Hz, 1H), 7.12 (d, J=7.2 Hz, 2H), 6.50 (dd, J=1.6, 8.8 Hz, 1H), 6.47 (m, 1H), 5.68 (m, 1H), 5.62 (d, J=5.6 Hz, 1H), 5.60 (d, J=1H), 4.98 (q, J=7.2 Hz, 1H), 4.71 (d, J=9.6 Hz, 1H), 4.04-3.88 (m, 4H), 3.84 (s, 3H), 3.82 (m, 1H), 3.77 (m, 1H), 3.71 (dd, J=6.4, 13.6 Hz, 1H), 3.68 (m, 1H), 3.64 (m, 1H), 3.11 (dd, J=9.6, 15.2 Hz, 1H), 2.97 (dd, J=2.4, 15.2 Hz, 1H), 2.92 (dd, J=4, 14.4 Hz, 1H), 2.86 (q, J=7.2 Hz, 1H), 2.68 (dd, J=9.6, 14.4 Hz, 1H), 2.10-1.94 (m, 4H), 1.90-1.72 (m, 4H), 1.58 (m, 1H), 1.39 (m, 1H), 1.25 (s, 1H), 1.24 (t, J=6.4 Hz, 1H), 1.12 (s, 3H), 1.05 (s, 3H); $^{13}$C NMR (CDCl$_3$, 125 MHz) δ 164.9, 158.1, 155.1, 137.5, 134.5, 133.6, 129.3, 128.5, 128.4, 126.5, 117.8, 109.3, 104.4, 100.6, 73.3, 72.2, 70.7, 69.7, 69.6, 63.0, 56.1, 55.7, 54.7, 46.1, 45.3, 35.8, 35.6, 29.7, 29.6, 29.2, 27.6, 26.1, 25.7; FTIR (film, NaCl) $v_{max}$=3445, 3343, 2926, 1720, 1596, 1575, 1532, 1494, 1469, 1445, 1429, 1390, 1369, 1325, 1256, 1207, 1172, 1141, 1074, 1021, 988, 964, 926, 896, 841, 753, 702, 665, 643 cm$^{-1}$; ESI (+) LRMS m/z (relative intensity): 695.30 (70%), 1366.74 (100%); ESI (+) HRMS (m/z): [M+Na]$^+$ calcd for C$_{35}$H$_{48}$N$_2$O$_9$S 695.2978. found, 695.2989.

Example 56

20a: $[\alpha]_D^{20}$ −0.5 (c 0.99, CHCl$_3$); $^1$H NMR (CDCl$_3$, 800 MHz) δ 7.81 (d, J=8.8 Hz, 1H), 7.23 (t, J=8 Hz, 2H), 7.18 (d, J=7.2 Hz, 1H), 7.13 (d, J=7.2 Hz, 2H), 6.51 (dd, J=2.4, 8.8 Hz, 1H), 6.47 (d, J=2.4 Hz, 1H), 5.65 (q, J=8.8 Hz, 1H), 5.62 (d, J=5.6 Hz, 1H), 5.53 (q, J=8.8 Hz, 1H), 4.98 (q, J=5.6 Hz, 1H), 4.74 (d, J=9.6 Hz, 1H), 4.08 (t, J=4.8 Hz, 2H), 3.96 (m, 1H), 3.93 (dd, J=6.4, 9.6 Hz, 1H), 3.85 (s, 3H), 3.82 (dt, J=2.4, 8.8 Hz, 1H), 3.79 (m, 1H), 3.68 (dd, J=6.4, 9.6 Hz, 1H), 3.65 (m, 1H), 3.08 (dd, J=8.8, 15.2 Hz, 1H), 2.93 (dd, J=4, 14.4 Hz, 1H), 2.91 (dd, J=0.8, 15.2 Hz, 1H), 2.86 (m, 1H), 2.70 (dd, J=9.6, 14.4 Hz, 1H), 2.20-1.98 (m, 4H), 1.90 (br s, 2H), 1.76-1.62 (m, 2H), 1.57 (m, 1H), 1.38 (m, 1H), 1.25 (s, 3H), 1.13 (s, 3H), 1.07 (s, 3H); $^{13}$C NMR (CDCl$_3$, 125 MHz) δ 164.9, 157.9, 155.1, 137.5, 134.8, 131.0, 129.3, 128.4, 126.7, 126.5, 117.3, 109.3, 104.1, 100.2, 73.3, 72.6, 70.7, 69.6, 68.8, 64.1, 56.1, 55.7, 54.7, 45.3, 40.5, 36.1, 35.6, 29.7, 27.4, 26.7, 26.1, 25.8, 25.3; FTIR (film, NaCl) $v_{max}$=3344, 2925, 1718, 1595, 1575, 1534, 1493, 1445, 1388, 1325, 1257, 1206, 1171, 1141, 1074, 1021, 925, 892, 933, 756, 702 cm$^{-1}$; ESI (+) LRMS m/z (relative intensity): 695.28 (95%), 1366.73 (100%); ESI (+) HRMS (m/z): [M+Na]$^+$ calcd for C$_{35}$H$_{48}$N$_2$O$_9$S 695.2978. found, 695.2970.

Example 57

22a: The corresponding olefin 20a or 21a (21.6 mg, 0.032 mmol) was dissolved into ethyl acetate (5 mL). Pd/C (10%) was added and the reaction flask evacuated with H$_2$ gas. After stirring overnight, the reaction was filtered over celite and purified by silica chromatography (50:50→75:25 EtOAc: Hexane) to give 19.49 mg (90.2% yield) of the desired product. TLC 70:30 EtOAc:Hexane, R$_f$=0.63, UV and/or phosphomolybdic acid used to visualize; [α]$_D^{20}$ −2.9 (c 0.70, CHCl$_3$); $^1$H NMR (CDCl$_3$, 800 MHz) δ 7.82 (d, J=8.8 Hz, 1H), 7.24 (t, J=8 Hz, 2H), 7.18 (t, J=7.2 Hz, 1H), 7.15 (d, J=7.2 Hz, 2H), 6.51 (m, 2H), 5.63 (d, J=4.8 Hz, 1H), 4.98 (q, J=5.6 Hz, 1H), 4.75 (d, J=9.6 Hz, 1H), 4.10 (m, 1H), 4.07 (m, 1H), 3.94 (m, 1H), 3.93 (dd, J=6.4, 9.6 Hz, 1H), 3.86 (s, 3H), 3.82 (dt, J=1.6, 8 Hz, 1H), 3.80 (m, 1H), 3.70-3.63 (m, 2H), 3.19 (dd, J=9.6, 15.2 Hz, 1H), 3.01 (dd, J=1.6, 15.2 Hz, 1H), 2.98 (dd, J=4, 14.4 Hz, 1H), 2.87 (m, 1H), 2.71 (dd, J=9.6, 14.4 Hz, 1H), 1.81 (m, 2H), 1.69 (m, 1H), 1.64-1.54 (m, 3H), 1.45 (m, 4H), 1.38 (m, 3H), 1.27 (m, 2H), 1.18 (m, 1H), 1.03 (s, 3H), 0.97 (s, 3H); $^{13}$C NMR (CDCl$_3$, 125 MHz) δ 164.9, 158.1, 155.1, 137.5, 135.6, 129.3, 128.4, 126.5, 117.7, 109.3, 104.0, 100.2, 73.3, 72.5, 70.7, 69.6, 68.9, 61.8, 56.1, 55.7, 54.8, 45.3, 39.8, 35.8, 35.7, 28.3, 27.4, 26.2, 25.8, 25.4, 25.0, 22.3, 19.6; FTIR (NaCl) ν$_{max}$=3449, 3333, 2930, 1718, 1596, 1534, 1444, 1325, 1257, 1206, 1140, 1074, 1020, 755, 701 cm$^{-1}$; ESI (+) LRMS m/z (relative intensity): 697.10 (27%), 674.81 (100%); ESI (+) HRMS (m/z): [M+H]$^+$ calcd for C$_{35}$H$_{50}$N$_2$O$_9$S 675.3315. found, 675.3318.

Example 58 tert-Butyl (2S,3R)-3-hydroxy-4-(2-methylpent-4-enylamino)-1-phenylbutan-2-ylcarbamate (17b and 17c): 2-methylpent-4-en-1-amine (4.6 mmol) and epoxide 8 (361.5 mg, 1.3 mmol) were weighed into a flask. The flask was evacuated with argon and the reaction allowed to stir at 60° C. overnight. The crude material was purified by silica chromatography (3:97 MeOH:CH$_2$Cl$_2$) to give 470 mg (94.6%) of product as a white solid as a mix of diastereomers (50:50 by NMR). TLC 10:90 MeOH:CH$_2$Cl$_2$ R$_f$=0.1 visualized with ninhydrin stain; mp 89-90° C.; [α]$_D^{20}$ +5.4 (c 2.58, CHCl$_3$); $^1$H NMR (CDCl$_3$, 400 MHz): δ 7.29 (m, 4H), 7.22 (m, 6H), 5.77 (m, 2H), 5.04 (m, 4H), 4.77-4.55 (m, 2H), 3.85-3.59 (m, 4H), 3.45 (m, 2H), 3.01-2.6 (m, 10H), 2.52 (dd, J=6, 12 Hz, 2H), 2.40 (dd, J=6.8, 11.6 Hz, 2H), 2.13 (m, 2H), 1.92 (m, 2H), 1.67 (m, 2H), 1.35 (s, 18H), 0.92 (d, J=2.4, 3H), 0.91 (d, J=2 Hz, 3H; $^{13}$C NMR (CDCl$_3$, 100 MHz): δ 155.9, 137.9, 137.0, 129.5, 128.4, 126.3, 116.0, 79.3, 70.6, 55.7, 54.1, 51.4, 51.4, 39.2, 39.2, 36.7, 33.2, 28.3, 17.8; FTIR (NaCl) ν$_{max}$=3365, 2976, 2925, 1683, 1520, 1455, 1391, 1367, 1252, 1171, 1017, 912, 755, 701 cm$^{-1}$; ESI (+) LRMS m/z (relative intensity): 363.03 (100%). ESI (−) LRMS m/z (relative intensity): 361.28 (100%). Pure 17c was prepared in a similar fashion by using enantiopure (S)-2-methylpent-4-en-1-amine. $^1$H NMR (CDCl$_3$, 400 MHz): δ

Example 59 tert-Butyl (2S,3R)-4-(2-(hex-5-enyloxy)-4-methoxy-N-(2-methylpent-4-enyl)phenylsulfonamido)-3-hydroxy-1-phenylbutan-2-ylcarbamate (18b and 18c): Under argon, combined amines 17b and 17c (165.6 mg, 0.46 mmol) with sulfonyl chloride 7 (167 mg, 0.55 mmol) and cooled to 0° C. Pyridine (5 mL) was added and the solution stirred overnight. Solvents were removed by reduced pressure and the crude material purified by silica chromatography (20:80 EtOAc: Hexane) to give 148 mg (51% yield) of product as a clear oil. TLC 40:60 EtOAc:Hexane R$_f$=0.58 visualized with UV/iodine; [α]$_D^{20}$ −1.8 (c 0.67, CHCl$_3$); $^1$H NMR (CDCl$_3$, 300 MHz): δ 7.83 (d, J=8.7 Hz, 2H), 7.30-7.16 (m, 10H), 6.54-6.44 (m, 4H), 5.87-5.58 (m, 4H), 5.06-4.90 (m, 8H), 4.59 (m, 2H), 4.06-3.94 (m, 5H), 3.84 (s, 6H), 3.73 (br, 4H), 3.36-2.80 (m, 12H), 2.26-2.06 (m, 6H), 1.92-1.70 (m, 9H), 1.65-1.52 (m, 4H), 1.33 (s, 18H), 0.88 (d, J=6 Hz, 3H), 0.80 (d, J=6 Hz, 3H); $^{13}$C NMR (CDCl$_3$, 75 MHz): δ 164.7, 157.6, 155.9, 138.1, 137.9, 137.7, 136.3, 133.7, 129.5, 128.3, 126.3, 119.0, 116.3, 115.1, 104.1, 100.2, 79.4, 72.7, 72.3, 69.1, 57.1, 56.8, 55.6, 54.6, 54.4, 53.3, 53.2, 38.7, 35.3, 33.2, 31.9, 31.7, 28.3, 28.2, 25.0, 17.1; FTIR (NaCl) ν$_{max}$=3392, 2929, 1702, 1640, 1596, 1577, 1495, 1445, 1391, 1366, 1326, 1254, 1206, 1171, 1074, 995, 913, 837, 774, 701 cm$^{-1}$; ESI (+) LRMS m/z (relative intensity): 630.68 (100%); ESI (+) HRMS (m/z): [M+H$^+$] calcd for C$_{34}$H$_{50}$N$_2$O$_7$S 631.3417. found, 631.3408. Pure 17c was prepared in a similar fashion using pure 18c. $^1$H NMR (CDCl$_3$, 400 MHz): δ 7.84 (d, J=8.4 Hz, 1H), 7.27 (m, 2H), 7.20 (m, 3H), 6.50 (dd, J=2.4, 8.8 Hz, 1H), 6.46 (d, J=2.4 Hz, 1H), 5.80 (m, 1H), 5.66 (m, 1H), 5.05-4.93 (m, 4H), 4.57 (d, J=7.2 Hz, 1H), 4.03 (t, J=6.8 Hz, 2H), 3.96 (m, 1H), 3.85 (s, 3H), 3.74 (m, 2H), 3.25 (m, 3H), 2.94 (m, 3H), 2.19 (m, 1H), 2.12 (q, J=7.2 Hz, 2H), 1.87 (m, 2H), 1.74 (m, 2H), 1.59 (m, 2H), 1.34 (s, 9H), 0.80 (d, J=6 Hz, 3H); $^{13}$C NMR (CDCl$_3$, 100 MHz): δ 164.7, 157.6, 155.9, 138.1, 137.7, 136.4, 133.7, 129.6, 128.4, 126.3, 119.1, 116.3, 115.1, 104.1, 100.2, 79.5, 72.3, 69.1, 56.9, 55.7, 54.5, 53.2, 38.1, 35.2, 33.3, 31.8, 28.4, 28.2, 25.0, 17.1.

Example 60

(3R,3aS,6aR)-Hexahydrofuro[2,3-b]furan-3-yl (2S,3R)-4-(2-(hex-5-enyloxy)-4-methoxy-N-(2-methylpent-4-enyl)phenylsulfonamido)-3-hydroxy-1-phenylbutan-2-ylcarbamate (19b and 19c): Dissolved 18b and 18c (140 mg, 0.22 mmol) into CH$_2$Cl$_2$ (4.5 mL) and added TFA (1.5 mL). Stirred for 4 hr and quenched with sat. NaHCO$_3$ (1.5 mL). 2N NaOH was added until the solution turned basic. Extracted with ether, washed with brine, and dried over Na$_2$SO$_4$. Solvents were removed under reduced pressure to give crude N-((2R,3S)-3-amino-2-hydroxy-4-phenylbutyl)-2-(hex-5-enyloxy)-4-methoxy-N-(2-methylpent-4-enyl)benzensulfonamide. Under argon, the crude amine was dissolved into MeCN (5 mL). (3R,3aS,6aR)-hexahydrofuro[2,3-b]furan-3-yl 4-nitrophenyl carbonate (71.4 mg, 0.24 mmoL) and DIPEA (0.75 mL) were added and the reaction stirred overnight. Solvents were removed under reduced pressure and the crude material purified by silica chromatography (50:50 EtOAc:Hexane) to give 67.7 mg (45% yield) of product as a clear oil. TLC 50:50 EtOAc:Hexane R$_f$=0.27 visualized by UV and iodine; [α]$_D^{20}$ −5.7 (c 0.17, CHCl$_3$); $^1$H NMR (CDCl$_3$, 400 MHz): δ 7.83 (d, J=8.8 Hz, 2H), 7.24 (m, 4H), 7.18 (m, 6H), 6.50 (m, 4H), 5.85-5.60 (m, 6H), 5.05-4.92 (m, 12H), 4.06-3.62 (m, 24H), 3.40-2.70 (m, 14H), 2.24-1.40 (m, 22H), 0.90 (d, J=6.4 Hz, 3H), 0.80 (d, J=6.4 Hz); $^{13}$C NMR (CDCl$_3$, 100 MHz): δ 164.8, 157.6, 155.3, 138.0, 137.6, 137.5, 136.2, 133.8, 129.3, 128.4, 126.5, 118.8, 118.7, 116.5, 115.1, 109.26, 104.2, 100.3, 73.3, 72.8, 72.3, 70.7, 69.6, 69.2, 57.3, 56.9, 55.7, 55.0, 54.9, 53.4, 53.2, 45.3, 38.7, 38.1, 35.4, 35.4, 33.2, 32.1, 31.9, 28.4, 25.7, 25.0, 17.1; FTIR (film, NaCl $\nu_{max}$=3436, 2970, 2927, 1718, 1600, 1458, 1374, 1106 cm$^{-1}$; ESI (+) LRMS m/z (relative intensity): 709.24 (100%); ESI (+) HRMS (m/z): [M+Na$^+$] calcd for C$_{36}$H$_{50}$N$_2$O$_9$S 709.3135. found, 709.3131. Pure 19c was prepared in a similar fashion using pure 18c. $^1$H NMR (CDCl$_3$, 400 MHz) δ 7.84 (d, J=8.8 Hz, 1H), 7.26 (m, 2H), 7.20 (m, 3H), 6.52 (dd, J=2, 8.8 Hz, 1H), 6.48 (d, J=2.4 Hz, 1H), 5.85-5.62 (m, 3H), 5.05-4.85 (m, 6H), 4.05 (t, J=6.8 Hz, 2H), 3.95 (dd, J=6.4, 9.6 Hz, 1H), 3.89-3.77 (6H), 3.75-3.65 (m, 3H), 3.38 (dd, J=9.2, 15.6 Hz, 1H), 3.24 (dd, J=8, 14 Hz, 1H), 3.15 (dd, J=2.4, 15.2 Hz, 1H), 2.93 (m, 3H), 2.80 (dd, J=9.2, 14 Hz, 1H), 2.23 (m, 1H), 2.12 (m, 2H), 1.90-1.45 (m, 8H), 0.81 (d, J=6 Hz, 3H).

Example 61

Inhibitors 20b, 20c, 21b, and 21c: Under argon, dissolved carbamates 19b and 19c (118.5 mg, 0.17 mmol) into CH$_2$Cl$_2$ (125 mL) and added Grubb's 2$^{nd}$ gen. cat. (14.6 mg, 0.02 mmol). Stirred overnight. Solvents were removed under reduced pressure and the crude material purified by silica chromatography (50:50 EtOAc:Hexane) to give 110 mg (97% yield) of product as a dirty oil. TLC 70:30 EtOAc:Hexane R$_f$=0.45. Reversed-phase HPLC (Waters Sunfire C$_{18}$ 50×4.6 mm, 5 micron coupled to Agilent Eclipse XDB C$_{18}$ 150×4.6 mm, 5 micron and YMC-Pack C$_8$ 250×4.6 mm, 5 micron, Flow rate=0.95 mL/min, λ=215 nm, T=30° C., isocratic 60:40 MeCN:H$_2$O) was used to isolate the individual isomers: R$_t$ (R Z)=22 min, R$_t$ (S Z)=24 min, R$_t$ (R E)=25.3 min, R$_t$ (S E)=26.8 min.

Example 62

20b: [α]$_D^{20}$ −29 (c (0.60, CHCl$_3$); $^1$H NMR (CDCl$_3$, 800 MHz): δ 7.86 (d, J=8.8 Hz, 1H), 7.24 (m, 2H), 7.17 (m, 3H), 6.50 (dd, J=2.4, 8.8 Hz, 1H), 6.48 (d, J=1.6 Hz, 1H), 5.63 (d, J=4.8 Hz, 1H), 5.57 (q, J=7.2 Hz, 1H), 5.44 (q, J=9.6 Hz, 1H), 4.99 (q, J=6.4 Hz, 1H), 4.84 (d, J=9.6 Hz, 1H), 4.25 (m, 1H), 4.11 (m, 2H), 3.93 (dd, J=6.4, 9.6 Hz, 1H), 3.85 (s, 3H), 3.85-3.79 (m, 2H), 3.75-3.65 (m, 5H), 3.16 (dd, J=9.6, 15.2 Hz, 1H), 2.99 (dt, J=4, 13.6 Hz, 2H), 2.87 (m, 1H), 2.81 (d, J=15.2 Hz, 1H), 2.74 (dd, J=9.6, 14.4 Hz, 1H), 2.18 (m, 1H), 2.11-2.01 (m, 4H), 1.95 (m, 1H), 1.86 (m, 1H), 1.73 (m, 2H), 1.62-1.50 (m, 2H), 1.12 (d, J=6.4 Hz, 3H); $^{13}$C NMR (CDCl$_3$, 125 MHz): δ 137.5, 134.4, 131.1, 129.4, 128.4, 127.2, 126.5, 118.1, 109.3, 103.9, 100.3, 73.3, 73.0, 70.7, 69.6, 68.4, 59.1, 55.7, 54.7, 53.9, 45.3, 35.7, 32.8, 32.2, 29.7, 27.5, 26.1, 25.8, 25.4, 17.4; FTIR (film, NaCl) $\nu_{max}$=3467, 3333, 2923, 1717, 1595, 1575, 1533, 1495, 1444, 1384, 1324, 1256, 1206, 1139, 1073, 1021, 932, 755, 702, 668 cm$^{-1}$; ESI (+) HRMS (m/z): [M+Na$^+$] calcd for C$_{36}$H$_{50}$N$_2$O$_9$S 709.3135. found, 709.3131.

Example 63

20c: [α]$_D^{20}$ −30.6 (c 0.83, CHCl$_3$); $^1$H NMR (CDCl$_3$, 800 MHz): δ 7.83 (d, J=8.8 Hz, 1H), 7.25 (m, 2H), 7.17 (m, 3H), 6.50 (dd, J=1.6, 8.8 Hz, 1H), 6.78 (d, J=2.4 Hz, 1H), 5.66 (m, 1H), 5.64 (d, J=4.8 Hz, 1H), 5.52 (m, 1H), 5.00 (q, J=5.6 Hz, 1H), 4.84 (d, J=8.8 Hz, 1H), 4.02-3.88 (m, 4H), 3.86-3.78 (m, 6H), 3.74-3.65 (m, 3H), 3.11 (dd, J=8, 14.4 Hz, 1H), 2.96 (dd, J=3.2, 13.6 Hz, 1H), 2.89 (m, 2H), 2.74 (dd, J=8.8, 13.6 Hz, 1H), 2.18 (m, 1H), 2.09-1.94 (m, 5H), 1.90-1.78 (m, 4H), 1.69 (m, 1H), 1.61 (m, 1H), 1.13 (d, J=7.2 Hz, 3H); $^{13}$C NMR (CDCl$_3$, 125 MHz): δ 164.8, 158.1, 155.3, 137.6, 134.0, 133.3, 129.3, 128.5, 128.1, 126.5, 118.8, 109.3, 104.3, 100.7, 73.4, 72.6, 70.8, 69.6, 58.5, 58.1, 55.7, 54.8, 54.4, 45.3, 37.9, 35.4, 32.3, 30.0, 29.7, 28.6, 26.2, 25.8, 18.4, 17.7; FTIR (NaCl) $\nu_{max}$=3442, 3339, 2924, 2854, 1717, 1595, 1575, 1533, 1495, 1444, 1429, 1387, 1325, 1256, 1206, 1171, 1139, 1073, 1019, 988, 939, 835, 755, 701, 667 cm$^{-1}$; ESI (+) LRMS m/z (relative intensity): 1338.65 (7%), 681.34 (100%), 659.09 (19%), 304.05 (19%); ESI (+) HRMS (m/z): [M+Na]$^+$ calcd for C$_{34}$H$_{46}$N$_2$O$_9$S 681.2822. found, 681.2825.

Example 64

21b: [α]$_D^{20}$ 27.6 (c 0.36, CHCl$_3$); $^1$H NMR (CDCl$_3$, 800 MHz): δ 7.83 (d, J=8.8 Hz, 1H), 7.27 (m, 2H), 7.20 (m, 3H), 6.49 (m, 2H), 5.64 (d, J=5.6 Hz, 1H), 5.57 (q, J=7.2 Hz, 1H), 5.47 (q, J=8.8 Hz, 1H), 5.00 (q, J=8 Hz, 1H), 4.88 (d, J=8.8 Hz, 1H), 4.15 (m, 1H), 4.12 (m, 1H), 3.96 (m, 2H), 3.90-3.84 (m, 5H), 3.71-3.64 (m, 3H), 3.46 (m, 1H), 3.17 (m, 2H), 3.12 (dd, J=4, 14.4 Hz, 1H), 3.02 (dd, J=4.8, 14.4 Hz, 1H), 2.90 (m, 2H), 2.78 (dd, J=10.4, 14.4 Hz, 1H), 2.18 (m, 1H), 2.12-1.94 (m, 4H), 1.86 (m, 2H), 1.72 (m, 1H), 1.60-1.50 (m, 2H), 1.09 (d, J=6.4 Hz, 3H); $^{13}$C NMR (CDCl$_3$, 125 MHz): δ 164.8, 157.8, 155.6, 137.7, 134.3, 130.8, 129.3, 128.5, 127.6, 126.5, 118.3, 109.3, 104.0, 100.2, 73.4, 72.3, 709, 69.6, 68.4, 58.0, 55.7, 55.1, 53.3, 45.3, 35.4, 32.7, 32.2, 27.3, 26.0, 25.8, 25.3, 18.0; FTIR (film, NaCl) $\nu_{max}$=3467, 3337, 2927, 1717, 1595, 1575, 1538, 1495, 1456, 1325, 1255, 1206, 1141, 1073, 1021, 835, 754, 702, 668 cm$^{-1}$; ESI (+) HRMS (m/z): [M+Na$^+$] calcd for C$_{36}$H$_{50}$N$_2$O$_9$S 709.3135. found, 709.3131.

Example 65

21c: [α]$_D^{20}$ +20.5 (c 1.17, CHCl$_3$); $^1$H NMR (CDCl$_3$, 800 MHz): δ 7.83 (d, J=8.8 Hz, 1H), 7.24 (t, J=7.2 Hz, 2H), 7.18 (m, 1H), 7.14 (d, J=7.2 Hz, 2H), 6.50 (dd, J=2.4, 8.8 Hz, 1H), 6.47 (d, J=2.4 Hz, 1H), 5.67 (m, 1H), 5.64 (d, J=4.8 Hz, 1H), 5.53 (m, 1H), 5.00 (q, J=8 Hz, 1H), 4.76 (d, J=9.6 Hz, 1H), 4.17 (br, 1H), 4.11 (m, 1H), 3.94 (dd, J=6.4, 9.6 Hz, 1H), 3.88 (t, J=8.8 Hz, 1H), 3.85 (m, 4H), 3.80 (m, 1H), 3.75 (m, 1H), 3.69 (m, 2H), 3.55 (m, 1H), 2.98 (m, 2H), 2.91 (m, 2H), 2.76 (dd, J=8.8, 14.4 Hz, 1H), 2.47 (br, 1H), 2.26 (m, 1H), 2.17 (m, 2H), 1.93 (m, 1H), 1.87 (m, 1H), 1.82-1.70 (m, 4H), 1.63 (m, 1H), 1.47 (m, 1H), 1.06 (d, J=6.4 Hz, 3H); $^{13}$C NMR (CDCl$_3$, 125 MHz): δ 164.8, 158.1, 155.2, 137.4, 134.2, 132.5, 129.6, 129.4, 128.5, 126.5, 119.0, 109.3, 104.2, 100.5, 73.4, 71.5, 70.8, 69.6, 58.6, 55.7, 54.9, 54.6, 45.3, 38.2, 35.7, 33.6, 30.3, 29.8, 28.1, 26.2, 25.8, 19.0; FTIR (film, NaCl) $\nu_{max}$=3463, 3339, 2925, 1717, 1595, 1575, 1538, 1495, 1444, 1387, 1326, 1256, 1207, 1171, 1140, 1073, 1019, 987, 920, 836, 734, 701 cm$^{-1}$; ESI (+) LRMS m/z (relative intensity): 1338.70 (36%), 681.25 (100%); ESI (+) HRMS (m/z): [M+Na]$^+$ calcd for C$_{34}$H$_{46}$N$_2$O$_9$S 681.2822. found, 681.2812.

EXAMPLE Cells and viruses. Human CD4$^+$ MT-2 and MT-4 cell lines were grown in RPMI 1640-based culture medium supplemented with 10% fetal calf serum (PAA Laboratories GmbH, Linz, Austria) plus 50 U of penicillin and 100 μg of kanamycin per ml. The following HIV-1 strains were used for the drug susceptibility assay: HIV-1$_{LAI}$, HIV-1$_{NL4-3}$, HIV-2$_{EHO}$, and HIV-2$_{ROD}$, as well as clinical HIV-1 strains from drug-naive patients with AIDS (HIV-1$_{ERS104pre}$) (Clavel et al. 1986 Science 233:343-6; Shirasaka et al. 1993 Proc Natl Acad Sci USA 90:562-6; Yoshimura et al. 2002 J Virol 76:1349-58.), and six HIV-1 clinical isolates that were originally isolated from patients with AIDS who had received anti-HIV-1 therapy heavily (for 32 to 83 months) and that were genotypically and phenotypically characterized as multiple-PI resistant HIV-1 variants (Yoshimura et al. 1999 Proc Natl Acad Sci USA 96:8675-80). To determine whether each clinical HIV-1 isolate used in the present study was a syncytium-inducing (SI virus) or non-syncytium-inducing (NSI virus) strain, MT-2 cells ($10^5$) were exposed to an aliquot of viral stock supernatant containing 100 50% tissue culture infectious doses (TCID$_{50S}$) of the virus and cultured in 6-well culture plates. Cultures were maintained for 4 weeks and were examined under an inverted microscope to determine the syncytium-inducing or non-syncytium-inducing nature of the virus, as described previously (Id.).

EXAMPLE Antiviral agents. Saquinavir (SQV) and ritonavir (RTV) were obtained from Roche Products, Ltd. (Welwyn Garden City, United Kingdom) and Abbott Laboratories (Abbott Park, Ill.), respectively. Amprenavir (APV) was obtained from GlaxoSmithKline (Research Triangle Park, N.C.). Nelfinavir (NFV) and lopinavir (LPV) were obtained from Japan Energy, Inc., Tokyo, Japan. Indinavir (IDV) was obtained from Merck Research Laboratories (Rahway, N.J.). Atazanavir (AZV) was obtained from Bristol Myers Squibb (New York, N.Y.). Darunavir (DRV) was synthesized as previously described (Ghosh et al. 2004. J Org Chem 69:7822-9.). Tipranavir (TPV) was obtained through the AIDS Research and Reference Reagent Program, Division of AIDS, NIAID, National Institutes of Health.

EXAMPLE Drug susceptibility assay. The susceptibility of HIV-1$_{LAI}$ and primary HIV-1 isolates to various drugs were determined as described previously (Koh et al. 2003 Antimicrob Agents Chemother 47:3123-9). Briefly, MT-2 cells ($2\times10^4$/ml) were exposed to 100 50% tissue culture infectious doses (TCID$_{50S}$) of HIV-1$_{LAI}$, in the presence or absence of various concentrations of drugs in 96-well microculture plates and were incubated at 37° C. for 7 days. After 100 μl of the medium was removed from each well, 3-(4,5-dimethylthiazol-2-yl)-2,5-diphenyltetrazolium bromide (MTT) solution (10 μl, 7.5 mg/ml in phosphate-buffered saline) was added to each well in the plate, followed by incubation at 37° C. for 3 h. After incubation to dissolve the formazan crystals, 100 μl of acidified isopropanol containing 4% (vol/vol) Triton X-100 was added to each well and the optical density was measured using a kinetic microplate reader (Vmax; Molecular Devices, Sunnyvale, Calif.). All assays were performed in duplicate or triplicate. To determine the susceptibility of primary HIV-1 isolates to drugs, phytohemagglutinin-activated peripheral blood mononuclear cells (PHA-PBMCs; $10_6$/ml) were exposed to 50 TCID$_{50S}$ of each. The target cells were exposed to HIV-1$_{104pre}$ or drug-resistant HIV-1 in the presence or absence of various concentrations of drugs and were incubated for 7 days. Upon the conclusion of the culture, the amounts of p24 Gag protein in the supernatants were determined using a fully automated chemiluminescent enzyme immunoassay system (Lumipulse F; Fujirebio Inc., Tokyo, Japan) (Maeda et al. 2001 J Biol Chem 276:35194-200). To determine the drug susceptibility of certain laboratory HIV-1 strains, MT-4 cells were used as target cells. In brief, MT-4 cells ($10^5$/ml) were exposed to 100 TCID$_{50S}$ of drug-resistant HIV-1 strains in the presence or absence of various concentrations of drugs and on day 7 of culture, the supernatant was harvested and the amounts of p24 Gag protein were determined. The drug concentrations that suppressed the production of p24 Gag protein by 50% (50% effective concentrations [EC$_{50S}$]) were determined by comparison with the level of p24 production in drug-free control cell cultures. All assays were performed in duplicate or triplicate.

EXAMPLE Generation of PI-resistant HIV-1 in vitro. In the experiments for selecting drug-resistant variants, MT-4 cells were exploited as target cells, since HIV-1 in general replicates at greater levels in MT-4 cells than in MT-2 cells. MT-4 cells ($10^5$/ml) were exposed to HIV-1NL4-3 (500 TCID50s) and cultured in the presence of various PIs, each at an initial concentration of its EC50 value. Viral replication was monitored by determining the amount of p24 Gag produced by MT-4 cells. The culture supernatants were harvested on day 7 and used to infect fresh MT-4 cells for the next round of culture in the presence of increasing concentrations of each drug. When the virus began to propagate in the presence of the drug, the drug concentration was generally increased two- to three-fold. Proviral DNA samples obtained from the lysates of infected cells were subjected to nucleotide sequencing of the HIV genome.

EXAMPLE Determination of nucleotide sequences. Molecular cloning and determination of the nucleotide sequences of HIV-1 strains passaged in the presence of anti-HIV-1 agents were performed as described previously. Briefly, high-molecular-weight DNA was extracted from HIV-1-infected MT-4 cells by using the InstaGene Matrix (Bio-Rad Laboratories, Hercules, Calif.) and was subjected to molecular cloning, followed by sequence determination. The first-round PCR mixture consisted of 1 μl of proviral DNA solution, 10 μl of Premix Taq (Ex Taq version; Takara Bio, Inc., Otsu, Japan), and 10 pmol of each of the first PCR primers in a total volume of 20 ml. The PCR conditions used were an initial 5 cycles of 30 sec at 95° C., 2 min at 55° C., and 2 min at 72° C., and followed by 15 cycles of 30 sec at 95° C., 20 sec at 55° C., and 2 min at 72° C. The first-round PCR products were used directly in the second round of PCR. The second-round PCR products were purified with spin columns (MicroSpin S-400 HR columns; Amersham Biosciences Corp., Piscataway, N.J.), cloned directly, and subjected to sequencing with a cloned directly, and subjected to sequencing with a model 3130 automated DNA sequencer (Applied Biosystems, Foster City, Calif.).

EXAMPLE Generation of FRET-based HIV-1 expression system. The intermolecular fluorescence resonance energy transfer-based HIV-1-expression assay employing cyan and yellow fluorescent protein-tagged protease monomers (CFP and YFP, respectively) was generated as described previously (Koh et al. 2007 J Biol Chem 282:28709-20). Briefly, CFP- and YFP-tagged HIV-1 protease constructs were generated using BD Creator™ DNA Cloning Kits (BD Biosciences, San Jose, Calif.). For the generation of full 206 length molecular infectious clones containing CFP- or YFP-tagged protease, the PCR207 mediated recombination method was used (Fang et al. 1999 Nat Med 5:239-42). A linker consisting of five alanines was inserted between protease and fluorescent proteins. The phenylalanine-proline site that HIV-1 protease cleaves was also introduced between the fluorescent protein and RT. Thus obtained DNA fragments were subsequently joined by using the PCR-mediated recombination reaction performed under the standard condition for ExTaq polymerase (Takara Bio Inc., Otsu, Japan). The amplified PCR products were cloned into pCR-XL213 TOPO vector according to the manufacturer's instructions (Gateway Cloning System; Invitrogen, Carlsbad, Calif.). PCR products were generated with pCR-XL-TOPO vector as templates, followed by digestion by both ApaI and SmaI, and the ApaI-SmaI fragment was introduced into pHIV-$1_{NLSma}$ (Gatanaga et al. 2002 J Biol Chem 277:5952-61), generating pHIV-PR$_{WT\ CFP}$ and pHIV-PR$_{WT\ YFP}$, respectively.

EXAMPLE FRET procedure. COS7 cells plated on EZ view cover-glass bottom culture plate (Iwaki, Tokyo) were transfected with pHIV-PR$_{WT\ CFP}$ and pHIV-PR$_{WT\ YFP}$ using Lipofectamine 2000 (Invitrogen, Carlsbad, Calif.) according to manufacturer's instructions in the presence of various concentrations of each compound, cultured for 72 hrs, and analyzed under Fluoview FV500 confocal laser scanning microscope (OLYMPUS Optical Corp, Tokyo) at room temperature as previously described. When the effect of each compound was analyzed by FRET, test compounds were added to the culture medium simultaneously with plasmid transfection. Results of FRET were determined by quenching of CFP (donor) fluorescence and an increase in YFP (acceptor) fluorescence (sensitized emission), since part of the energy of CFP is transferred to YFP instead of being emitted. The changes in the CFP and YFP fluorescence intensity in the images of selected regions were examined and quantified using Olympus FV500 Image software system (OLYMPUS Optical Corp). Ratios of intensities of CFP fluorescence after photobleaching to CFP fluorescence prior to photobleaching (CFP$_{A/B}$ ratios) were determined. When the CFP$_{A/B}$ ratios were less than 1, it indicated that the association of the two subunits did not occur and it was interpreted that protease dimerization was inhibited.

MT-2 cells ($2\times10^3$) were exposed to 100 TCID$_{50}$s of HIV-$1_{LAI}$, HIV-$2_{EHO}$, or HIV-$2_{ROD}$, and cultured in the presence of various concentrations of each PI, and EC$_{50}$s were determined by using the MTT assay. All assays were conducted in duplicate, and data shown represent mean values (±1 standard deviation) derived from results of three independent experiments. Each selectivity index denotes a ratio of CC$_{50}$ to EC$_{50}$ against HIV-$1_{LAI}$. N.D., not done.

EXAMPLE GRL-216 and GRL-286 are potent against PI-selected laboratory HIV-1 variants. HIV-1 variants that had been selected in vitro with each of five FDA-approved PIs (SQV, NFV, APV, LPV and AZV) were obtained by propagating a wild type laboratory HIV-1 strain, HIV-$1_{NL4-3}$, in the presence of increasing concentrations of each PI in MT-4 cells over 37-60 passages in vitro. The thus obtained variants showed acquired various PI resistance-associated amino acid substitutions in the protease-encoding region of the viral genome. Each of the variants (HIV-$1_{SQV5\ \mu M}$, HIV-$1_{NFV5\ \mu M}$, HIV-$1_{APV5\ \mu M}$, HIV-$1_{LPV5\ \mu M}$, and HIV-$1_{AZV5\ \mu M}$) (Koh et al. 2009 Antimicrob Agents Chemother 53:997-1006), was highly resistant to the corresponding PI, with which the variant was selected, with an EC$_{50}$ value of >1 µM; and the fold differences of the EC$_{50}$ values, compared to the EC$_{50}$ value of each drug against HIV-$1_{NL4-3}$, ranged from >22 to >250. The activities of GRL-216 against all these variants except HIV-$1_{APV5\ \mu M}$ were well maintained with fold-differences of 4 to 8. GRL-216 was virtually inert against HIV $1_{APV5\ \mu M}$, with an EC$_{50}$ value of >1 µM. GRL-286 was potent to HIV-$1_{SQV5\ \mu M}$, HIV-$1_{NFV5\ \mu M}$, and HIV-$1_{AZV5\ \mu M}$, but the compound was less

TABLE 6

| Drug | EC$_{50}$ (µM) for HIV-$1_{LAI}$ | HIV-$2_{EHO}$ | HIV-$2_{ROD}$ | CC$_{50}$ (µM) | Selectivity Index |
|---|---|---|---|---|---|
| APV | 0.024 ± 0.008 | 0.12 ± 0.03 | 0.42 ± 0.10 | >100 | >4,170 |
| LPV | 0.039 ± 0.006 | 0.035 ± 0.025 | 0.028 ± 0.004 | >100 | >2,560 |
| TPV | 0.17 ± 0.005 | 0.30 ± 0.15 | 0.33 ± 0.07 | 54.1 ± 2.1 | 320 |
| DRV | 0.003 ± 0.0004 | 0.008 ± 0.007 | 0.010 ± 0.004 | >100 | >33,300 |
| GRL-216 | 0.002 ± 0.001 | 0.010 ± 0.007 | 0.017 ± 0.001 | 48.8 ± 1.3 | 24,400 |
| GRL-246 | 0.022 ± 0.005 | N.D. | N.D. | 33.3 ± 0.8 | 1,510 |
| GRL-286 | 0.004 ± 0.001 | 0.018 ± 0.013 | 0.025 ± 0.002 | 33.1 ± 2.5 | 8,280 |
| GRL-396 | 0.014 ± 0.001 | N.D. | N.D. | 44.9 ± 4.1 | 3,200 | potent against HIV-$1_{LPV5\ \mu M}$ and virtually inert against HIV-$1_{APV5\ \mu M}$.

TABLE 7

| Virus | EC$_{50}$ (µM) | | | | | | | | |
|---|---|---|---|---|---|---|---|---|---|
| | SQV | NFV | APV | LPV | AZV | TPV | DRV | GRL-216 | GRL-286 |
| HIV-$1_{NL4-3}$ | 0.005 ± 0.002 | 0.045 ± 0.032 | 0.034 ± 0.001 | 0.046 ± 0.025 | 0.004 ± 0.0004 | 0.32 ± 0.07 | 0.003 ± 0.0006 | 0.005 ± 0.001 | 0.009 ± 0.0006 |
| HIV-$1_{SQV5\mu M}$ | >1 (>200) | 0.51 ± 0.081 (11) | 0.18 ± 0.10 (5) | 0.12 ± 0.02 (2) | 0.21 ± 0.065 (53) | 0.022 ± 0.009 (0.1) | 0.003 ± 0.0002 (1) | 0.020 ± 0.009 (4) | 0.046 ± 0.021 (5) |

TABLE 7-continued

| | $EC_{50}$ (μM) | | | | | | | | |
|---|---|---|---|---|---|---|---|---|---|
| Virus | SQV | NFV | APV | LPV | AZV | TPV | DRV | GRL-216 | GRL-286 |
| HIV-1$_{NFV5\mu M}$ | 0.003 ± 0.002 (1) | >1 (>22) | 0.028 ± 0.005 (1) | 0.037 ± 0.004 (1) | 0.027 ± 0.005 (7) | 0.039 ± 0.041 (0.1) | 0.006 ± 0.0002 (2) | 0.040 ± 0.017 (8) | 0.041 ± 0.006 (5) |
| HIV-1$_{APV5\mu M}$ | 0.026 ± 0.010 (5) | 0.30 ± 0.03 (7) | >1 (>29) | >1 (>22) | 0.006 ± 0.002 (2) | 0.22 ± 0.089 (0.7) | 0.29 ± 0.0018 (97) | >1 (>200) | >1 (>111) |
| HIV-1$_{LPV5\mu M}$ | 0.028 ± 0.007 (6) | 0.32 ± 0.12 (7) | 0.26 ± 0.07 (8) | >1 (>22) | 0.036 ± 0.001 (9) | 0.31 ± 0.030 (1) | 0.025 ± 0.0066 (8) | 0.035 ± 0.005 (7) | 0.35 ± 0.019 (39) |
| HIV-1$_{AZV5\mu M}$ | 0.031 ± 0.005 (6) | >1 (>22) | 0.28 ± 0.06 (8) | >1 (>22) | >1 (>250) | 0.41 ± 0.047 (1) | 0.009 ± 0.0025 (3) | 0.023 ± 0.005 (5) | 0.030 ± 0.006 (3) |

Amino acid substitutions identified in the protease-encoding region of HIV-1$_{SQV-5!M}$, HIV-1$_{NFV-!M}$, HIV-1$_{APV-5!M}$, HIV-1$_{LPV-5!M}$ and HIV-1$_{AZV-5!M}$ compared to the consensus B sequence cited from the Los Alamos data base include L10I/G48V/I54V/A71V/I84V/L90M, L10F/D30N/K45I/A71V/T74S, L10F/M46I/I50V/A71V/I84V/L90M, L10F/M46I/I54V/V82A, and L23I/E34Q/K43I/M46I/I50L/G51A/L63P/A71V/V82A/T91A, respectively. MT-4 cells ($10^4$) were exposed to 100 TCID$_{50}$s of each HIV-1, and inhibition of p24 Gag protein production by each drug was used as an end point. Numbers in parentheses represent n-fold changes in EC$_{50}$s for each isolate compared to the EC$_{50}$s for wild-type HIV-1$_{NL4-3}$. All assays were conducted in duplicate or triplicate, and data shown represent mean values (±1 standard deviation) derived from results of three independent experiments.

EXAMPLE GRL-216 and -286 exert potent activity against highly multi-PI-resistant clinical HIV-1 strains. Previously isolated highly multiple-PI-resistant clinical HIV-1 strains (HIV-1$_{MDR}$) including HIV-1$_{MDR/B}$, HIV-1$_{MDR/C}$, using p24 production inhibition as an end point (Table 8). Both TPV and DRV had well maintained their activity and the fold-differences between their EC$_{50}$ values against HIV-1$_{ERS104pre}$ (wild-type) and those against multidrug-resistant clinical isolates ranged 1 to 9, while it was noteworthy that the greatest EC$_{50}$ values of DRV was much lower (0.027 μM) than that of TPV (0.38 μM). GRL-216 and -286 exerted potent antiviral activity against HIV-1$_{ERS104pre}$ with EC$_{50}$ values of as low as 0.005 and 0.007 μM, respectively (Table 8). The potency of GRL-216 and -286 against 5 PI-resistant variants (HIV-1$_{MDR/B}$, HIV-1$_{MDR/C}$, HIV-1$_{MDR/G}$, HIV-1$_{MDR/TM}$, and HIV-1$_{MDR/MM}$) was well maintained with the fold-differences of EC$_{50}$ values by 4 to 13, as compared to their EC$_{50}$ values against HIV-1$_{ERS104pre}$. However, both GRL-216 and -286 were less potent against HIV-1$_{MDR/JSL}$ with the fold-differences of EC$_{50}$ values by 15- and 30-fold, respectively. It was noted that HIV-1$_{MDR/JSL}$ was most resistant to all other PIs examined except TPV and DRV (Table 8).

TABLE 8

| | $EC_{50}$ (μM) | | | | | | | | |
|---|---|---|---|---|---|---|---|---|---|
| Virus | SQV | IDV | APV | LPV | AZV | TPV | DRV | GRL-216 | GRL-286 |
| HIV-1$_{ERS104pre}$ (wild-type SI) | 0.008 ± 0.005 | 0.043 ± 0.004 | 0.030 ± 0.005 | 0.034 ± 0.002 | 0.002 ± 0.001 | 0.12 ± 0.03 | 0.003 ± 0.0002 | 0.005 ± 0.003 | 0.007 ± 0.002 |
| HIV-1$_{MDR/B}$ (SI) | 0.27 ± 0.073 (34) | >1 (>23) | >1 (>33) | >1 (>29) | 0.20 ± 0.10 (100) | 0.18 ± 0.009 (2) | 0.019 ± 0.012 (6) | 0.037 ± 0.016 (7) | 0.089 ± 0.016 (13) |
| HIV-1$_{MDR/C}$ (SI) | 0.032 ± 0.002 (11) | >1 (>23) | 0.37 ± 0.011 (12) | >1 (>29) | 0.065 ± 0.008 (33) | 0.38 ± 0.079 (3) | 0.008 ± 0.006 (3) | 0.044 ± 0.002 (9) | 0.029 ± 0.001 (4) |
| HIV-1$_{MDR/G}$ (SI) | 0.030 ± 0.002 (4) | 0.34 ± 0.14 (5) | 0.43 ± 0.004 (14) | 0.26 ± 0.04 (8) | 0.033 ± 0.024 (17) | 0.24 ± 0.08 (2) | 0.023 ± 0.006 (5) | 0.057 ± 0.012 (11) | 0.028 ± 0.004 (4) |
| HIV-1$_{MDR/TM}$ (SI) | 0.26 ± 0.04 (33) | >1 (>23) | 0.32 ± 0.007 (11) | >1 (>29) | 0.065 ± 0.008 (33) | 0.38 ± 0.05 (3) | 0.004 ± 0.001 (1) | 0.027 ± 0.001 (6) | 0.072 ± 0.014 (10) |
| HIV-1$_{MDR/MM}$ (NSI) | 0.19 ± 0.05 (24) | >1 (>23) | 0.21 ± 0.222 (7) | >1 (>29) | 0.18 ± 0.021 (39) | 0.36 ± 0.06 (3) | 0.011 ± 0.002 (4) | 0.033 ± 0.010 (7) | 0.055 ± 0.025 (8) |
| HIV-1$_{MDR/JSL}$ (NSI) | 0.30 ± 0.02 (37) | >1 (>23) | 0.62 ± 0.02 (21) | >1 (>29) | 0.43 ± 0.036 (215) | 0.23 ± 0.049 (2) | 0.027 ± 0.011 (9) | 0.073 ± 0.07 (15) | 0.21 ± 0.032 (30) |

HIV-1$_{MDR/G}$, HIV-1$_{MDR/TM}$, HIV-1$_{MDR/MM}$, and HIV-1$_{MDR/JSL}$, from patients with AIDS who had failed then-existing anti-HIV regimens after receiving 9 to 11 anti-HIV-1 drugs over 32 to 83 months were evaluated. These clinical strains contained 9 to 14 amino acid substitutions in the protease-encoding region, which have reportedly been associated with HIV-1 resistance to various PIs. The EC$_{50}$ values of IDV and LPV with these multidrug-resistant clinical HIV-1 isolates were mostly >1 μM, and the activity of other four PIs (SQV, APV, and AZV) was also found to be significantly compromised, as examined in PHA-PBMCs as target cells Amino acid substitutions identified in the protease-encoding region compared to the consensus type B sequence cited from the Los Alamos database include L63P in HIV-1$_{ERS104pre}$; L10I, K14R, L33I, M36I, M46I, F53I, K55R, I62V, L63P, A71V, G73S, V82A, L90M, and I193L in HIV-1$_{MDR/B}$; L10I, I15V, K20R, L24I, M36I, M46L, I54V, I62V, L63P, K70Q, V82A, and L89M in HIV-1$_{MDR/C}$; L10I, V11I, T12E, I15V, L19I, R41K, M46L, L63P, A71T, V82A, and L90M in HIV-1$_{MDR/G}$; L10I, K14R, R41K, M46L, I54V, L63P, A71V, L90M, I93L in HIV-1$_{MDR/TM}$; L10I, K43T, M46L, I54V, L63P, A71V, V82A, L90M, and Q92K in HIV-1$_{MDR/MM}$; L10I, L24I, I33F, E35D, M36I, N37S, M46L, I54V, R57K, I62V, L63P, A71V, G73S, and V82A in HIV-1$_{MDR/JSL}$. HIV-1$_{ERS104pre}$ served as a source of wild-type HIV-1. EC$_{50}$s were determined by using PHA-PBMs as target cells, and inhibition of p24 Gag protein production by each drug was used as an end point. Numbers in parentheses represent n-fold changes of EC$_{50}$s for each isolate compared to EC$_{50}$s for wild-type HIV-1$_{ERS104pre}$. All assays were conducted in duplicate or triplicate, and data shown represent mean values (±1 standard deviation) derived from results of three independent experiments.

EXAMPLE GRL-216 and GRL-286 block the dimerization of HIV-1 protease. In the FRET-based HIV-1 expression system, COS7 cells were transfected with pHIV-PR$_{WT}$ CFP and pHIV-PR$_{WT\,YFP}$ and exposed to various concentrations of either of the drugs and the CFP$_{A/B}$ ratios were determined at the end of 72-hr culture. In the absence of drug, the CFP$_{A/B}$ ratios were virtually all above 1.0 with average figures of 1.29 and 1.13 for GRL-216 and GRL-286, respectively (FIG. 1), indicating that protease dimerization occurred in the system. However, when the transfected COS7 cells were exposed to greater than 0.1 μM of GRL-216, the average CFP$_{A/B}$ ratios were all less than 1.0, indicating that GRL-216 effectively blocked HIV-1 protease dimerization (FIG. 1). GRL-286 also effectively blocked the dimerization at the same concentration range.

Figure 2:
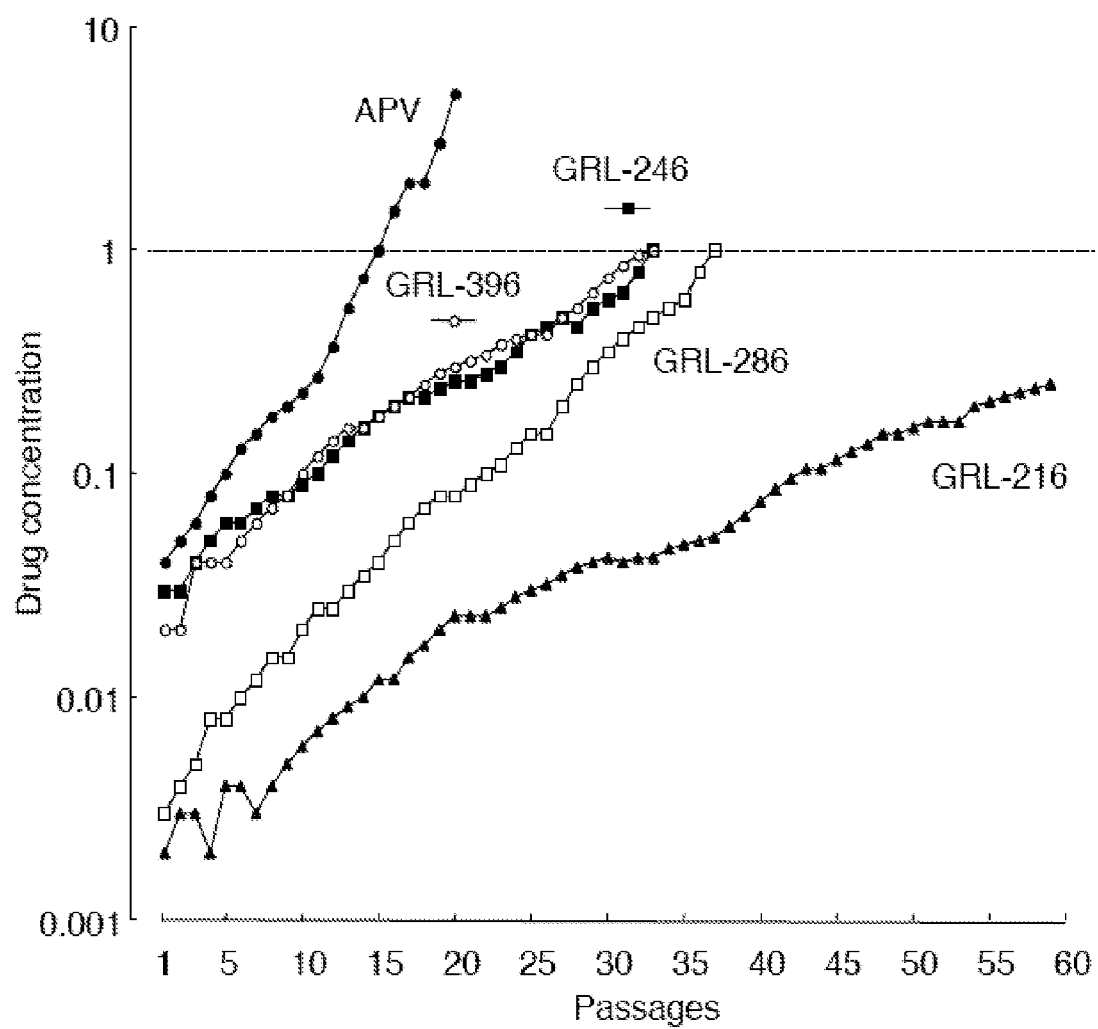
FIG. 2. In vitro selection of HIV-1 variants resistant to GRL-216, -246 (15c), -286 and -396. HIV-1$_{NL4-3}$ was propagated in MT-4 cells in the presence of increasing concentrations of APV (●), GRL-216 (▲), -246 (■), -286 (□) or -396 (14d) (○). Each passage of HIV-1 was conducted in a cell-free fashion. APV was employed as a reference compound.

EXAMPLE In vitro selection of HIV-1 variants resistant to four mcPIs. HIV-1 variants resistant to GRL-216, GRL-246, GRL-286, GRL-396 and APV, were selected out by propagating HIV-1$_{NL4-3}$ in MT-4 cells in the presence of increasing concentrations of each PI as previously described (Amano et al. 2007 Antimicrob Agents Chemother 51:2143-55). As shown in FIG. 2, HIV-1 variants that replicated in the presence of 1 μM of APV, GRL-396, GRL-246 and GRL-286 emerged by passages 20, 33, 33, and 37, respectively; however, the virus exposed to GRL-216 continued to be fairly susceptible to GRL-216 even after 50 passages. Beyond approximately 50 passages with GRL-216 exposure, the virus replicated highly poorly, and virtually failed to replicate at >0.26 μM, demonstrating that the emergence of GRL-216-resistant HIV-1 variant is substantially delayed compared to APV and other mcPIs examined here. Determination of nucleotide sequence of the protease-encoding region disclosed that the variants resistant to APV (5 μM: passage 20) had acquired previously reported mutations such as L10I, V32I, M46I, and I84V. By passage 5 with GRL-216 exposure, the wild-type protease gene sequence in the virus was seen. However, by passage 10 and beyond, the virus was seen to contain V82I substitution. As the passage proceeded, more amino acid substitutions were acquired. By passage 30, the virus had acquired L10I and I84V substitutions. By passage 50 (0.16 μM GRL-216: HIV$_{246-P50}$), the virus had further acquired L24I and M46I substitutions. By passage 60, the virus had gained L63P substitutions as well. HIV-1 exposed to GRL-246 had acquired L10F, M46I, and T91S in the protease362 encoding region by passage 33 (1 μM GRL-246). HIV-1 exposed to GRL-286, by passage 37 (1 μM), had acquired L10F, M46L, I50V, and A71V in the protease-encoding region. The HIV-1 selected against GRL-396 had acquired, by passage 33 (1 μM GRL-396), L10F, M46I, Q61K, V82I and I84V in the protease-encoding region. We also examined whether the virus acquired mutations in the Gag region at several passages of GRL-216 selection. It was found that by passage 10, the virus had acquired the E107D substitution. By passage 25 and beyond, V35I, R275K and the p1/p6 cleavage site substitution, L449F, had emerged. By passage 50, V390D emerged and persisted (data not shown). We also determined the amino acid sequences of the gag region of each of the selected HIV variants with direct base-sequencing. Two amino acid substitutions were seen in common: V35I substitution was identified in GRL-216-, -246-, and -286-selected variants (by 25, 10, and 20 passages, respectively) and L449F substitution (Doyon et al. 1996 J Virol 70:3763-9) in GRL-216- and -286-selected variants (by 25 and 20 passages, respectively). Other than these two amino acid substitutions, only sporadic substitutions were identified in the gag region of the four variants (data not shown).

EXAMPLE Susceptibility of selected HIV-1 variants to various PIs. As shown in Table 9, HIV$_{246-P}$ was resistant to GRL-216, with a 24-fold-greater EC$_{50}$ (0.094 μM) relative to the EC$_{50}$ of GRL-216 against HIV-1$_{NL4-3}$. HIV$_{216-P50}$ was more resistant to other three mcPIs examined with the EC$_{50}$ fold difference values against HIV$_{246-1\,\mu M}$, HIV$_{286-1\,\mu M}$, and HIV$_{396-1\,\mu M}$ of 75, >250, and 18, respectively. However, HIV$_{216-P50}$ was still susceptible to DRV with 3-fold difference relative to that against HIV-1$_{NL4-3}$. Interestingly, all the four mcPI-selected HIV-1 variants including HIV$_{246-P50}$ were paradoxically more susceptible to TPV by factors of 3.3 to 10 relative to the susceptibility of HIV-1$_{NL4-3}$ against TPV (Table 9), suggesting that the combination of GRL-216 (and other three mcPIs as well) and TPV could exert complementarily augmented antiviral activity against mcPI-resistant HIV-1 variants.

TABLE 9

| Virus | EC$_{50}$ (μM) | | | | | | | | | |
|---|---|---|---|---|---|---|---|---|---|---|
| | APV | NFV | LPV | AZV | TPV | DRV | GRL-216 | GRL-246 | GRL-286 | GRL-396 |
| HIV-1$_{NL4-3}$ | 0.032 ± 0.001 | 0.040 ± 0.007 | 0.035 ± 0.004 | 0.0032 ± 0.0001 | 0.29 ± 0.05 | 0.003 ± 0.001 | 0.004 ± 0.001 | 0.033 ± 0.003 | 0.006 ± 0.005 | 0.017 ± 0.005 |
| HIV-1$_{216-p50}$ | 0.26 ± 0.03 (8) | 0.13 ± 0.04 (4) | 0.19 ± 0.06 (5) | 0.014 ± 0.003 (4) | 0.029 ± 0.0004 (0.1) | 0.009 ± 0.006 (3) | 0.094 ± 0.075 (24) | 0.26 ± 0.05 (8) | 0.19 ± 0.06 (32) | 0.24 ± 0.06 (14) |
| HIV-1$_{246-1\mu M}$ | 0.34 ± 0.015 (11) | 0.29 ± 0.006 (7) | 0.33 ± 0.04 (8) | 0.032 ± 0.003 (10) | 0.095 ± 0.089 (0.3) | 0.029 ± 0.001 (10) | 0.30 ± 0.01 (75) | 0.42 ± 0.09 (12) | 0.33 ± 0.03 (55) | 0.37 ± 0.013 (22) |
| HIV-1$_{286-1\mu M}$ | >1 (>31) | 0.37 ± 0.03 (9) | >1 (>23) | 0.021 ± 0.012 (7) | 0.037 ± 0.001 (0.1) | 0.20 ± 0.05 (67) | >1 (>250) | >1 (>30) | >1 (>167) | >1 (>59) |
| HIV-1$_{396-1\mu M}$ | 0.35 ± 0.0002 (11) | 0.22 ± 0.02 (6) | 0.28 ± 0.05 (6) | 0.024 ± 0.002 (8) | 0.042 ± 0.002 (0.1) | 0.016 ± 0.001 (5) | 0.073 ± 0.011 (18) | 0.37 ± 0.022 (11) | 0.25 ± 0.05 (42) | 0.52 ± 0.07 (31) |

Amino acid substitutions identified in the protease-encoding region of HIV-1$_{216\text{-}p50}$, HIV-1$_{246\text{-}1!M}$, HIV-1$_{286\text{-}1!M}$, and HIV-1$_{396\text{-}1!M}$, compared to the consensus B sequence cited from the Los Alamos database include L10I/L24I/M46I/V82I/I84V, L10F/M46I/T91S, L10F/M46L/I50V/A71V, and L10F/M46M or I/Q61Q or K/V82I/I84V, respectively. MT-4 cells ($10^4$) were exposed to 100 TCID$_{50}$s of each HIV-1, and inhibition of p24 Gag protein production by each drug was used as an end point. Numbers in parentheses represent n-fold changes in EC$_{50}$s for each isolate compared to the EC$_{50}$s for wild-type HIV-1$_{NL4\text{-}3}$. All assays were conducted in duplicate or triplicate, and data shown represent mean values (±1 standard deviation) derived from results of three independent experiments.

Figure 3:
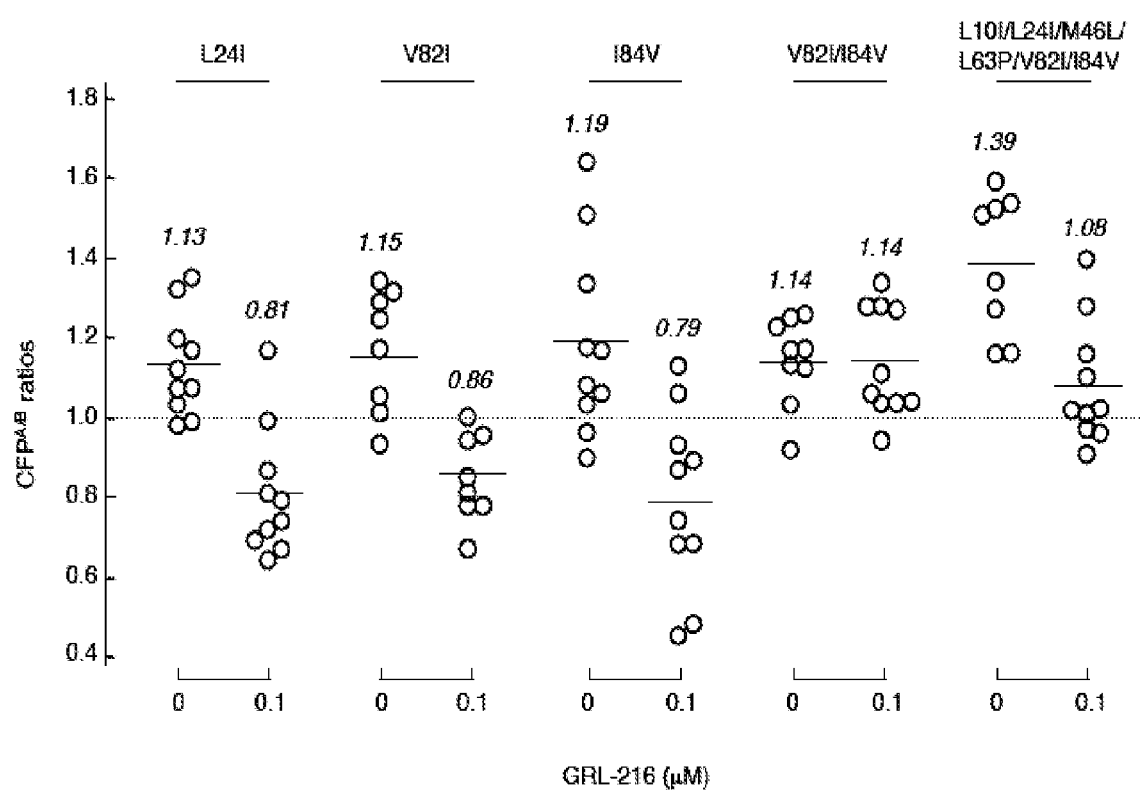
FIG. 3. GRL-216 (14c) fails to block protease dimerization with V82I/I84V substitutions. To examine whether an amino acid substitution(s) that emerged upon GRL-216 selection of HIV-1$_{NL4-3}$, recombinant clones containing one of the following mutations: L24I, V82I, I84V, V82I/I84V, and L10I/L24I/M46L/L63P/V82I/I84V were generated in the setting of the FRET-based HIV-1 expression assay (Koh, 2007). With L24I, V82I, or I84V alone, the activity of 0.1 μM GRL-216 to block protease dimerization was not affected; however, with either set of V82I/I84V or L10I/L24I/M46L/L63P/V82I/I84V substitutions, GRL-216 failed to block the dimerization.

EXAMPLE V82I/I84V substitutions prevent GRL-216 from blocking protease dimerization and play a role in HIV-1 resistance to GRL-216. It has been discovered herein that the GRL-216- and -396-selected HIV-1 variants had acquired various amino acid substitutions prompted us to examine whether such amino acid substitutions affected the protease dimerization inhibition of GRL-216. A pair (one with CFP and the other with YFP) of recombinant clones containing one of the following mutations: L24I, V82I, I84V, V82I/I84V, and L10I/L24I/M46L/L63P/V82I/I84V in the setting of the FRET-based HIV-1 expression assay were prepared. With L24I, V82I, or I84V alone, the activity of 0.1 µM GRL-216 to block protease dimerization was not affected; however, with either set of V82I/I84V or L10I/L24I/M46L/L63P/V82I/I84V substitutions, GRL-216 failed to block the dimerization (FIG. 3). Thus, V82I/I84V substitutions prevented GRL-216 from blocking protease dimerization and played a role in the emergence of HIV-1 resistance to GRL-216.

EXAMPLE Structural analysis of interaction of GRL-216 and darunavir. Counter-ions were deleted from the crystal structures of HIV-1 protease complexed with GRL-216 (PDB ID 3I6O) (16) and darunavir (PDB ID: 2IEN) (13). Bond orders were properly assigned to inhibitor molecules. Hydrogen's were added to all the heavy atoms and their positions were optimized in OPLS2005 force field with constraints on heavy atom positions. A cutoff distance of 3.0 Å between a polar hydrogen and an oxygen or nitrogen atom was used to determine the presence of hydrogen bonds. The structures were analyzed using Maestro version 9.0 (Schrödinger, LLC, New York, N.Y., 2009).

EXAMPLE Structural Analysis of Interactions with GRL-216 with HIV-1 protease. The crystal structures of GRL-216 (PDB ID 3I6O), and DRV (PDB ID 2IEN) (34) were analyzed to gain insight to the similarity and differences in their interactions with HIV-1 protease. Hydrogens were added to the coordinates obtained from the PDB, and minimized with constraints on the heavy atoms in OPLS2005 force field using Maestro 9.0 (Schrodinger, LLC, New York). The bis-THF component of GRL-216 forms hydrogen bonding interaction with D29 and D30 of the protease. Hydrogen bond interactions with D25, D25', and a water molecule-mediated hydrogen bond interactions with I50 and I50' were also observed. These hydrogen bond interactions were also observed for DRV. The P2' ligands of DRV and GRL-216 were different and both of them formed hydrogen bond interactions with different backbone atoms of D30'. The oxygen atom in the methoxybenzene of GRL-216 formed hydrogen bond with the backbone NH of D30', while the aniline nitrogen of darunavir hydrogen bonds to the oxygen of the backbone carbonyl. While the polar interactions of these molecules were similar, there appear to be subtle difference in the non-polar interaction due to the presence of the macrocyclic ring in GRL-216. The macrocyclic ring occupied more volume at the S1'-S2' binding cavity of the protease, and formed more van der Waals interactions with V82 and I84 than the corresponding isopropyl group of the structurally related bis-THF-containing DRV. Without being bound by theory, it is believed herein that the binding of GRL-216 to V82 and V84 along with the polar interactions described herein significantly contribute to its activity against HIV-1 protease. In addition, though without being bound by theory, it is believed herein that V82I and I84V substitutions may have emerged during the in vitro selection process with particularity.

Without being bound by theory, it is believed that the macrocyclic portion of the inhibitors may allow for effective repacking in response to side-chain mutations. Without being bound by theory, it is also believed that such macrocyclic designs provide improved binding to mutants having an increased size of the S2 hydrophobic pocket. The X-ray structure and modeling studies of PI A-77003 indicated that the V82A mutant results in decreased van der Waals interaction with the phenyl rings in both S1 and S1'-subsites (Kempf, 1991; Baldwin, 1995). There is also evidence of repacking of inhibitor side chain and enzyme atoms in the S1-subsite exhibited by the compounds described herein. Without being bound by theory, it is believed that enzyme flexibility in accommodating alternate packing, allows a flexible macrocycle between the P1'-side chain and the P2'-sulfonamide ring to fill in the S1' and S2'-subsites (Baldwin, 1995). In particular, 12-16-membered saturated and unsaturated macrocycles are described that effectively fill in the S1'-S2' hydrophobic pocket of the enzyme active site while retaining all major interactions of PIs 1 and 2 with the protein backbone. Herein described are examples of such inhibitors that maintain potency against both wild-type and mutant strains. PIs that incorporate various macrocycles to effectively fill in the enzyme active site are described.

EXAMPLE Biological Evaluation: The inhibitory potencies of acyclic and cyclic inhibitors were measured by the assay protocol of Toth and Marshall (Toth, M. V.; Marshall, G. R. A simple, continuous fluorometric assay for HIV protease. Int. J. Pep. Protien Res. 1990, 36, 544-55). Compounds that showed potent enzyme inhibition $K_i$ values were further evaluated in an antiviral assay. Biological results for the acyclic compounds 13a-h are shown in TABLE 1. Enzyme inhibitory and antiviral activity of inhibitors 14a-h and 15a-g are shown in TABLE 2. Enzyme inhibitory activity of E and Z isomers of 14a-c are shown in TABLE 3. Enzyme inhibitory activity of 19a-c, 20a-c, and 21a-c are shown in TABLE 4. In TABLES 1-5 the following scale is used for $K_i$ values: (−), >100 nM; (+), ≤100 nM; (++), ≤10 nM; and (+++), ≤1 nM. In TABLES 1-4 the following scale is used for IC$_{50}$ values: (−), >1000 nM; (+), ≤1000; (++), ≤100; and (+++), ≤10.

TABLE 1

13a-h

[Structure of compound 13a-h showing hexahydrofuro[3,2-b]furan carbamate with phenyl, hydroxyl, and N-allyl sulfonamide groups with allyloxy methoxyphenyl]

[General structure showing Z-O-C(O)-N(R²)-CH(R⁵)-CH(OR³)-CH₂-N(L³)-X⁴-Q²-X⁵-L⁴]

| Compound | m | n | $K_i$ | IC$_{50}$ (nM) | Corresponding Ring Size |
|---|---|---|---|---|---|
| 13a | 4 | 4 | + | – | 15 |
| 13b | 4 | 3 | + | – | 14 |
| 13c | 4 | 2 | ++ | | 13 |
| 13d | 4 | 1 | ++ | | 12 |
| 13e | 1 | 4 | ++ | ++ | 12 |
| 13f | 1 | 3 | +++ | ++ | 11 |
| 13g | 1 | 2 | +++ | | 10 |
| 13h | 1 | 1 | +++ | | 9 |

TABLE 2

[Structure showing hexahydrofuro[3,2-b]furan carbamate with phenyl, OH, and R substituent]

| Ring Size | Compound | | $K_i$ | IC$_{50}$ |
|---|---|---|---|---|
| 15 | 14a | [macrocyclic structure with OMe phenyl sulfonamide] | +++ | ++ |
| 14 | 14b | [macrocyclic structure with OMe phenyl sulfonamide] | +++ | +++ |

TABLE 2-continued

[Structure showing hexahydrofuro[3,2-b]furan carbamate with phenyl, OH, and R substituent]

| Ring Size | Compound | | $K_i$ | IC$_{50}$ |
|---|---|---|---|---|
| 13 | 14c | [macrocyclic structure] | +++ | +++ |
| 12 | 14d | [macrocyclic structure] | +++ | ++ |
| 12 | 14e | [macrocyclic structure] | +++ | ++ |
| 11 | 14f | [macrocyclic structure] | +++ | ++ |
| 10 | 14g | [macrocyclic structure] | +++ | |

TABLE 2-continued

[Structure: bis-tetrahydrofuran carbamate with OH, R, and Ph substituents]

| Ring Size | Compound | | K_i | IC_50 |
|---|---|---|---|---|
| 9 | 14h | [macrocycle with cis-alkene, N-SO2-aryl-OMe] | | ++ |
| 15 | 15a | [macrocycle, N-SO2-aryl-OMe] | +++ | ++ |
| 14 | 15b | [macrocycle, N-SO2-aryl-OMe] | +++ | ++ |
| 13 | 15c | [macrocycle, N-SO2-aryl-OMe] | +++ | ++ |
| 12 | 15d | [macrocycle, N-SO2-aryl-OMe] | +++ | ++ |
| 11 | 15f | [macrocycle, N-SO2-aryl-OMe] | +++ | ++ |
| 10 | 15g | [macrocycle, N-SO2-aryl-OMe] | +++ | +++ |
| 9 | 15h | [macrocycle, N-SO2-aryl-OMe] | ++ | ++ |

TABLE 3

[Structure: bis-tetrahydrofuran carbamate with OH, R, and Ph substituents]

| Ring Size | Compound | | K_i | IC_50 |
|---|---|---|---|---|
| 15 | 14a-E | [macrocycle with trans-alkene, N-SO2-aryl-OMe] | +++ | ++ |

TABLE 3-continued
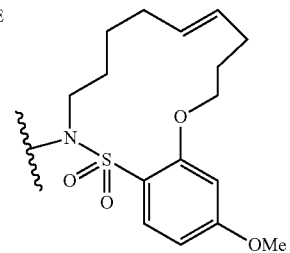
| Ring Size | Compound | | $K_i$ | $IC_{50}$ |
|---|---|---|---|---|
| 14 | 14b-E | 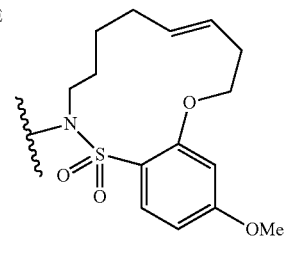 | +++ | +++ |
| 13 | 14c-E | 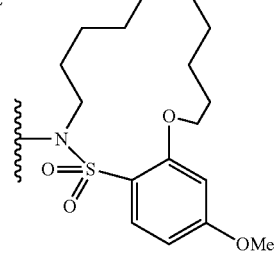 | +++ | +++ |
| 15 | 14a-Z | 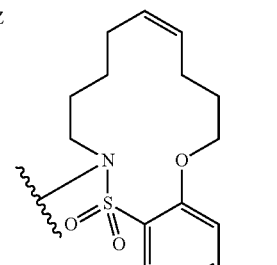 | +++ | − |
| 14 | 14b-Z | 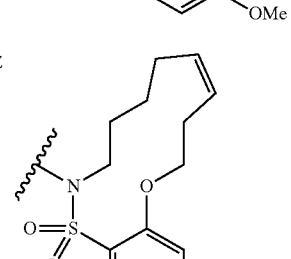 | +++ | +++ |
| 13 | 14c-Z | 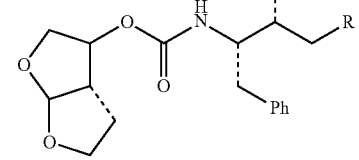 | +++ | +++ |
TABLE 4
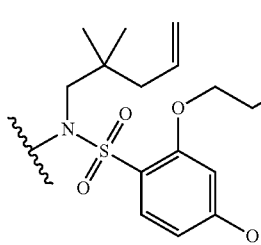
| Compound | | $K_i$ | $IC_{50}$ |
|---|---|---|---|
| 19a | 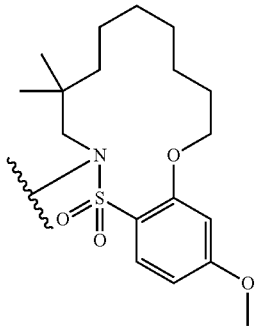 | + | − |
| 22a | 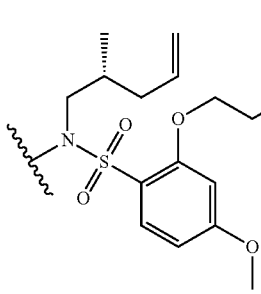 | ++ | − |
| 19b | 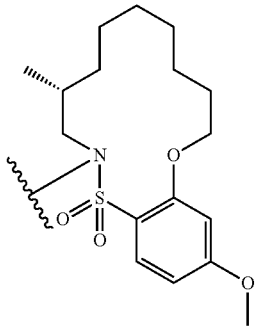 | ++ | ++ |
| 22b | | +++ | + |

TABLE 4-continued
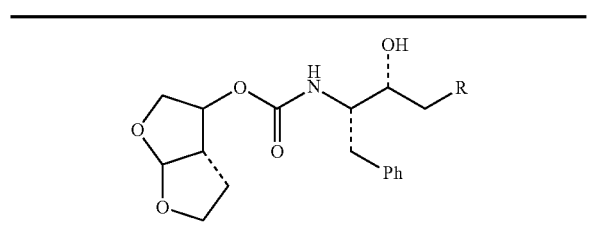
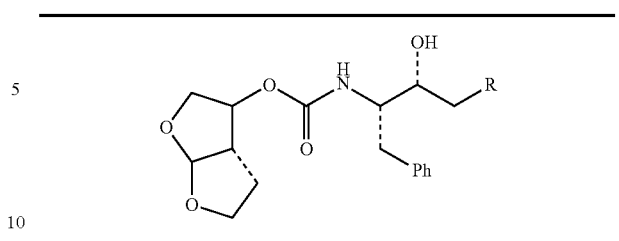
| Compound | | $K_i$ | $IC_{50}$ |
|---|---|---|---|
| 19c | | ++ | − |
| 22c | | +++ | ++ |
| 20a | | + | − |
| 21a | | ++ | − |
| Compound | | $K_i$ | $IC_{50}$ |
|---|---|---|---|
| 20b | | ++ | ++ |
| 21b | | ++ | +++ |
| 20c | | +++ | +++ |
| 21c | | +++ | ++ |

TABLE 5

| Inhibitor | Structure | $K_i$ |
| --- | --- | --- |
| 0649A | 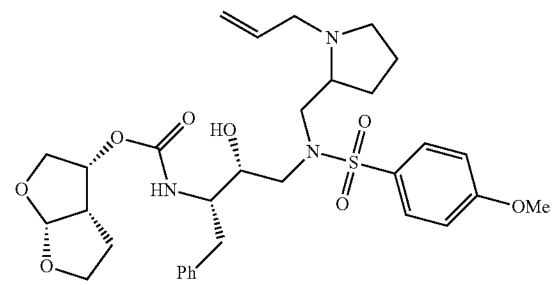 [SMILES: C=CCN1CCCC1CN(C[C@@H](O)[C@H](Cc1ccccc1)NC(=O)O[C@H]1CO[C@H]2OCC[C@H]21)S(=O)(=O)c1ccc(OC)cc1] | ++ |
| 0659A | 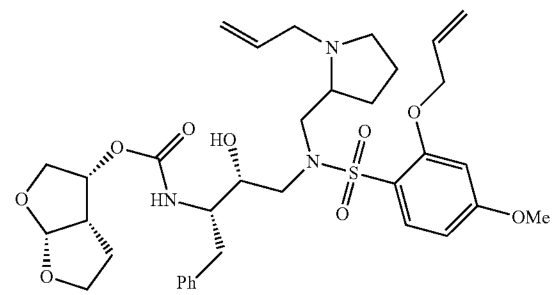 [SMILES: C=CCOc1cc(OC)ccc1S(=O)(=O)N(CC1CCCN1CC=C)C[C@@H](O)[C@H](Cc1ccccc1)NC(=O)O[C@H]1CO[C@H]2OCC[C@H]21] | − |
| 00610A | 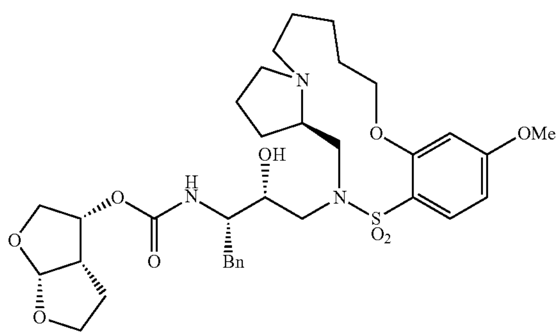 [SMILES: COc1ccc2c(c1)OCCCCCN1CCC[C@@H]1CN(C[C@@H](O)[C@H](Cc1ccccc1)NC(=O)O[C@H]1CO[C@H]3OCC[C@H]31)S2(=O)=O] | − |
| 00810A | 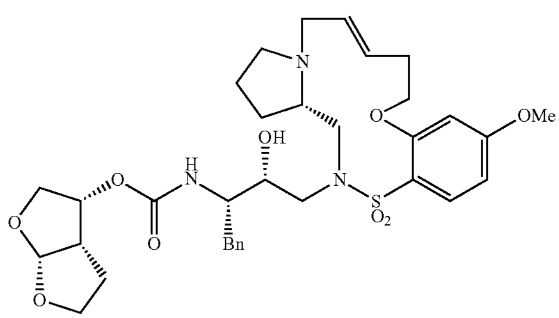 [SMILES: COc1ccc2c(c1)OCC/C=C/CN1CCC[C@H]1CN(C[C@@H](O)[C@H](Cc1ccccc1)NC(=O)O[C@H]1CO[C@H]3OCC[C@H]31)S2(=O)=O] | − |
| 00910A | 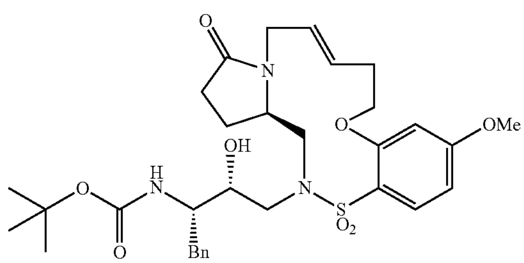 [SMILES: COc1ccc2c(c1)OCC/C=C/CN1C(=O)CC[C@@H]1CN(C[C@@H](O)[C@H](Cc1ccccc1)NC(=O)OC(C)(C)C)S2(=O)=O] | − |

TABLE 5-continued

| Inhibitor | Structure | $K_i$ |
|---|---|---|
| 01010A | 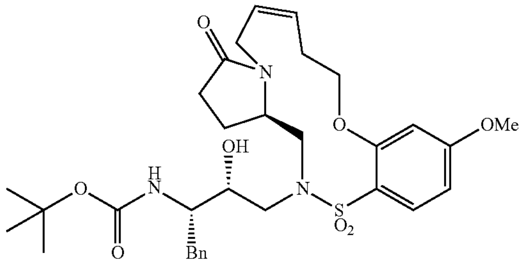 [SMILES: COc1ccc2c(c1)OCC/C=C\CN1C(=O)CC[C@@H]1CN(C[C@@H](O)[C@H](Cc1ccccc1)NC(=O)OC(C)(C)C)S2(=O)=O] | − |
| 01110A | 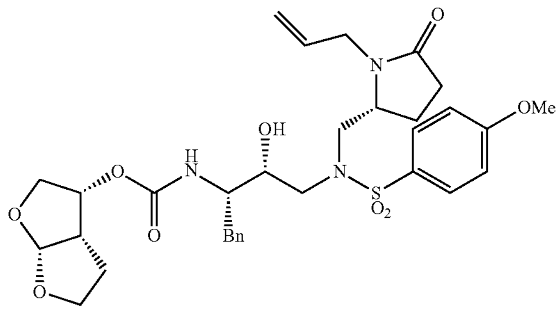 [SMILES: C=CCN1C(=O)CC[C@@H]1CN(C[C@@H](O)[C@H](Cc1ccccc1)NC(=O)O[C@H]1CO[C@H]2OCC[C@H]21)S(=O)(=O)c1ccc(OC)cc1] | +++ |
| 01210A | 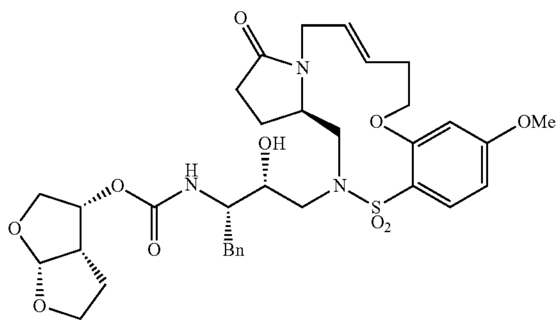 [SMILES: COc1ccc2c(c1)OCC/C=C/CN1C(=O)CC[C@@H]1CN(C[C@@H](O)[C@H](Cc1ccccc1)NC(=O)O[C@H]1CO[C@H]3OCC[C@H]31)S2(=O)=O] | +++ |
| 01310A | 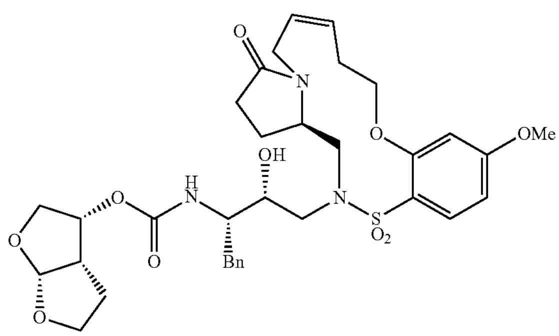 [SMILES: COc1ccc2c(c1)OCC/C=C\CN1C(=O)CC[C@@H]1CN(C[C@@H](O)[C@H](Cc1ccccc1)NC(=O)O[C@H]1CO[C@H]3OCC[C@H]31)S2(=O)=O] | + |
| 01410A | 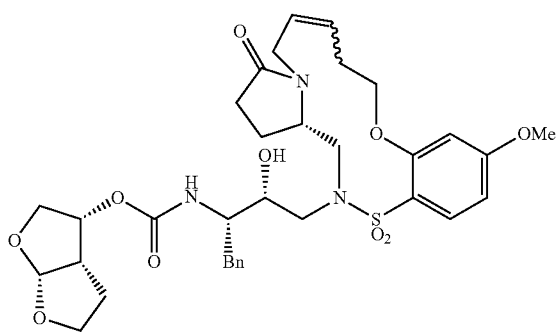 [SMILES: COc1ccc2c(c1)OCCC=CCN1C(=O)CC[C@H]1CN(C[C@@H](O)[C@H](Cc1ccccc1)NC(=O)O[C@H]1CO[C@H]3OCC[C@H]31)S2(=O)=O] | − |

TABLE 5-continued

| Inhibitor | Structure | $K_i$ |
|---|---|---|
| 02110A | 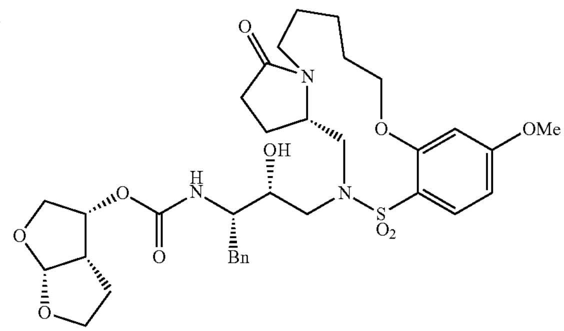 [SMILES: COc1ccc2c(c1)OCCCCCN1C(=O)CC[C@H]1CN(C[C@@H](O)[C@H](Cc1ccccc1)NC(=O)O[C@H]1CO[C@H]3OCC[C@H]31)S2(=O)=O] | + |
| 02210A | 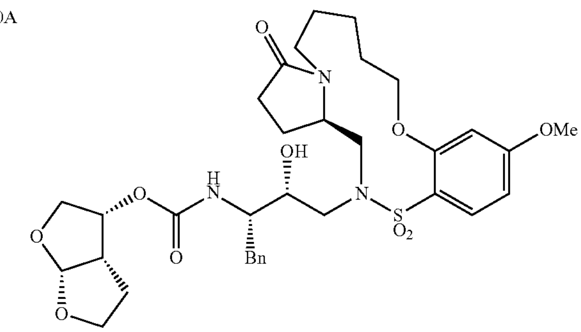 | +++ |

What is claimed is:

1. A compound of the formula

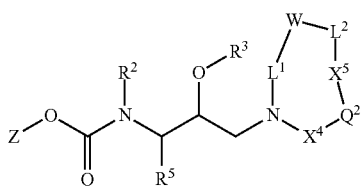

or a pharmaceutically acceptable salt thereof; wherein
$R^2$ and $R^3$ are hydrogen;
$R^5$ is arylalkyl, which is optionally substituted;
$X^4$ is $SO_2$;
$X^5$ is oxygen;
$L^1$ and $L^2$ are independently alkylene, which is optionally substituted;
W is (Z)—(H)C=C(H);
$Q^2$ is 4-methoxy-1,2-phenylene; and
Z is a bicyclic heterocycle, which is optionally substituted.

2. The compound of claim 1 wherein $L^1$ is $CH_2$ $(CH_2)_mCH_2$; $L^2$ is $CH_2(CH_2)_nCH_2$; m is from 0 to about 4; and n is from 0 to about 4.

3. The compound of claim 1 wherein $L^1$ is $CH_2CH_2CH_2CH_2$.

4. The compound claim 2 wherein m is 2; and n is 0.

5. The compound of claim 1 wherein Z is a bicycle heterocycle comprising at least one oxygen.

6. The compound of claim 1 wherein Z has the formula,

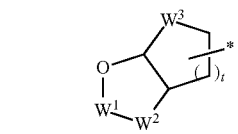

which is optionally substituted, wherein
* indicates the point of attachment; t is 0 to 4;
$W^1$ is optionally substituted alkylene;
$W^2$ represents optionally substituted alkylene; and
$W^3$ is optionally substituted alkylene.

7. The compound of claim 1 wherein Z has formula

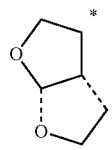

where * indicates the point of attachment.

8. The compound of claim 1 wherein $R^5$ is optionally substituted benzyl.

9. The compound of claim 1 which is a compound of the formula

73
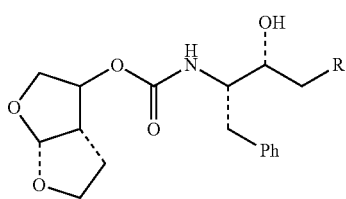
wherein R is selected from the group consisting of
a)
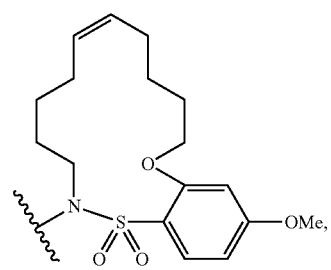
b)
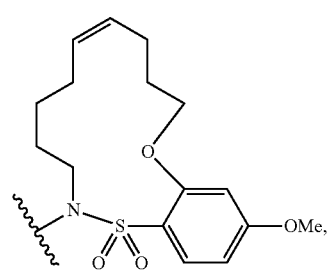
c)
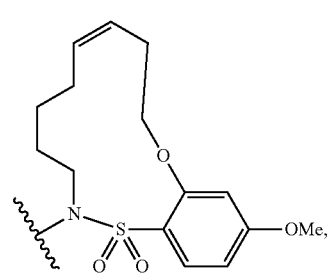
d)
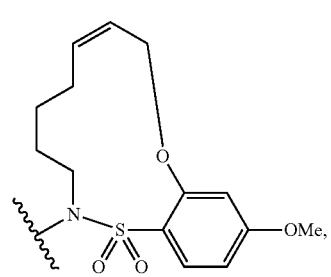
e)
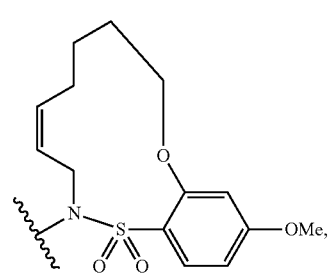
74
-continued
f)
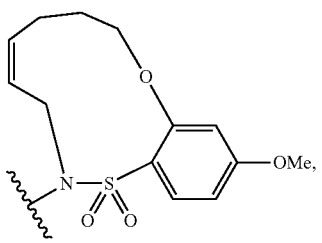
g)
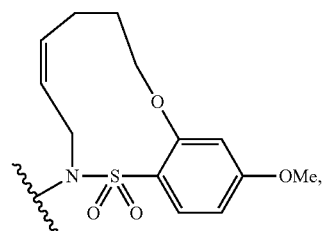
h)
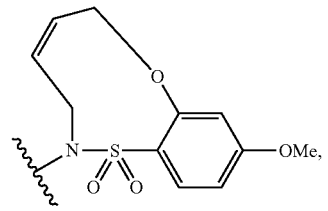
s)
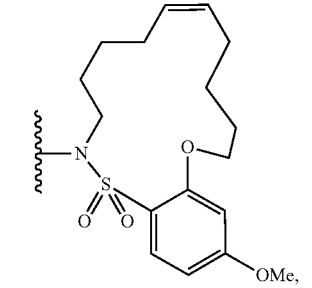
t)
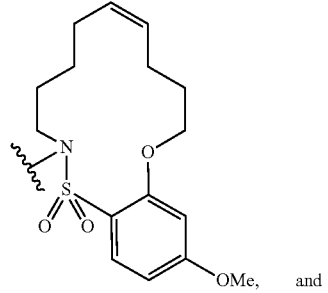
and
u)
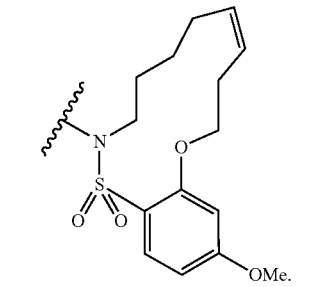

10. A pharmaceutical composition comprising the compound of claim 1 in a therapeutically effective amount for treating HIV infection, and one or more of a carrier, diluent, excipient therefor, or a combination thereof.

11. A compound having the formula:

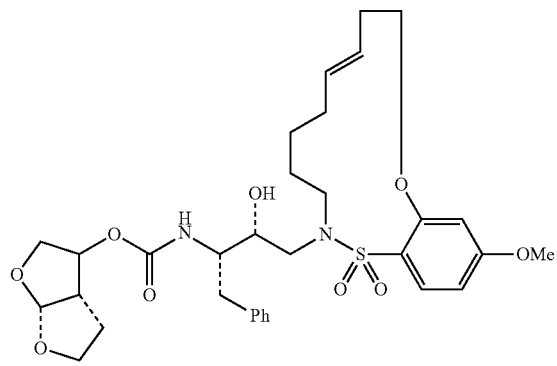

or a pharmaceutically acceptable salt thereof.

12. The compound of claim 1 having the formula:

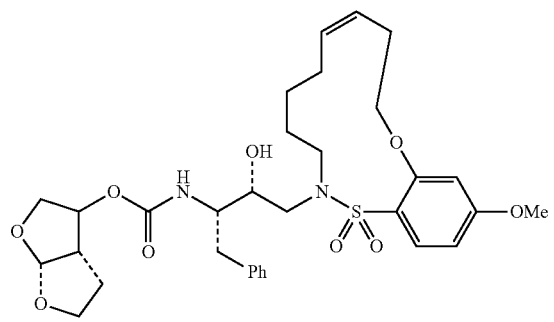

or a pharmaceutically acceptable salt thereof.

13. A compound of the formula:

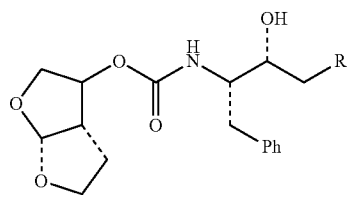

wherein R is selected from the group consisting of

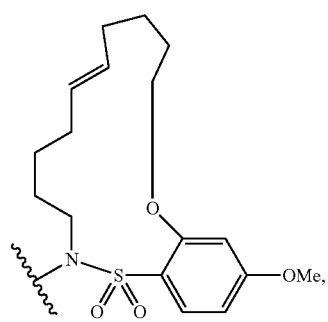

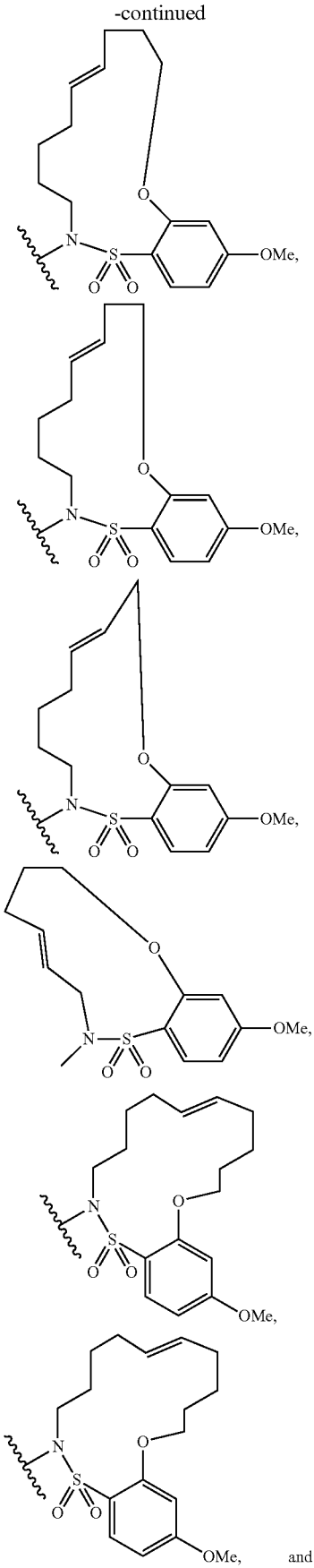

and

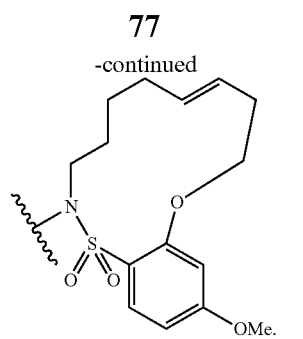
* * * * *